(12) United States Patent
Chernomorsky et al.

(10) Patent No.: US 7,744,852 B2
(45) Date of Patent: *Jun. 29, 2010

(54) METHODS AND SYSTEMS FOR MARKING POST BIOPSY CAVITY SITES

(75) Inventors: Ary S. Chernomorsky, Walnut Creek, CA (US); Sean Chris Daniel, Palo Alto, CA (US); James W. Vetter, Portola Valley, CA (US)

(73) Assignee: Rubicor Medical, LLC, Redwood City, CA (US)

( * ) Notice: Subject to any disclaimer, the term of this patent is extended or adjusted under 35 U.S.C. 154(b) by 713 days.

This patent is subject to a terminal disclaimer.

(21) Appl. No.: 11/673,510

(22) Filed: Feb. 9, 2007

(65) Prior Publication Data

US 2007/0135711 A1 Jun. 14, 2007

(51) Int. Cl.
*A61K 51/00* (2006.01)
*A61K 49/00* (2006.01)
*A61K 9/28* (2006.01)
*A61K 33/00* (2006.01)

(52) U.S. Cl. .................. 424/1.37; 424/9.2; 424/471; 424/600

(58) Field of Classification Search ............ 424/1.37, 424/9.2, 471, 600
See application file for complete search history.

(56) References Cited

U.S. PATENT DOCUMENTS

| | | | |
|---|---|---|---|
| 3,902,497 A | 9/1975 | Casey | |
| 3,993,072 A | 11/1976 | Zaffaroni | |
| 4,193,813 A | 3/1980 | Chvapil | |
| 4,466,442 A | 8/1984 | Hilmann et al. | |
| 4,619,261 A | 10/1986 | Guerriero | |
| 5,081,997 A | 1/1992 | Bosley, Jr. | |
| 5,123,414 A | 6/1992 | Unger | |
| 5,186,922 A | 2/1993 | Shell et al. | |
| 5,195,988 A | 3/1993 | Haaga | |
| 5,281,408 A | 1/1994 | Unger | |
| 5,326,350 A | 7/1994 | Li | |
| 5,334,216 A | 8/1994 | Vidal et al. | |
| 5,334,381 A | 8/1994 | Unger | |
| 5,376,376 A | 12/1994 | Li | |
| 5,383,466 A | 1/1995 | Partika | |
| 5,478,352 A | 12/1995 | Fowler | |
| 5,487,392 A | 1/1996 | Haaga | |
| 5,510,418 A | 4/1996 | Rhee et al. | |
| 5,522,840 A | 6/1996 | Krajicek | |
| 5,547,656 A | 8/1996 | Unger | |
| 5,571,181 A | 11/1996 | Li | |
| 5,676,146 A | 10/1997 | Scarborough | |
| 5,676,925 A | 10/1997 | Klaveness et al. | |
| 5,752,974 A | 5/1998 | Rhee et al. | |
| 5,807,581 A | 9/1998 | Rosenblatt et al. | |
| 5,856,367 A | 1/1999 | Barrows et al. | |
| 6,022,362 A | 2/2000 | Lee et al. | |
| 6,068,600 A | 5/2000 | Johnson et al. | |
| 6,068,857 A | 5/2000 | Weitschies et al. | |
| 6,071,301 A | 6/2000 | Cragg et al. | |
| 6,090,996 A | 7/2000 | Li | |
| 6,106,473 A | 8/2000 | Violante et al. | |
| 6,136,293 A | 10/2000 | Schneider et al. | |
| 6,140,452 A | 10/2000 | Felt et al. | |
| 6,161,034 A | 12/2000 | Burbank et al. | |
| 6,183,496 B1 | 2/2001 | Urbanski | |
| 6,183,497 B1 | 2/2001 | Sing et al. | |
| 6,193,951 B1 | 2/2001 | Ottoboni et al. | |
| 6,264,695 B1 | 7/2001 | Stoy | |
| 6,270,464 B1 | 8/2001 | Fulton, III et al. | |
| 6,306,154 B1 | 10/2001 | Hudson et al. | |
| 6,333,029 B1 | 12/2001 | Vyakarnam et al. | |
| 6,347,241 B2 | 2/2002 | Burbank et al. | |
| 6,356,782 B1 | 3/2002 | Sirimanne et al. | |
| 6,371,904 B1 | 4/2002 | Sirimanne et al. | |
| 6,394,965 B1 | 5/2002 | Klein | |
| 6,427,081 B1 | 7/2002 | Burbank et al. | |
| 6,443,898 B1 | 9/2002 | Unger et al. | |
| 6,544,496 B1 | 4/2003 | Schroder | |
| 6,567,689 B2 | 5/2003 | Burbank et al. | |

(Continued)

OTHER PUBLICATIONS

Lisa Brannon-Peppas, "Polymers in controlled drug delivery" Medical Plastics and Biomaterials Magazine (1997).

(Continued)

*Primary Examiner*—Raymond J Henley, III
(74) *Attorney, Agent, or Firm*—Young Law Firm, P.C.

(57) ABSTRACT

A method of marking a cavity in a breast for subsequent visualization may include steps of providing a device having a delivery opening, a first marker and a second marker, the first and second markers being movable through the delivery opening, the first marker being configured to be visualized by ultrasound and the second marker configured to be radiopaque, the first and second markers being free to move relative to one another; introducing the device into a breast so that the delivery opening is positioned in a cavity formed in the breast; and moving the first marker and the second marker through the delivery opening and into the cavity in the breast, the first and second markers being free to move relative to one another when delivered into the cavity so that the first and second markers may take a number of different positions relative to one another when positioned within the cavity.

103 Claims, 25 Drawing Sheets

U.S. PATENT DOCUMENTS

| | | | |
|---|---|---|---|
| 7,534,452 B2 * | 5/2009 | Chernomorsky et al. | .... 424/600 |
| 7,537,788 B2 * | 5/2009 | Chernomorsky et al. | .... 424/600 |
| 2001/0003791 A1 | 6/2001 | Burbank et al. | |
| 2001/0044583 A1 | 11/2001 | Unger et al. | |
| 2002/0019597 A1 | 2/2002 | Dubrul et al. | |
| 2002/0022781 A1 | 2/2002 | McIntire et al. | |
| 2002/0035324 A1 | 3/2002 | Sirimanne et al. | |
| 2002/0038087 A1 | 3/2002 | Burbank et al. | |
| 2002/0058960 A1 | 5/2002 | Hudson et al. | |
| 2002/0077653 A1 | 6/2002 | Hudson et al. | |
| 2002/0082517 A1 | 6/2002 | Klein | |
| 2002/0107437 A1 | 8/2002 | Sirimanne et al. | |
| 2002/0151796 A1 | 10/2002 | Koulik | |
| 2002/0161298 A1 | 10/2002 | Burbank et al. | |
| 2002/0188196 A1 | 12/2002 | Burbank et al. | |
| 2003/0004563 A1 | 1/2003 | Jackson et al. | |
| 2003/0013989 A1 | 1/2003 | Obermiller et al. | |
| 2003/0036697 A1 | 2/2003 | Ottoboni et al. | |
| 2003/0095997 A1 | 5/2003 | Ruszczak et al. | |
| 2003/0100830 A1 | 5/2003 | Zhong et al. | |
| 2004/0006355 A1 | 1/2004 | Vetter et al. | |

OTHER PUBLICATIONS

Edmunson et al., "Dosimetric characteristics of the mammosite rts, a new breast brachytherapy applicator", Int. J. Radiation Oncology Biol. Phys. 52(4):132-1139, 2002.

Elfrink et al., "Determination of the accuracy of implant reconstruction and dose delivery in brachytherapy in the Netherlands and Belgium", Radiotherapy and Oncology 59:297-306, 2001.

Kestin et al., "Improving the dosimetric coverage of interstitial high-dose rate breast implants", Int J. Radiation Oncology Biol. Phys. 46(1):35-43, 2000.

M. Mertig et al. "Dewetting of thin collagenous precursor films" Appl. Phys. A 66, S565-S568 (1998).

Julia R. White MD and J. Frank Wilson MD, FACR, "Brachytherapy and Breast Cancer", Radiation Oncology, Medical College of Wisconsin, Seminars in Surgical Oncology 13:190-195, 1997.

International Search Report dated Jun. 29, 2005, in related International Application No. PCT/US04/11292, filed Apr. 12, 2004 (3pgs).

Written Opinion dated Jun. 29, 2005, in related International Application No. PCT/US04/11292, filed Apr. 12, 2004 (3pgs).

International Preliminary Report on Patentability mailed Feb. 9, 2006, in related International Application No. PCT/US04/11292, filed Apr. 12, 2004 (6pgs).

International Search Report dated Dec. 29, 2004, in related International Application No. PCT/US04/31356, filed Sep. 24, 2004 (3pgs).

Written Opinion dated Dec. 29, 2004, in related International Application No. PCT/US04/31356, filed Sep. 24, 2004 (3pgs).

International Preliminary Report on Patentability mailed Apr. 27, 2006, in related International Application No. PCT/US04/31356, filed Sep. 24, 2004 (6pgs).

Office Action mailed May 31, 2005, in related U.S. Appl. No. 10/627,960, filed Jul. 25, 2003.

Office Action mailed Dec. 30, 2005, in related U.S. Appl. No. 10/627,960, filed Jul. 25, 2003.

Office Action mailed Jun. 23, 2006, in related U.S. Appl. No. 10/627,960, filed Jul. 25, 2003.

Office Action mailed Jan. 9, 2007, in related U.S. Appl. No. 10/627,960, filed Jul. 25, 2003.

Office Action mailed Oct. 18, 2007, in parent U.S. Application No. 10/627,690, filed Jul. 25, 2003.

* cited by examiner

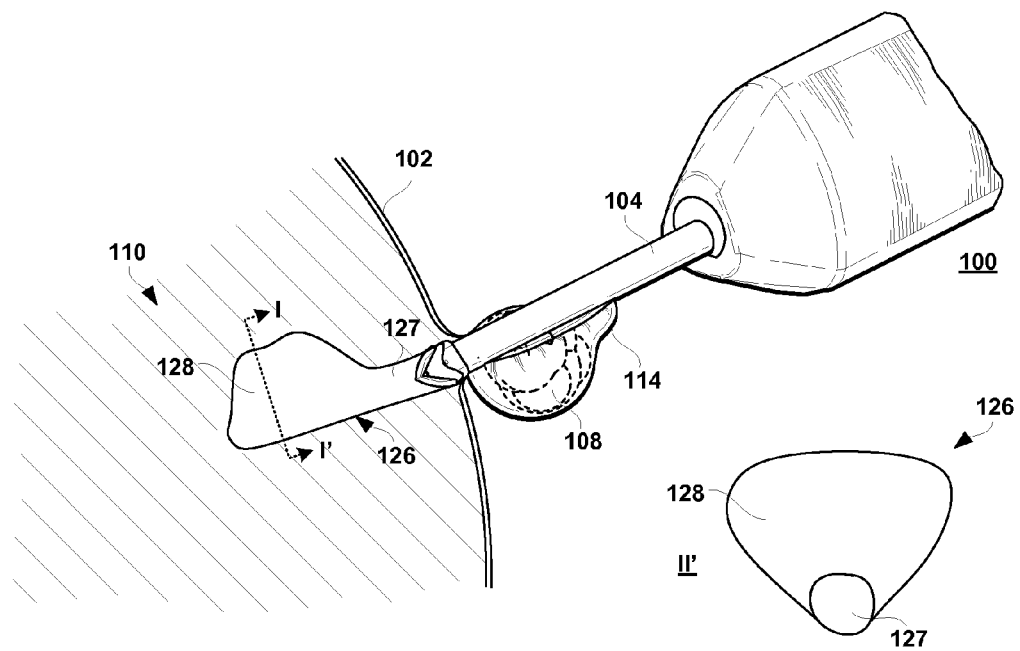
*FIG. 6A*  *FIG. 6B*
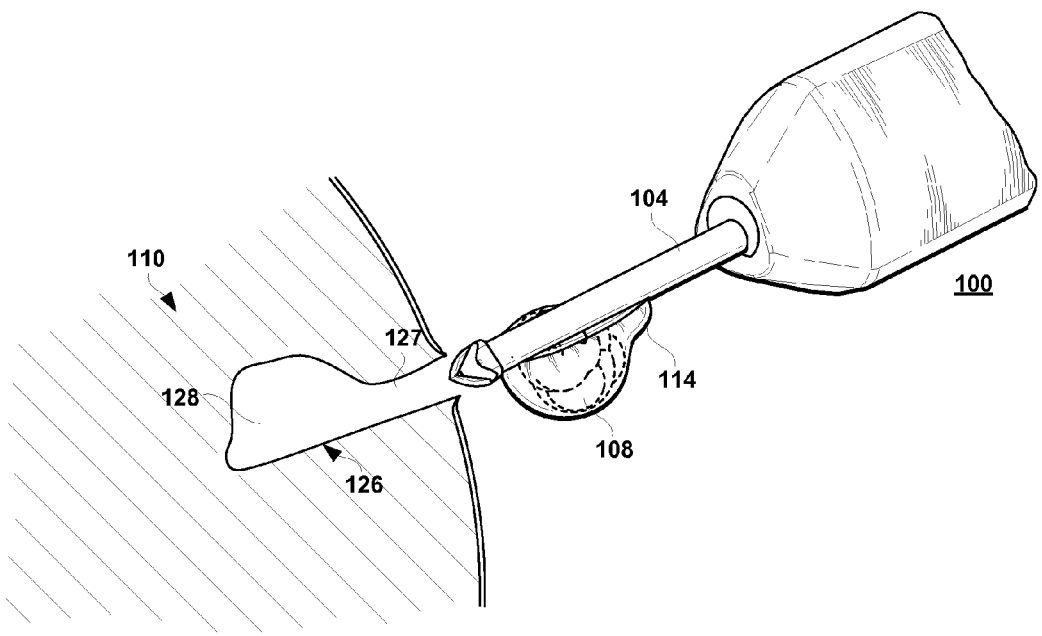
*FIG. 7*

FIG. 14A
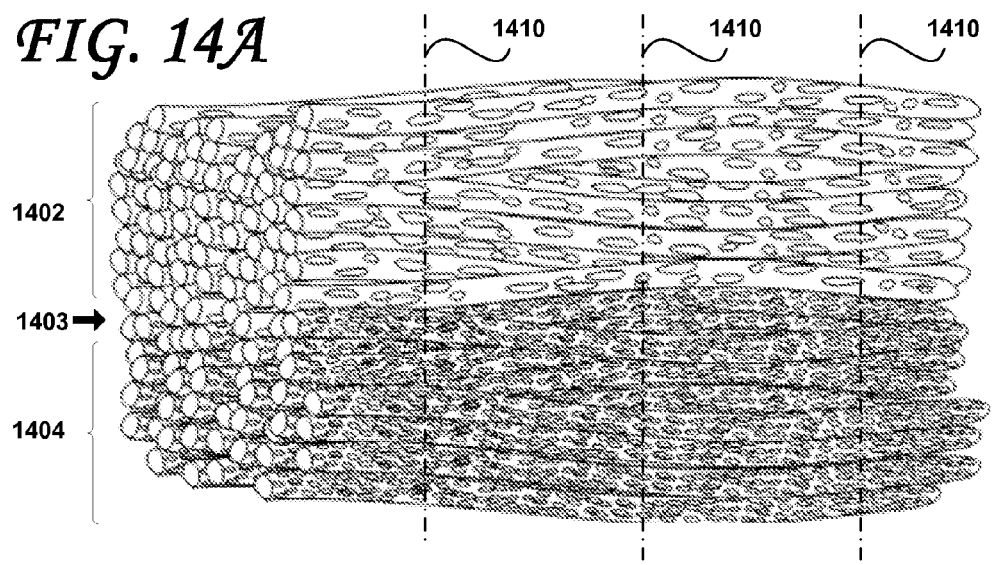
FIG. 14B
FIG. 14C
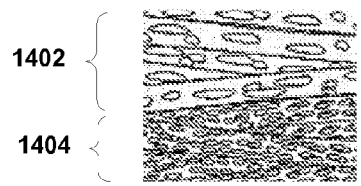
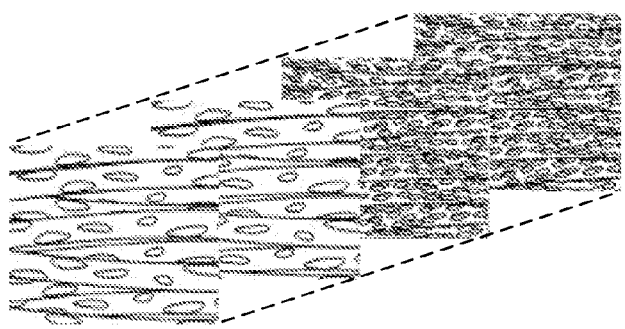
FIG. 14D
FIG. 14E
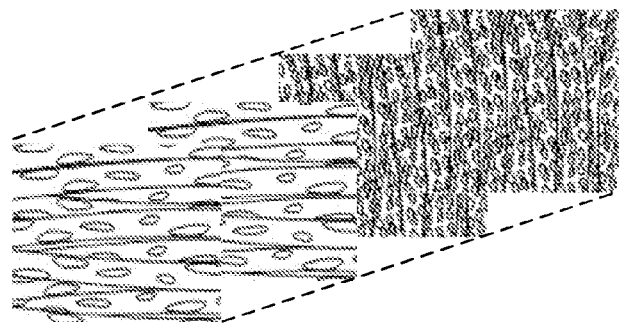

*FIG. 16*  *FIG. 17*
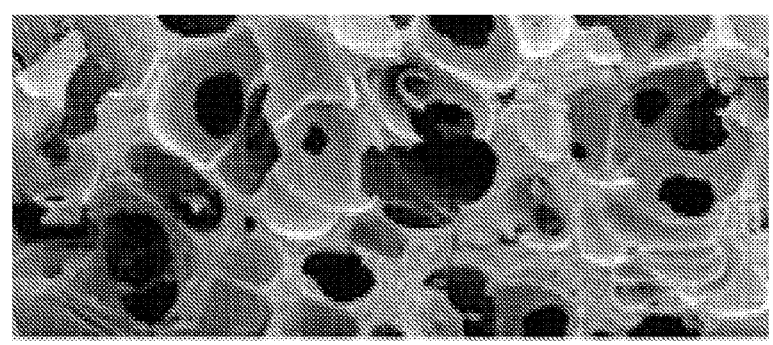
*FIG. 18*  *FIG. 19*
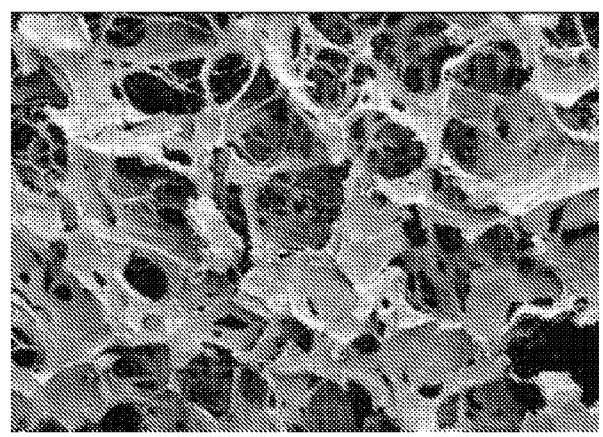
*FIG. 20*

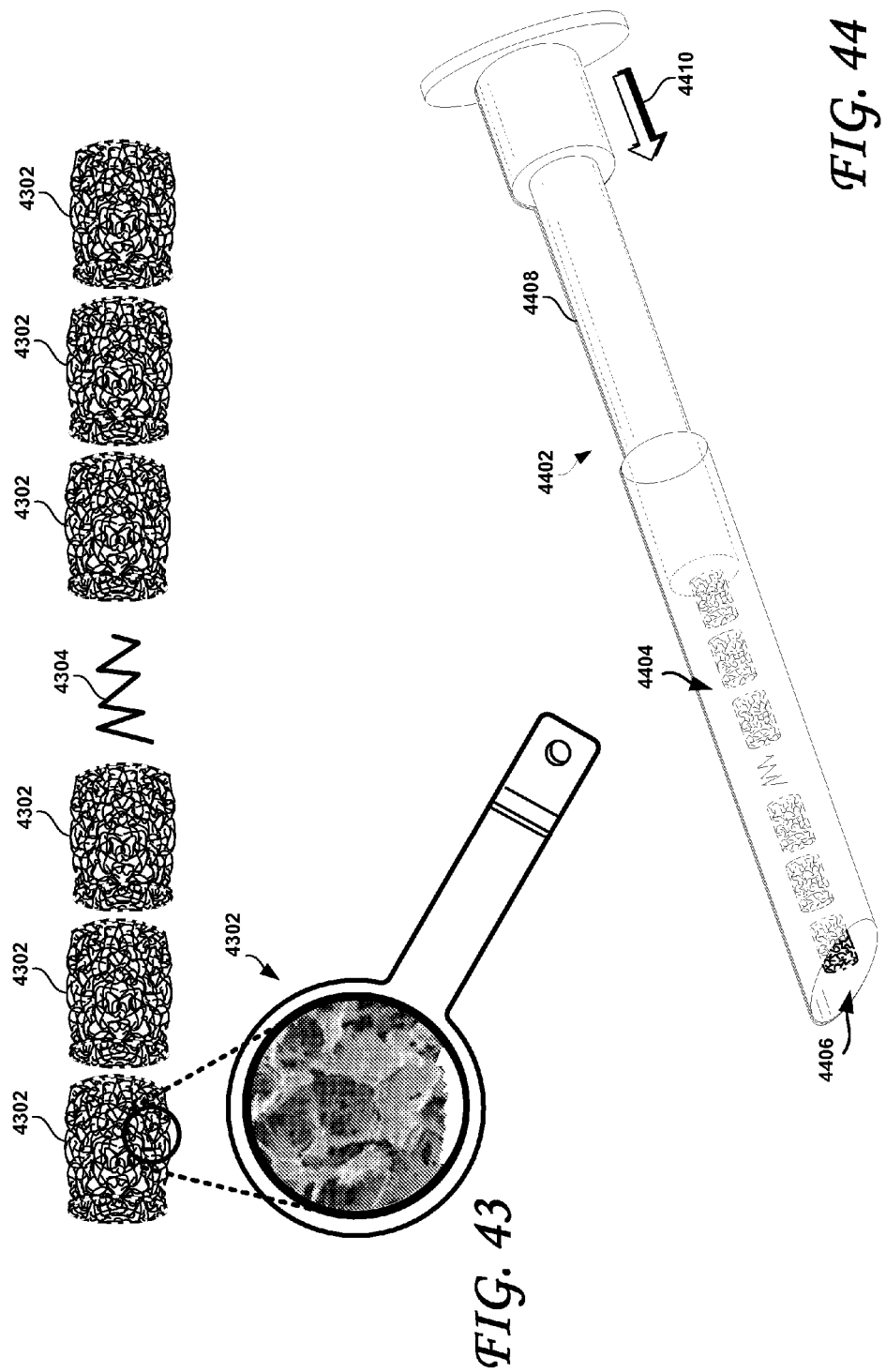

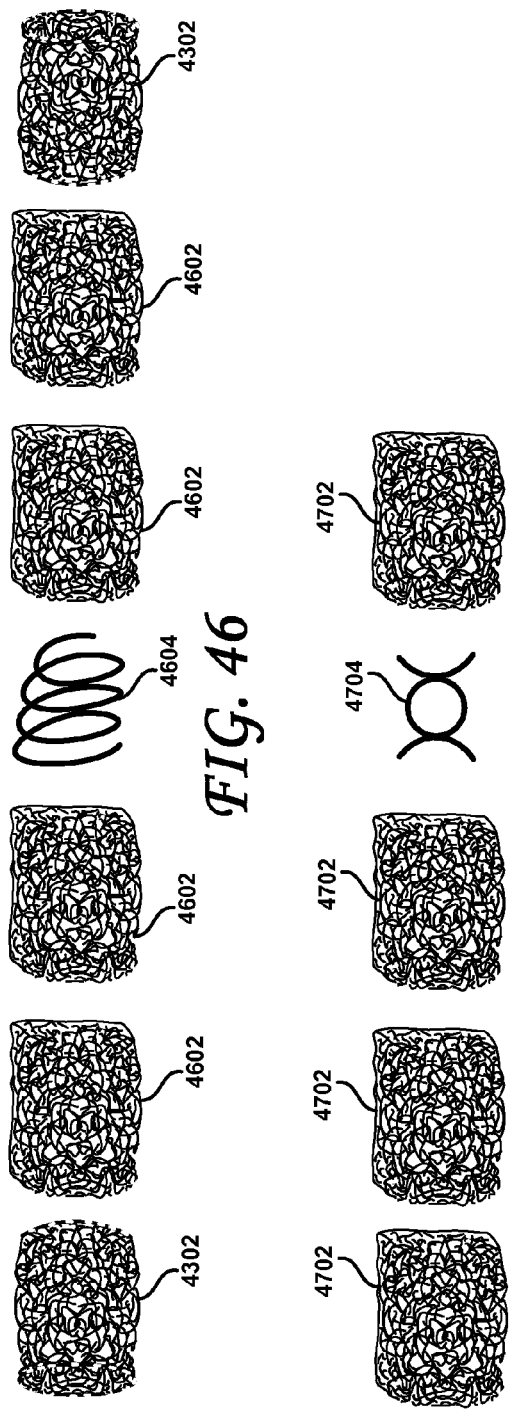
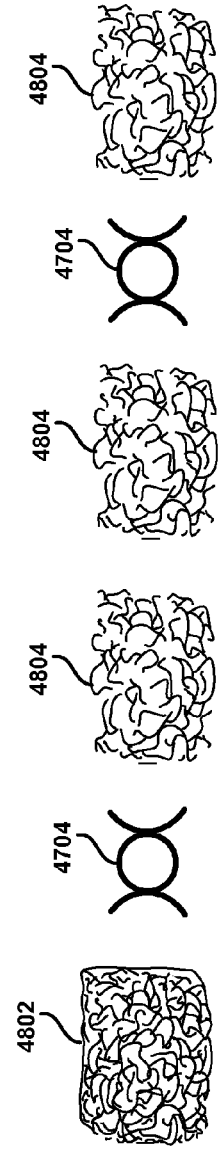
FIG. 46
FIG. 47
FIG. 48

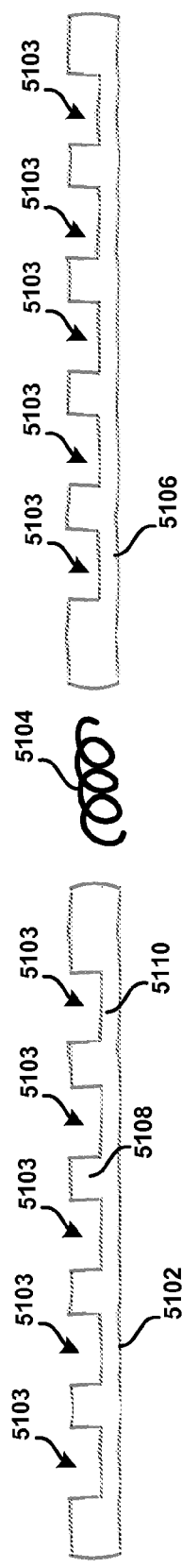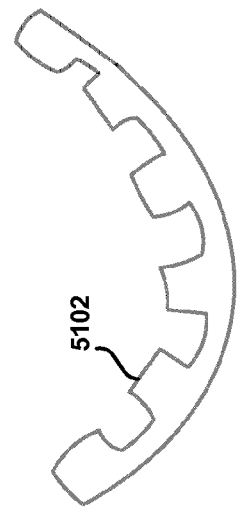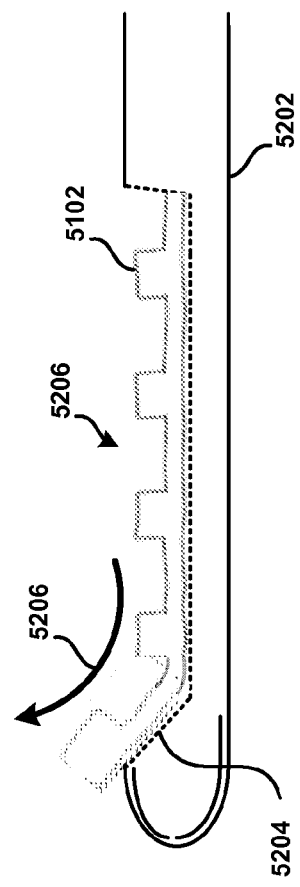
FIG. 51
FIG. 53
FIG. 52

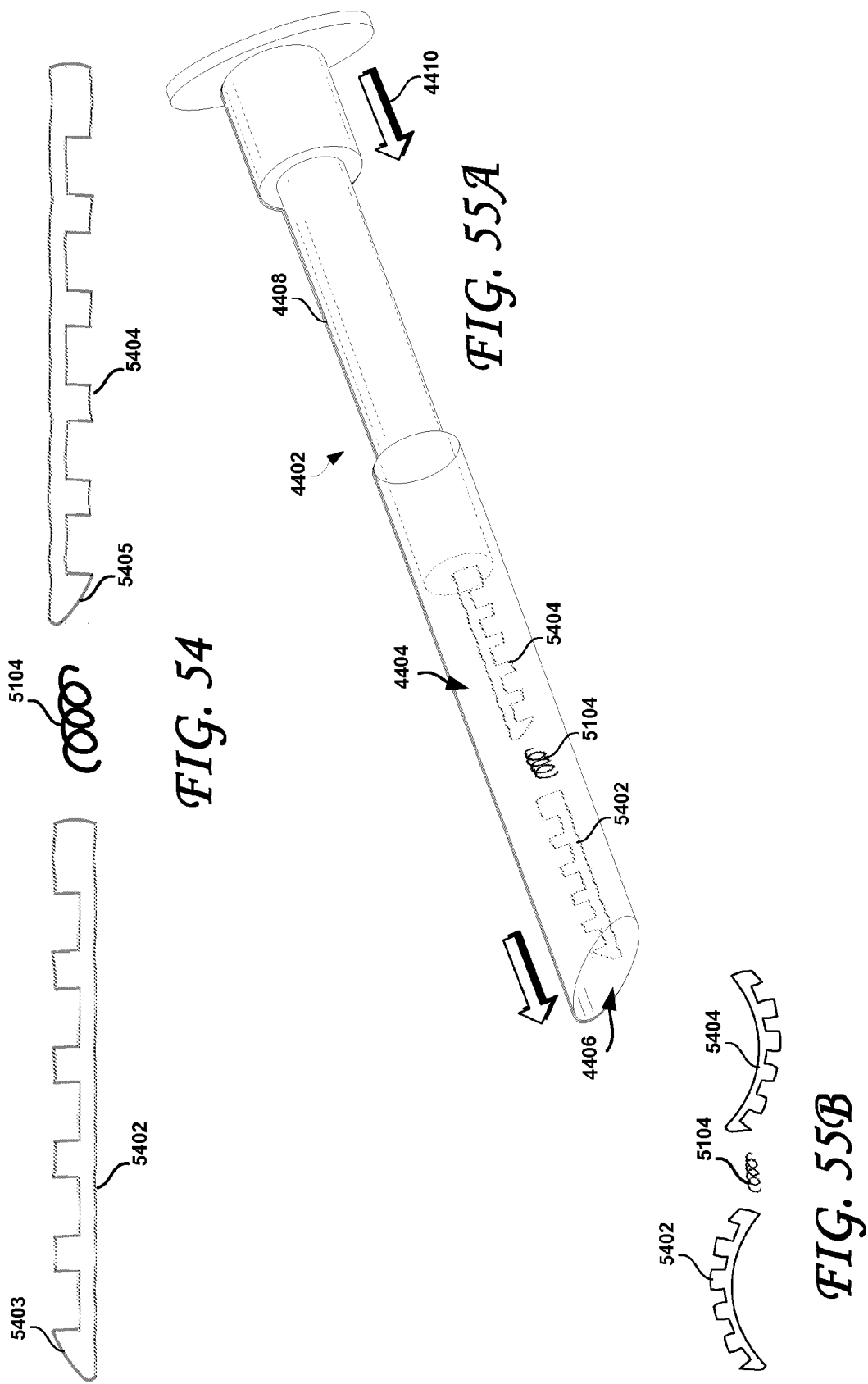

METHODS AND SYSTEMS FOR MARKING POST BIOPSY CAVITY SITES

BACKGROUND OF THE INVENTION

This application is related in subject matter to application Ser. No. 10/688,289, filed Oct. 16, 2003, now U.S. Pat. No. 7,537,788 and application Ser. No. 10/627,960, filed Jul. 25, 2003, which applications are hereby incorporated herein by reference in their entireties.

1. Field of the Invention

The present invention relates to post-biopsy cavity treatment methods and implants. More particularly, the present inventions relates to post-biopsy cavity treatment implants inserted into cavities formed in soft tissue that may be created during a biopsy or therapeutic excisional procedure.

2. Description of the Related Art

Breast biopsies are routinely performed in the United States following a detection of abnormalities discovered through mammographic visualization, manual palpation or ultrasound examination. There are a number of traditional methods to obtain breast biopsy tissue samples, including surgical excisional biopsies and stereotactic and ultrasound guided needle breast biopsies. Recently, methodologies have emerged that are based upon percutaneous minimally invasive large intact tissue sample collection. The use of these devices results in a unique cavity connected to the skin by a narrow neck. For example, such cavities may generally resemble an igloo. It is becoming apparent that the post-biopsy cavities left within the patient by such procedures may benefit from different post procedure treatment methods and implants, as compared to the post-procedure treatment methods and implants (if any) conventionally employed to treat cavities left by needle, core biopsy procedures or open surgical procedures. In part, this need for new post-procedure methods and implants is driven by the different nature, size and shape of the cavity created by such emerging percutaneous minimally invasive large intact tissue sample collection methods and devices.

In certain cases, locating a previously biopsied area is highly desirable. Therefore, to mark the biopsy site, a variety of biopsy site markers and identifiers have been developed, ranging from metal clips to pellets and sponges placed during or right after the biopsy procedure. Usually, these markers contain radiopaque and/or echogenic articles and include features such as metal clips and air or gas bubbles incorporated in a biodegradable matrix. However, existing markers are believed to be unsuited to the unique size and shape of some cavities, in that they do not adequately fill the cavity, do not adequately promote tissue ingrowth, and are not easily visualizable, among other disadvantages. It has become apparent, therefore, that new post-biopsy and post-procedure cavity implants and treatment methods are needed that are better suited to the percutaneous minimally invasive large intact tissue sample collection methods and devices that are currently gaining favor in the medical community.

SUMMARY OF THE INVENTION

According to an embodiment thereof, the present invention is a device to deliver a soft tissue marker. The soft tissue marker delivery device may include an introducer that may define an internal lumen; a plurality of discrete substantially non-swellable elements disposed within the internal lumen, each being formed of one or more of a porous material and a non-porous material, and a radiopaque element disposed within the internal lumen adjacent to one or more of the plurality of discrete substantially non-swellable elements, the radiopaque element being external to and uncoupled from each of the plurality of discrete substantially non-swellable elements.

According to further embodiments, the porous material may define surfaces that form interconnected internal voids. The porous material may define internal surfaces that form internal voids. A majority of the internal surfaces may be common to more than one of these internal voids. Indeed, the porous material may define surfaces that form primarily interconnected internal voids, as opposed to forming primarily entrapped discrete bubbles. The porous material may have a controlled pore architecture with respect to one or more of, for example, pore density, pore shape, pore orientation and pore dimensions. One or more of the plurality of discrete substantially non-swellable elements may have a degree of porosity that is different from the degree of porosity of another one of the plurality of discrete substantially non-swellable elements. Both the porous material and the non-porous material may be configured to promote echogenicity. The porous material of one of the plurality of discrete substantially non-swellable elements may have a first controlled pore architecture and the porous material of an other one of the plurality of discrete substantially non-swellable elements may have a second controlled pore architecture that is different from the first controlled pore architecture. The first controlled pore architecture may differ from the second controlled pore architecture with respect to one or more of, for example, pore density, pore shape, pore orientation and pore dimensions. The porous material of the plurality of discrete substantially non-swellable elements may be biodegradable. The porous material of one or more of the plurality of discrete substantially non-swellable elements may include one or more of a polylactide (PLA), a polyglycolide (PGA), a poly (lactide-co-glycolide) (PLA-PGA), a polyglyconate, a polyanhydride, a lipid, a polysaccharide, and a polyorthoester, for example.

One or more of the plurality of discrete substantially non-swellable elements may have a first shape and an other one of the plurality of discrete substantially non-swellable elements may have a second shape that is different from the first shape. One or more of the plurality of discrete substantially non-swellable elements may have a substantially cylindrical shape. One or more of the plurality of discrete substantially non-swellable elements may have a substantially rectangular shape.

The radiopaque element may be configured to appear clearly artificial when viewed under X-ray. The radiopaque element may be configured to appear clearly artificial when viewed under ultrasound. The plurality of discrete substantially non-swellable elements may be configured to appear clearly artificial when viewed under ultrasound. The combination of the plurality of discrete substantially non-swellable elements and the radiopaque element may be configured to appear clearly artificial when viewed under ultrasound. The radiopaque element may be formed of a non-ferrous metal, and/or may include a portion having a paramagnetic property. More than one radiopaque element may be disposed within the internal lumen of the introducer.

According to another embodiment, the present invention is a soft tissue marker for delivery to a biopsy site within a patient. The soft tissue marker may include a plurality of discrete substantially non-swellable elements, each being formed of a porous material or a (substantially) non-porous material, and a radiopaque element disposed adjacent to one or more of the plurality of discrete substantially non-swellable porous elements. The radiopaque element may be external to and uncoupled from each of the plurality of discrete substantially non-swellable elements.

The porous material may define surfaces that form interconnected internal voids. The porous material may define internal surfaces that form internal voids. A majority of the internal surfaces may be common to more than one of the internal voids. The porous material may define surfaces that form primarily interconnected internal voids, as opposed to forming primarily entrapped discrete bubbles. The porous material may have a controlled pore architecture with respect to one or more of, for example, pore density, pore shape, pore orientation and pore dimensions. One or more of the plurality of discrete substantially non-swellable elements may have a degree of porosity that is different from the degree of porosity of another one of the plurality of discrete substantially non-swellable elements. Both the porous material and the non-porous material may be configured to promote echogenicity. The porous material of one of the plurality of discrete substantially non-swellable elements may have a first controlled pore architecture and the porous material of an other one of the plurality of discrete substantially non-swellable elements may have a second controlled pore architecture that is different from the first controlled pore architecture. The first controlled pore architecture may differ from the second controlled pore architecture with respect to, for example, pore density, pore shape, pore orientation and/or pore dimensions. The porous material of the plurality of discrete substantially non-swellable elements may be biodegradable. The porous material of one or more of the plurality of discrete substantially non-swellable elements may include a polylactide (PLA), a polyglycolide (PGA), a poly(lactide-co-glycolide) (PLA-PGA), a polyglyconate, a polyanhydride, a lipid, a polysaccharide, and/or a polyorthoester.

One or more of the plurality of discrete substantially non-swellable elements may have a first shape and an other one of the plurality of discrete substantially non-swellable elements may have a second shape that is different from the first shape. One or more of the plurality of discrete substantially non-swellable elements may have a substantially cylindrical shape. One or more of the plurality of discrete substantially non-swellable elements may have a substantially rectangular shape—or any other shape. The radiopaque element may be configured to appear clearly artificial when viewed under X-ray. The radiopaque element may be configured to appear clearly artificial when viewed under ultrasound. The radiopaque element may be formed of a non-ferrous metal and may include a portion having a paramagnetic property. More than one radiopaque element may be disposed within the internal lumen of the introducer. The plurality of discrete substantially non-swellable elements may be configured to appear clearly artificial when viewed under ultrasound. The combination of the plurality of discrete substantially non-swellable elements and the radiopaque element may be configured to appear clearly artificial when viewed under ultrasound.

According to still another embodiment thereof, the present invention is a method for marking a biopsy site within a patient, comprising the steps of: providing a device having a proximal end, an open distal end, an internal lumen and a piston that is movable within the internal lumen; a plurality of discrete substantially non-swellable elements disposed within the internal lumen, each of which being formed of one or more of a porous material and a non-porous material, and a radiopaque element disposed within the internal lumen adjacent to one or more of the plurality of discrete substantially non-swellable elements, the radiopaque element being external to and uncoupled from each of the plurality of discrete substantially non-swellable porous elements; introducing the distal end of the device into the biopsy site; advancing the piston in a distal direction so that the plurality of discrete substantially non-swellable elements and the radiopaque element may be pushed out the open distal end of the device and into the biopsy site.

Yet another embodiment of the present invention is a method of marking a cavity in a breast for subsequent visualization. This method may include steps of providing a device having a delivery opening, a first marker and a second marker, the first and second markers being movable through the delivery opening, the first marker being configured to be visualized by ultrasound and the second marker configured to be radiopaque, the first and second markers being free to move relative to one another; introducing the device into a breast so that the delivery opening is positioned in a cavity formed in the breast; and moving the first marker and the second marker through the delivery opening and into the cavity in the breast, the first and second markers being free to move relative to one another when delivered into the cavity so that the first and second markers may take a number of different positions relative to one another when positioned within the cavity.

The providing step may be carried out with the first marker being a polymer having a porous structure which enhances visibility of the first marker under ultrasound, the second marker being a metallic structure which enhances visibility of the second marker under x-ray. The providing step may be carried out with the first marker being substantially non-swellable. The providing step may be carried out with the first marker being uncoupled from the second marker. The providing step may be carried out with the first marker including surfaces that form interconnected internal voids. The providing step may be carried out with the first marker defining internal surfaces that form internal voids. A majority of these internal surfaces may be common to more than one of the internal voids. The providing step may be carried out with the first marker defining surfaces that form primarily interconnected internal voids, as opposed to forming primarily entrapped discrete bubbles. The providing step may be carried out with the first marker being porous and having a controlled pore architecture with respect to one or more of (for example) pore density, pore shape, pore orientation and pore dimensions. The providing step may be carried out with the device including a third marker configured to be visualized by ultrasound, the first and third markers may be porous, and the first marker may have a degree of porosity that is different from the degree of porosity of the third marker. The providing step may be carried out with the device including a third marker configured to be visualized by ultrasound, the first marker may have a first controlled pore architecture and the third marker may have a second controlled pore architecture. The first controlled pore architecture may be different from the second controlled pore architecture. The providing step may be carried out with the first controlled pore architecture differing from the second controlled pore architecture with respect to one or more of: pore density, pore shape, pore orientation and pore dimensions, for example. The providing step may be carried out with the first marker being biodegradable. The providing step may be carried out with the first marker including one or more of, for example, a polylactide (PLA), a polyglycolide (PGA), a poly(lactide-co-glycolide) (PLA-PGA), a polyglyconate, a polyanhydride, a lipid, a polysaccharide, and a polyorthoester.

The providing step may be carried out with the first marker having a first shape and with the second marker having a second shape that is different from the first shape. The providing step may be carried out with the device including a third marker configured to be visualized by ultrasound, the third marker being free to move relative to the first and second markers. The providing step may be carried out with the third marker having a different shape than the first marker. The providing step may be carried out with the first marker having a substantially cylindrical shape. The providing step may be carried out with the first marker having a substantially rectangular shape. The providing step may be carried out with the second marker being configured to appear clearly artificial when viewed under X-ray. The providing step may be carried out with the second marker also being to appear clearly artificial when viewed under ultrasound. The providing step may be carried out with the second marker including a non-ferrous metal and optionally including a portion having a paramagnetic property. The providing step may be carried out with the device further a third marker that may be configured to be radiopaque. The third marker may be free to move relative to the first and second markers. The providing step may be carried out with the first and second markers being configured to appear clearly artificial when viewed under ultrasound. The providing step may be carried out with a combination of the first and second markers being configured to appear clearly artificial when viewed under ultrasound.

According to a still further embodiment, the present invention is a soft tissue marker for delivery to a cavity within a patient. The marker may include a plurality of discrete echogenic and biodegradable elements; a radiopaque element disposed adjacent to at least one and external to each of the plurality of discrete echogenic and biodegradable elements, and a biodegradable string coupling at least some of the plurality of discrete echogenic and biodegradable elements.

The biodegradable string may also be coupled to the radiopaque element. The biodegradable string may be or include a biodegradable suture. The biodegradable string may include vycril, for example. Alternatively, the biodegradable string may include collagen, for example. Each of the plurality of discrete echogenic and biodegradable elements may include a porous material that defines surfaces that form interconnected internal voids. Each of the plurality of discrete echogenic and biodegradable elements may be substantially non-swellable (when placed in an aqueous environment, for example).

Another embodiment of the present invention is a soft tissue marker for delivery to a cavity within a patient that may include a plurality of discrete echogenic and biodegradable elements, each of the plurality of discrete echogenic and biodegradable elements defining a longitudinal axis and including at least one of a leading and a trailing surface that is inclined away from a normal to the longitudinal axis, and a radiopaque element disposed adjacent to at least one and external to each of the plurality of discrete echogenic and biodegradable elements.

Each of the plurality of discrete echogenic and biodegradable elements may include a porous material that defines surfaces that form interconnected internal voids. Each of the plurality of discrete echogenic and biodegradable elements may be substantially non-swellable.

A still further embodiment of the present invention is a soft tissue marker for delivery into a cavity within a patient. Such a marker may include a first echogenic and biodegradable element that defines a first plurality of crenellations that define a corresponding first plurality of locally thinner and thicker portions; a second echogenic and biodegradable element that defines a second plurality of crenellations that define a corresponding second plurality of locally thinner and thicker portions, and a radiopaque element disposed adjacent to at least one of the first and second echogenic and biodegradable elements and external to each of the first and second echogenic and biodegradable elements. The locally thinner portions, when the marker is implanted in the cavity, may bend more than the locally thicker portions, thereby imparting a distinctive shape to the first and second echogenic and biodegradable elements within the cavity.

Each of the first and second echogenic and biodegradable elements may include a porous material that defines surfaces that form interconnected internal voids. Each of the first and second echogenic and biodegradable elements may be substantially non-swellable.

BRIEF DESCRIPTION OF THE DRAWINGS

For a further understanding of the objects and advantages of the present invention, reference should be made to the following detailed description, taken in conjunction with the accompanying figures, in which:

FIG. 6A shows further aspects of the exemplary large intact specimen percutaneous biopsy device of FIG. 1 in operation, and illustrates the creation of a cavity within the soft tissue from which the excised specimen was taken.

6B is a cross sectional view of the post treatment cavity of FIG. 6A, taken along cross-sectional line II'.

Figure 1:
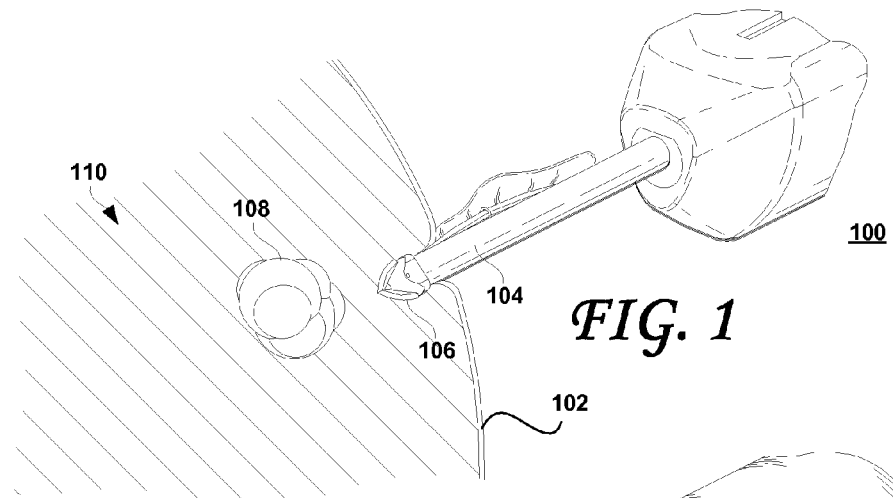
FIG. 1 shows an exemplary large intact specimen percutaneous biopsy device in operation.

FIG. 7 shows further aspects of the exemplary large intact specimen percutaneous biopsy device of FIG. 1 in operation, and further illustrates the creation of a cavity within the soft tissue from which the specimen was taken, with the aforementioned narrow neck or access path connecting the cavity to the skin.

Figure 8:
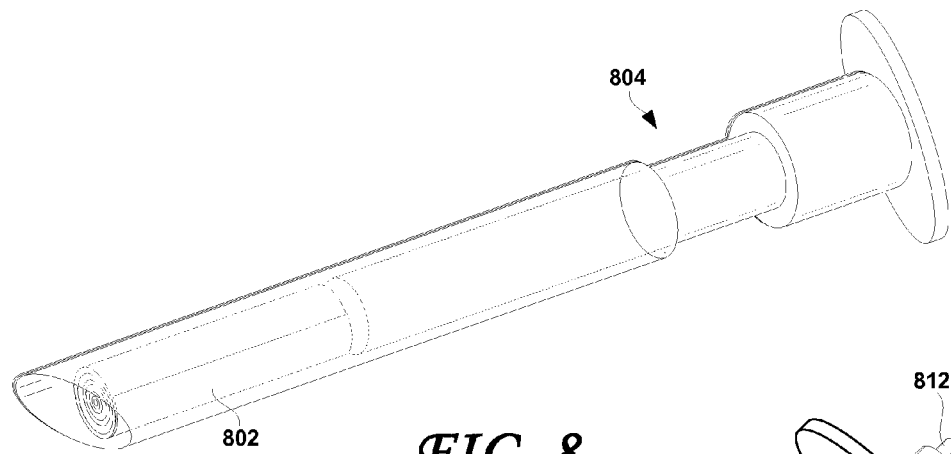

FIG. 8 shows an exemplary delivery device for a post-biopsy cavity treatment implant, according to an embodiment of the present invention.

Figure 9:
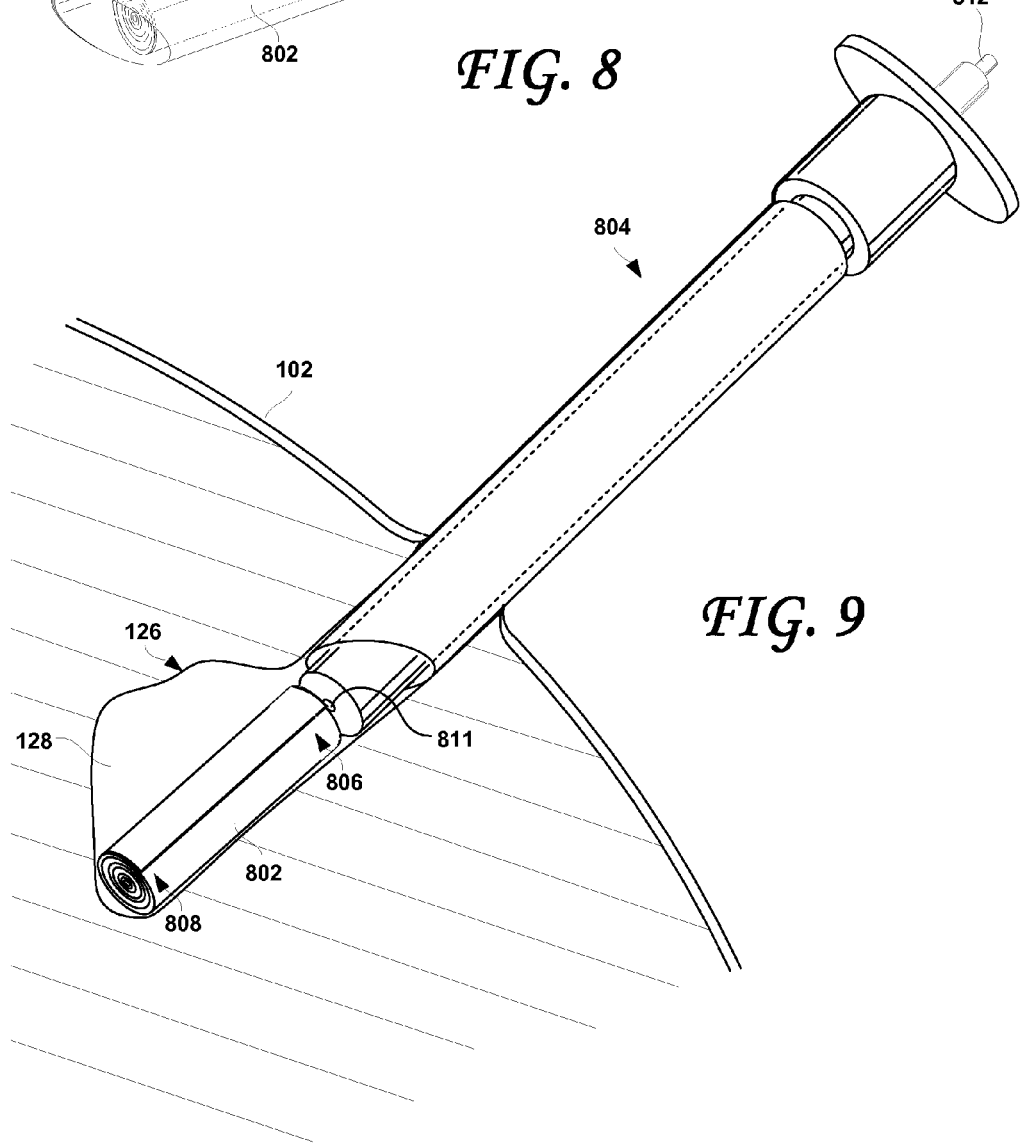

FIG. 9 shows the delivery device of FIG. 8 in operation, delivering a post-biopsy cavity treatment implant according to an embodiment of the present invention within the cavity of FIG. 7.

Figure 10A:
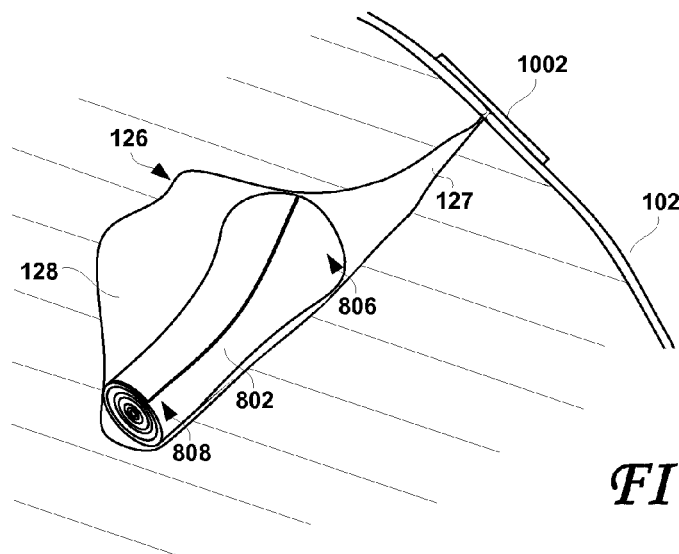

FIG. 10A shows the cavity of FIG. 7, after the implantation of the post-biopsy cavity treatment implant shown in FIGS. 8 and 9, with the percutaneous incision closed.

Figure 10B:
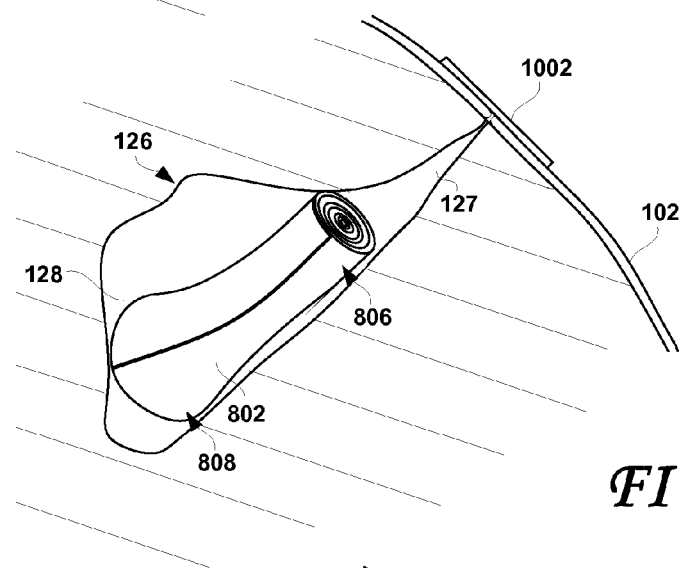

FIG. 10B shows the cavity of FIG. 7, after the implantation of the post-biopsy cavity treatment implant shown in FIGS. 8 and 9 in another orientation, with the percutaneous incision closed.

Figure 10C:
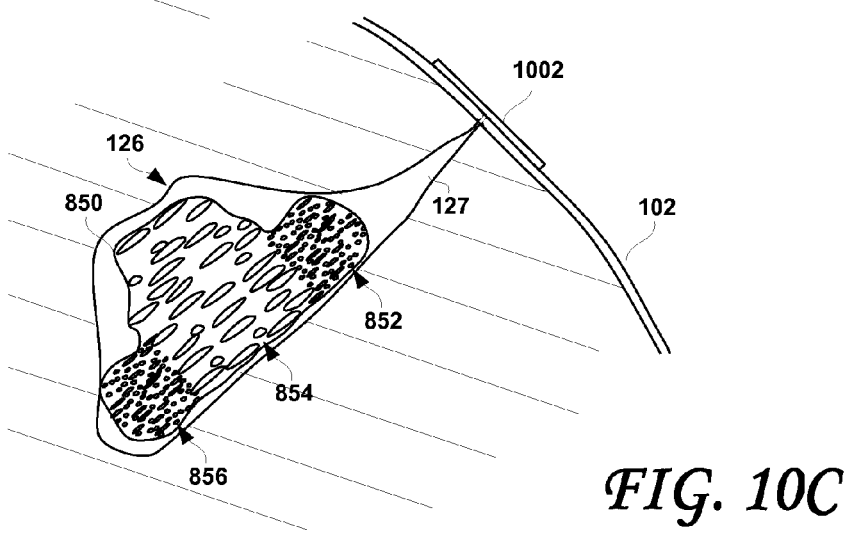

FIG. 10C shows the cavity of FIG. 7, after the implantation of a post-biopsy cavity treatment implant according to another embodiment of the present invention, with the percutaneous incision closed.

Figure 11:
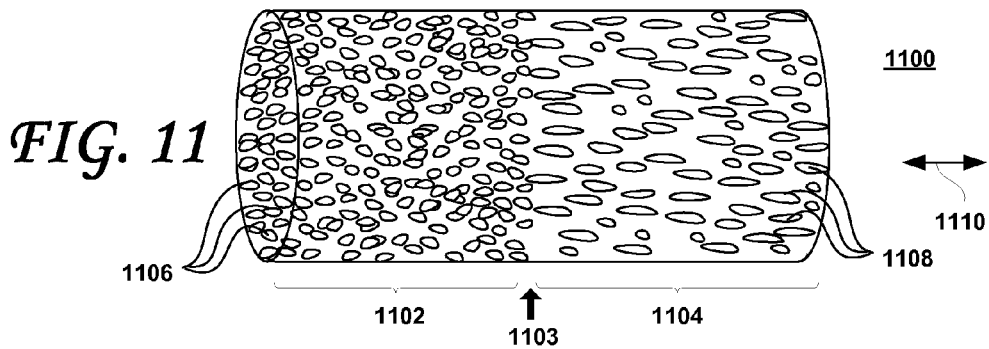

FIG. 11 shows a post-biopsy cavity treatment implant having a predetermined pore architecture, according to an embodiment of the present invention.

Figure 12:
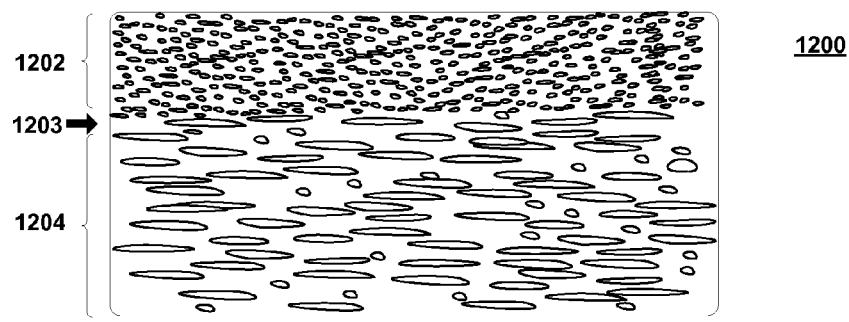

FIG. 12 shows another post-biopsy cavity treatment implant having another predetermined pore architecture, according to another embodiment of the present invention.

Figure 13A:
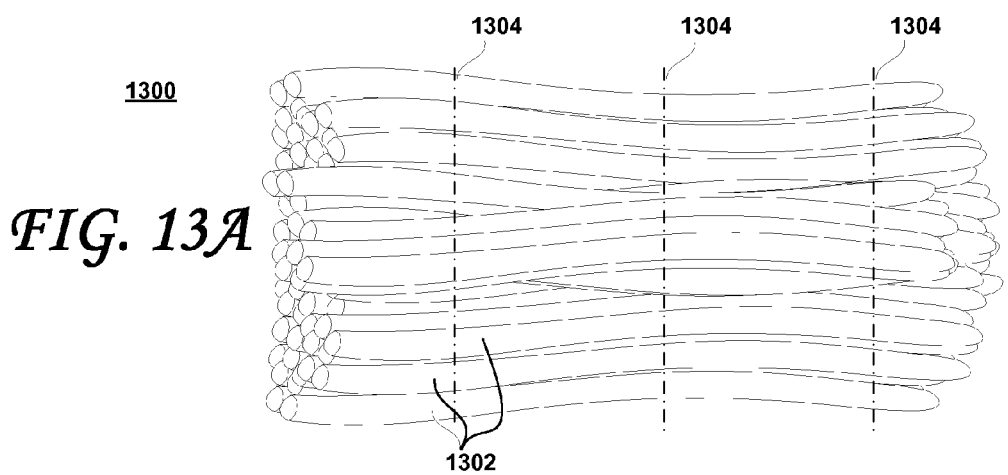

FIG. 13A shows a post-biopsy cavity treatment implant that includes a plurality of fibers, according to another embodiment of the present invention.

Figure 13B:
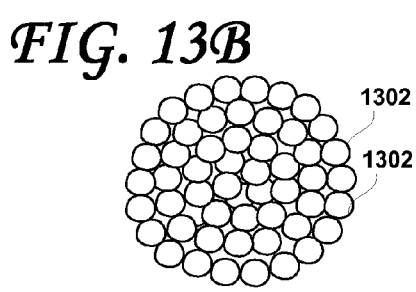

FIG. 13B shows a cross-section of a post-biopsy cavity treatment implant, according to another embodiment of the present invention.

Figure 13C:
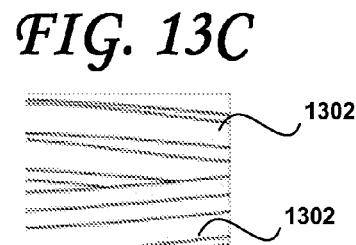

FIG. 13C shows a portion of another post-biopsy cavity treatment implant, according to a further embodiment of the present invention.

Figure 13D:
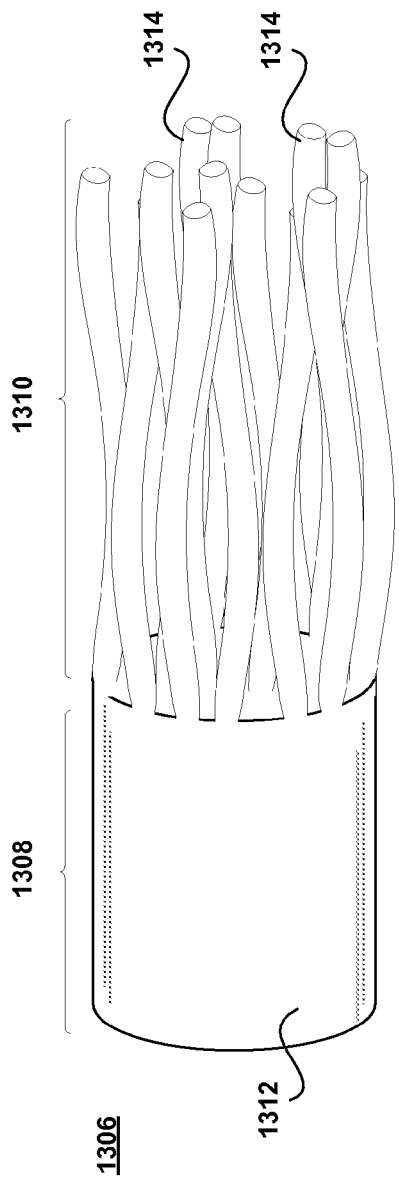

FIG. 13D shows another post-biopsy cavity treatment implant, according to still another embodiment of the present invention.

Figure 13E:
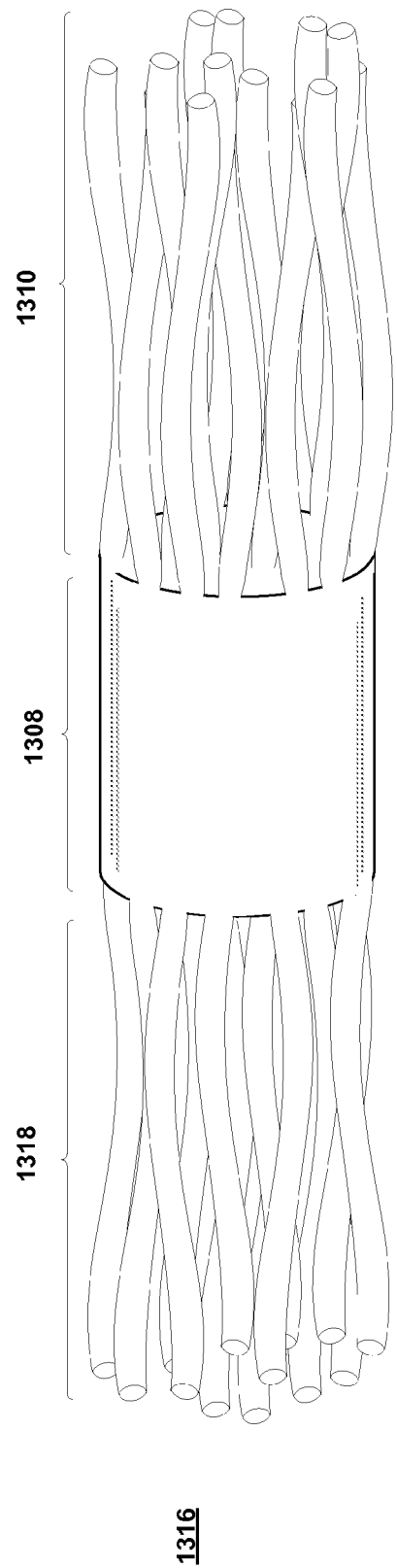

FIG. 13E shows another post-biopsy cavity treatment implant, according to still another embodiment of the present invention.

FIG. 14A shows a post-biopsy cavity treatment implant that includes a plurality of fibers having predetermined pore architectures, according to another embodiment of the present invention.

FIG. 14B shows a front view of a post-biopsy cavity treatment implant, according to another embodiment of the present invention.

FIG. 14C shows a portion of another post-biopsy cavity treatment implant, according to a further embodiment of the present invention.

FIG. 14D illustrates the stacked structure of a post-biopsy cavity treatment implant, according to a further embodiment of the present invention.

FIG. 14E illustrates the stacked structure of another post-biopsy cavity treatment implant, according to a further embodiment of the present invention.

Figure 14F:
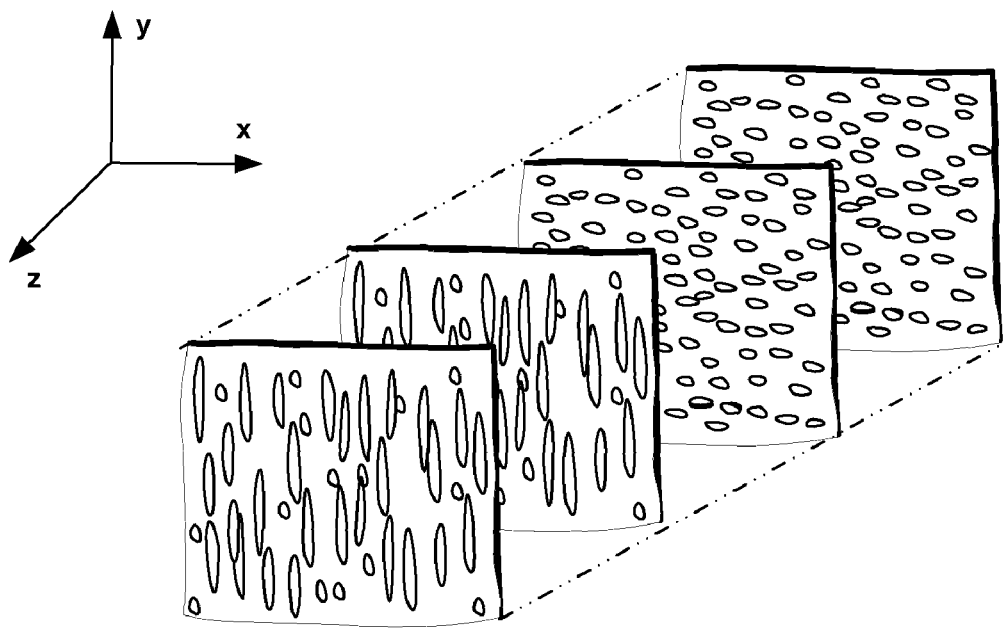

FIG. 14F illustrates the stacked structure of a post-biopsy cavity treatment implant, according to a further embodiment of the present invention.

Figure 14G:
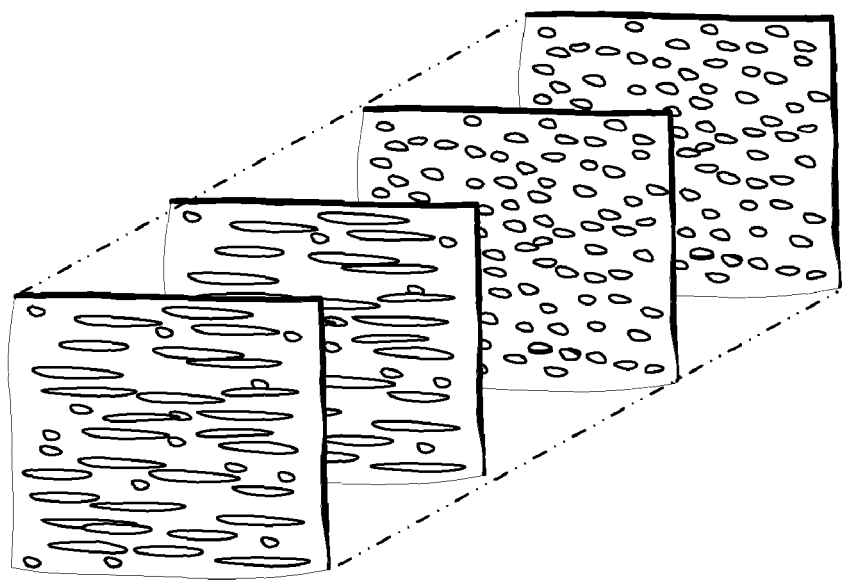

FIG. 14G illustrates the stacked structure of another post-biopsy cavity treatment implant, according to a further embodiment of the present invention.

Figure 15A:
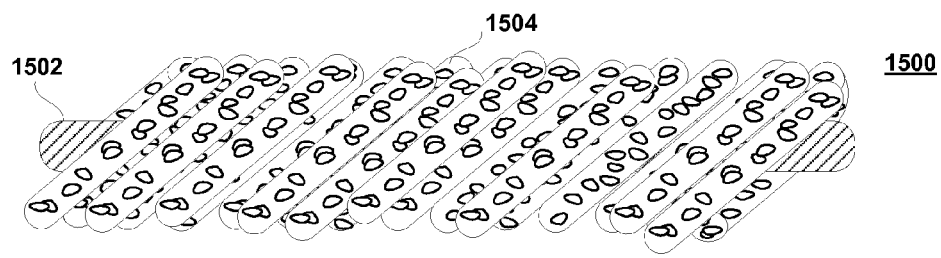

FIG. 15A shows a post-biopsy cavity treatment implant that includes a radiopaque and/or echogenic member around which one or more fibers are wound, according to another embodiment of the present invention.

Figure 15B:
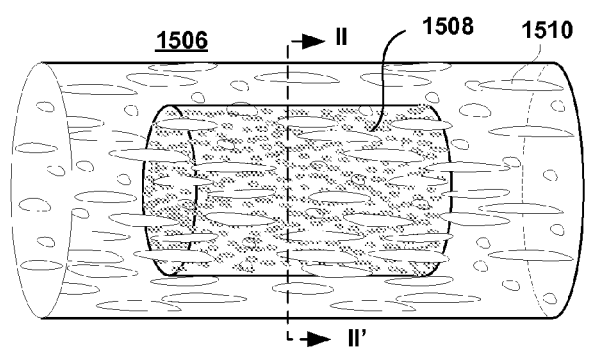

FIG. 15B shows a post-biopsy cavity treatment implant that includes a core portion surrounded by an outer shell portion, each of the core and shell portions having a predetermine core architecture, according to another embodiment of the present invention.

Figure 15C:
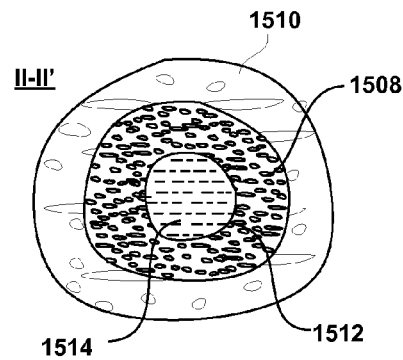

FIG. 15C is a cross-sectional representation of the implant of FIG. 15B, taken along cross-sectional line II-II'.

Figure 15E:
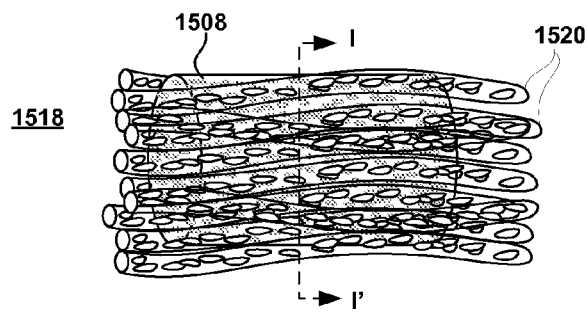
Figure 15D:
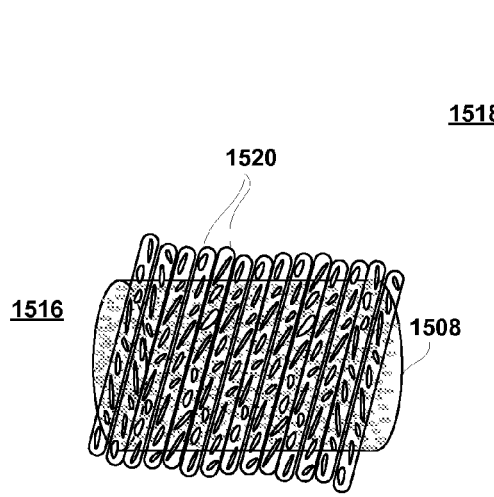

FIG. 15D shows a post-biopsy cavity treatment implant that includes a core portion having a first predetermine core architecture surrounded by an outer shell portion formed by a plurality of wound collagenous fibers having a second predetermined pore architecture, according to another embodiment of the present invention.

FIG. 15E shows a post-biopsy cavity treatment implant that includes a core portion having a first predetermine core architecture surrounded by an outer shell portion formed by a plurality of collagenous fibers having a second predetermined pore architecture, according to another embodiment of the present invention.

Figure 15F:

FIG. 15F is a cross-sectional view of the embodiment of FIG. 15D, taken along cross-sectional line I-I'.

FIG. 16 is a photomicrograph of a collagen matrix having a predetermined pore architecture with post-biopsy cavity treatment implants according to embodiments of the present invention may be constructed.

FIG. 16 is a photomicrograph of a collagen matrix having a predetermined pore architecture with post-biopsy cavity treatment implants according to embodiments of the present invention may be constructed.

FIG. 17 is a photomicrograph of a collagen matrix having another predetermined pore architecture with post-biopsy cavity treatment implants according to embodiments of the present invention may be constructed.

FIG. 18 is a photomicrograph of a collagen matrix having still another predetermined pore architecture with post-biopsy cavity treatment implants according to embodiments of the present invention may be constructed.

FIG. 19 is a photomicrograph of a collagen matrix having a still further predetermined pore architecture with post-biopsy cavity treatment implants according to embodiments of the present invention may be constructed.

FIG. 20 is a photomicrograph of a collagen matrix having yet another predetermined pore architecture with post-biopsy cavity treatment implants according to embodiments of the present invention may be constructed.

Figure 21:
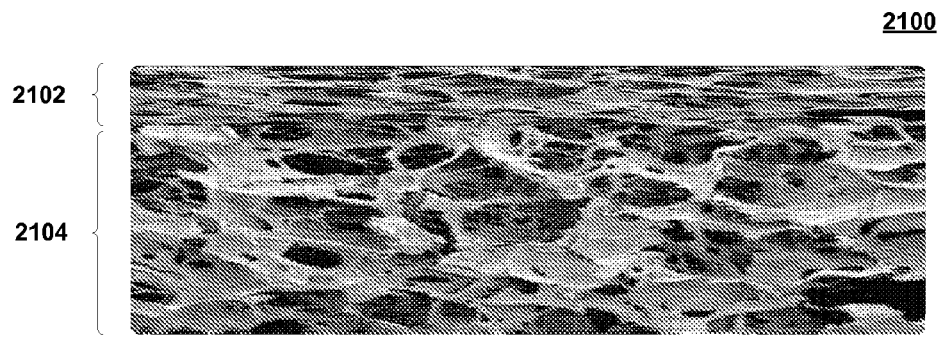

FIG. 21 combination of photomicrographs of collagen matrices illustrating the formation of a stacked laminate structure including a first layer having a first predetermined pore architecture and a second layer having a second predetermined pore structure, according to an embodiment of the present invention.

Figure 22:

FIG. 22 is a combination of photomicrographs of collagen matrices that collectively illustrate a post-biopsy cavity treatment implant having a predetermined pore density gradient and/or predetermined graduated crosslinking gradient, according to a further embodiment of the present invention.

Figure 23:
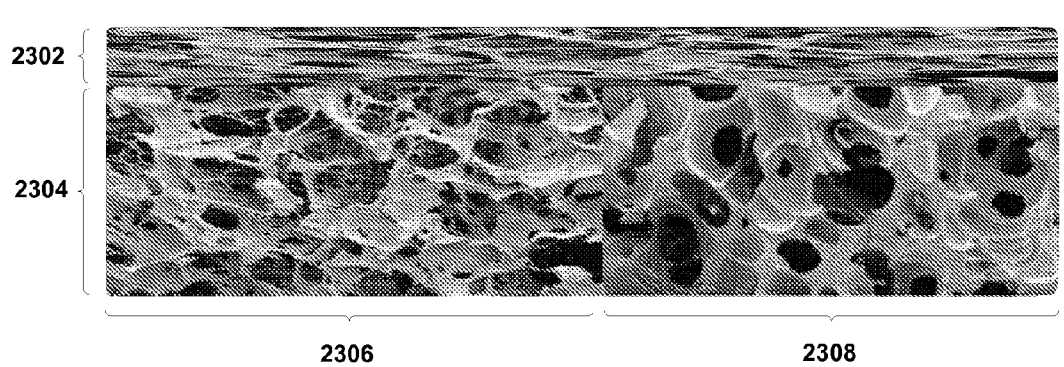

FIG. 23 is a combination of photomicrographs of collagen matrices that collectively illustrate a post-biopsy cavity treatment implant according to another embodiment of the present invention.

Figure 24:
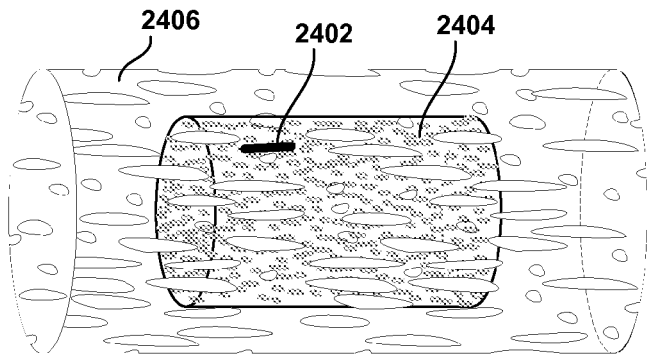

FIG. 24 shows a post-biopsy cavity treatment implant that includes a core portion surrounded by an outer shell portion, the core portion including a radiopaque element and the core and shell portions having mutually different and predetermined pore architectures, according to another embodiment of the present invention.

Figure 25:
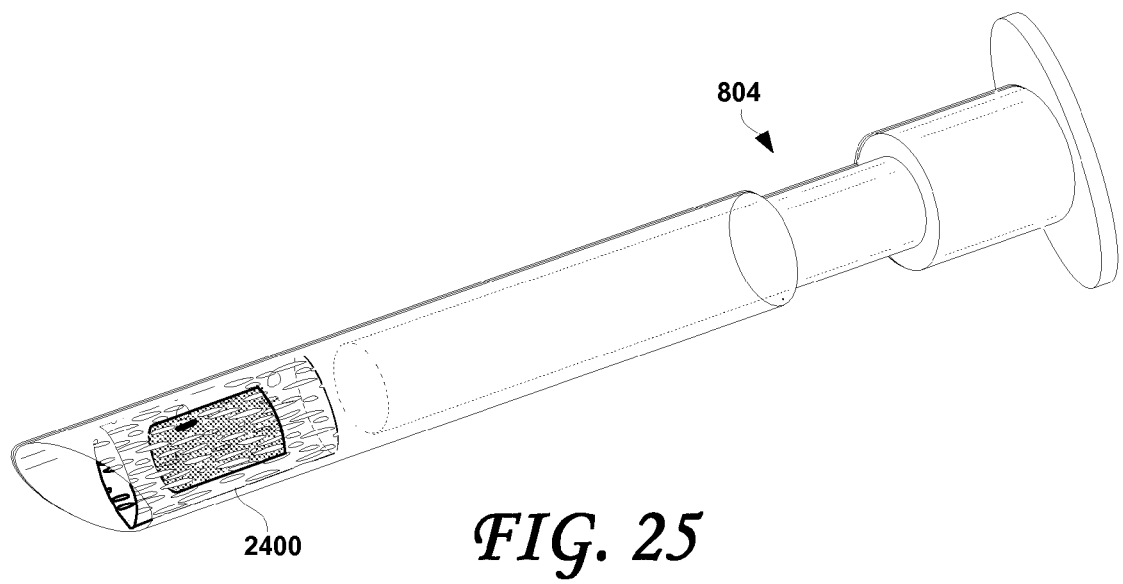

FIG. 25 shows the post-biopsy cavity treatment implant of FIG. 24 loaded into an exemplary delivery device, according to an embodiment of the present invention.

Figure 26:
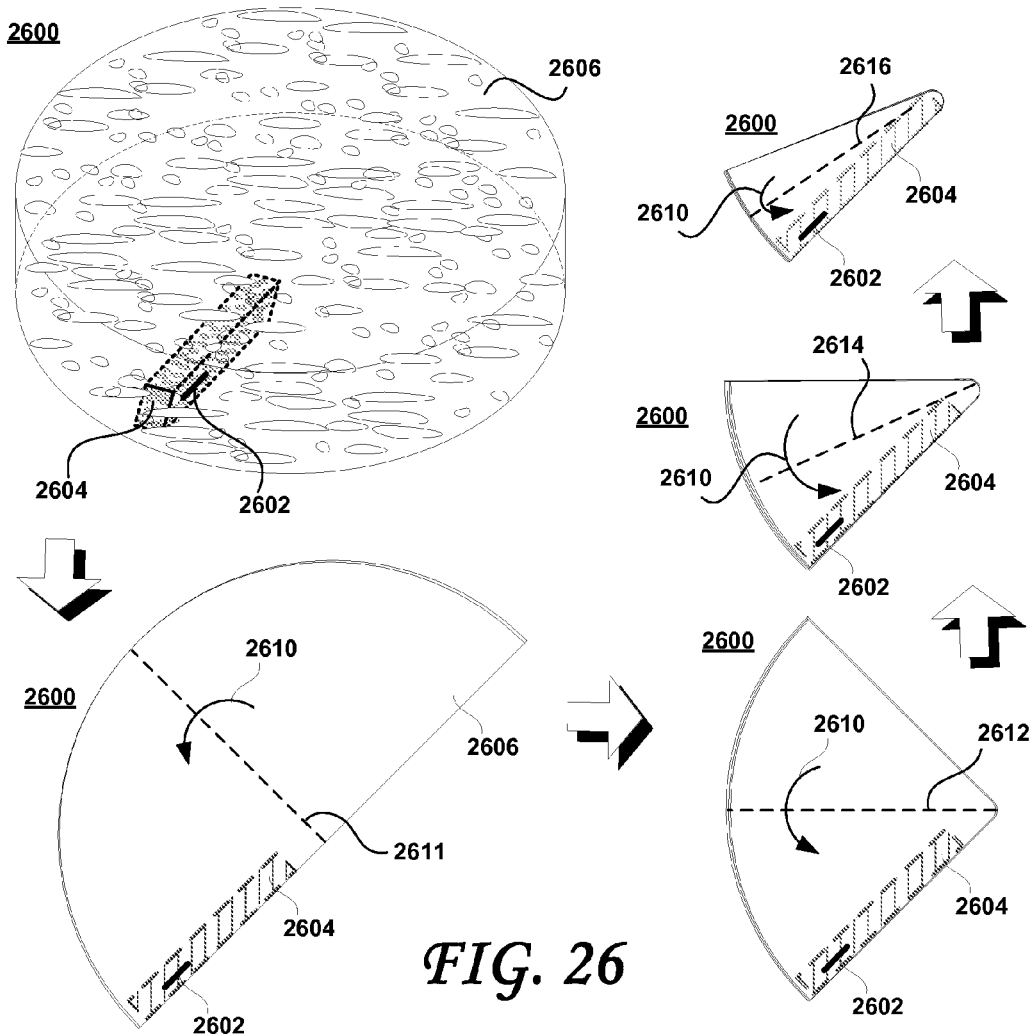

FIG. 26 shows a post-biopsy cavity treatment implant according to a still further embodiment of the present invention, in various stages of manufacture.

Figure 27:
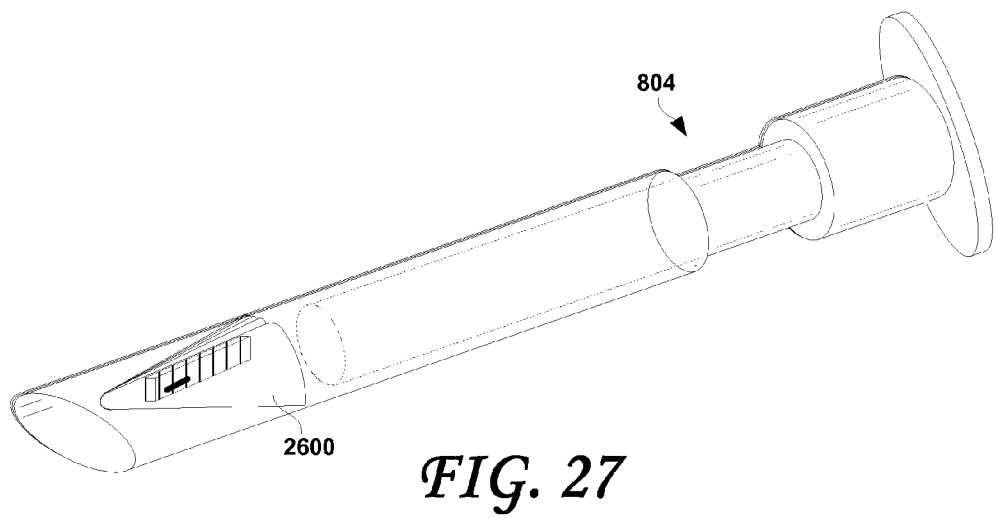

FIG. 27 shows the post-biopsy cavity treatment implant of FIG. 26 loaded into an exemplary delivery device, according to an embodiment of the present invention.

Figure 28:
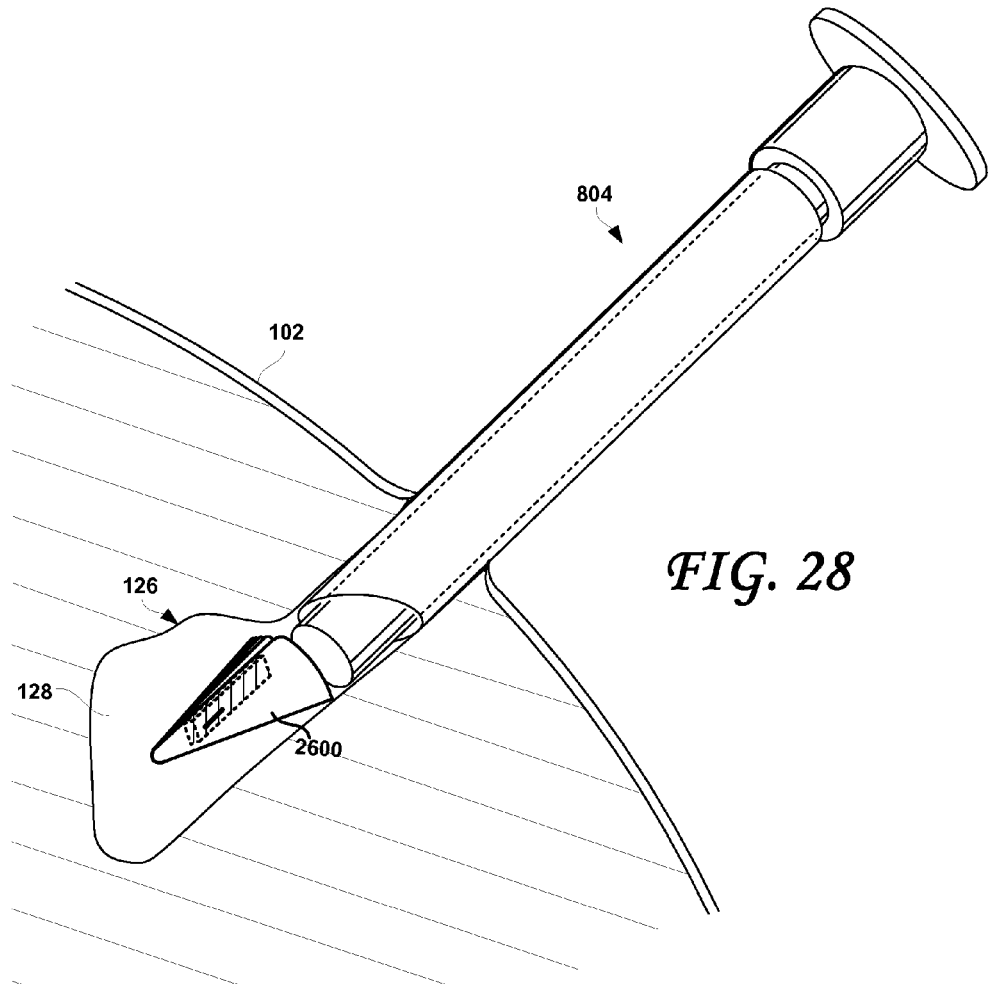

FIG. 28 shows the post-biopsy cavity treatment implant of FIGS. 26 and 27 during implantation, according to an embodiment of the present invention.

Figure 29:
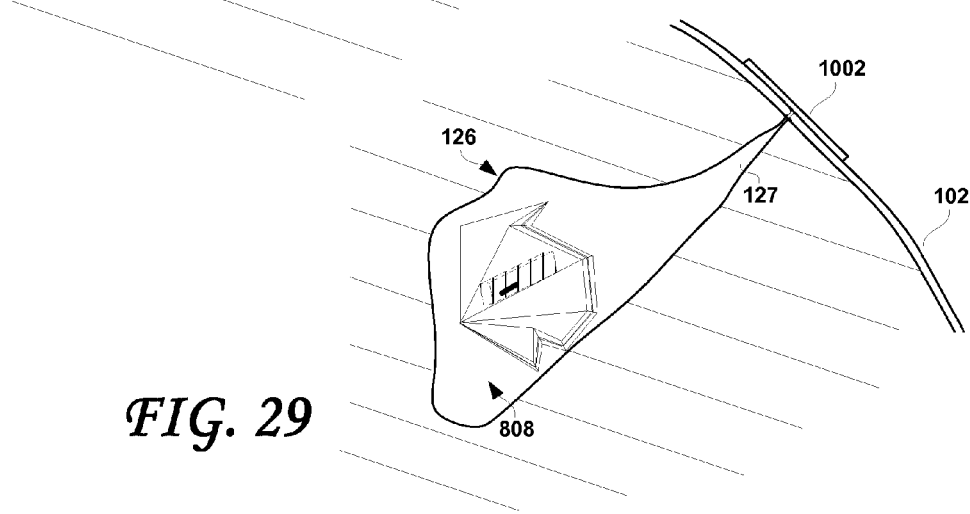

FIG. 29 shows the post-biopsy cavity treatment implant of FIG. 28 after implantation, illustrating the manner in which the implant may expand and/or unfold within the cavity after implantation, according to an embodiment of the present invention.

Figure 30:
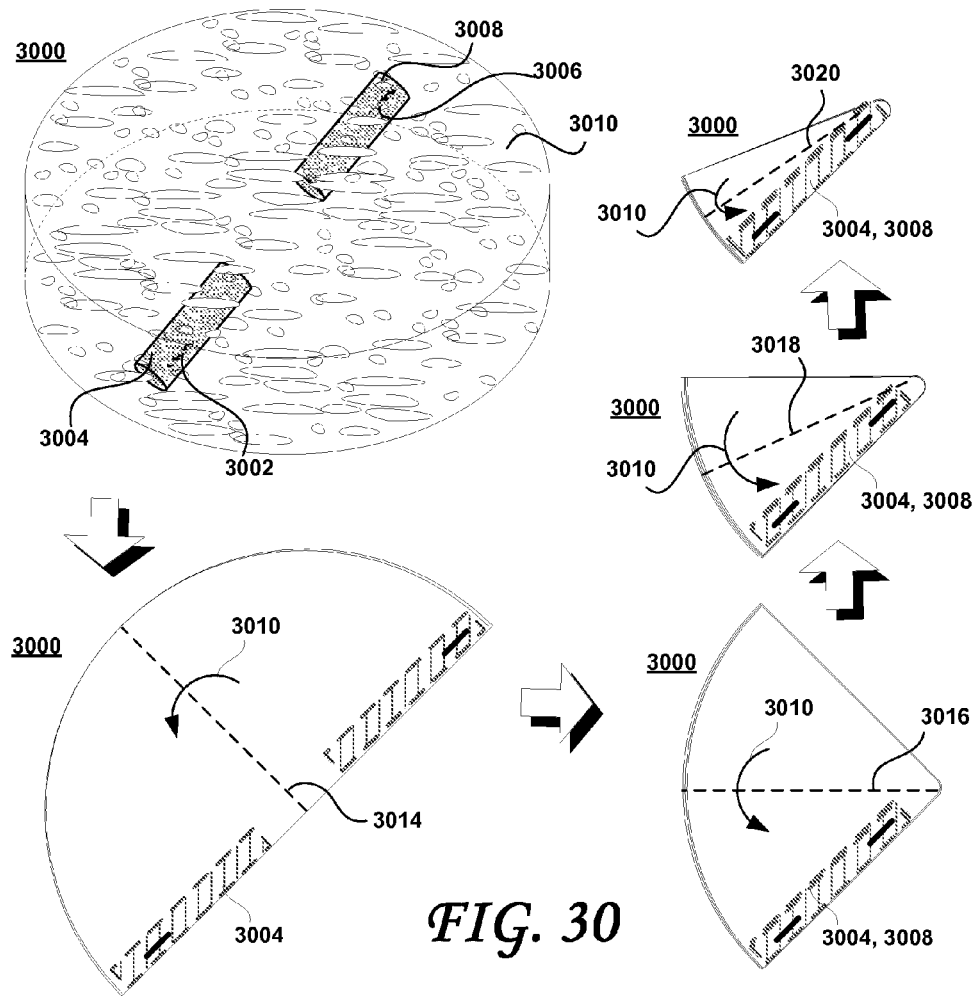

FIG. 30 shows a post-biopsy cavity treatment implant according to another embodiment of the present invention, in various stages of manufacture.

Figure 31:
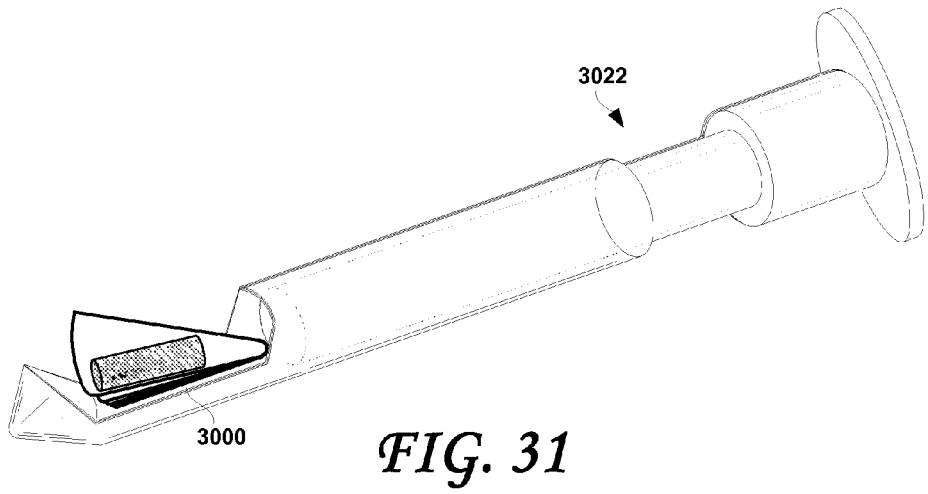

FIG. 31 shows the post-biopsy cavity treatment implant of FIG. 30 loaded into an exemplary delivery device, according to an embodiment of the present invention.

Figure 32:
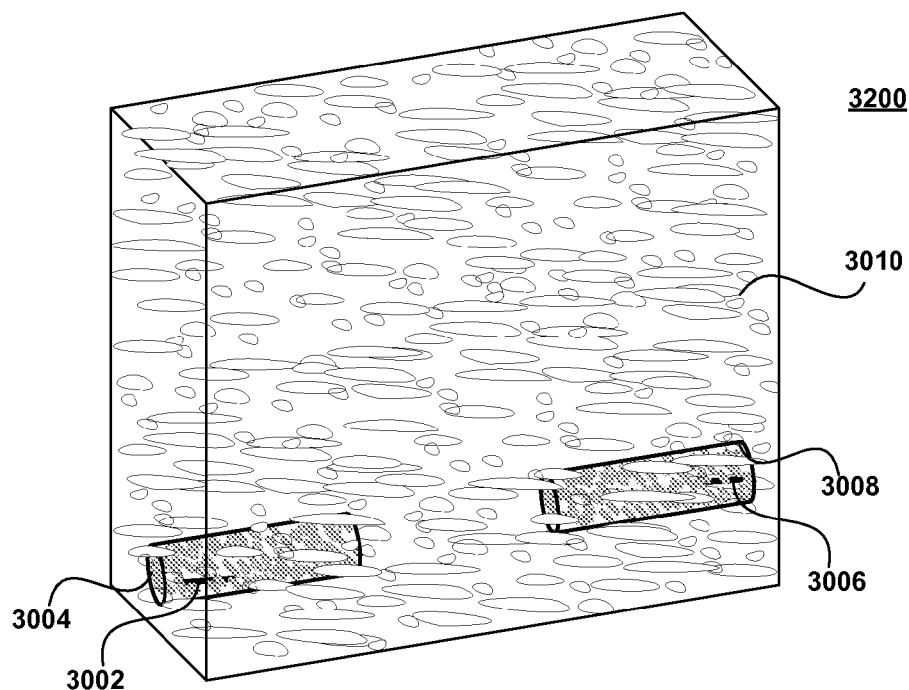

FIG. 32 shows a post-biopsy cavity treatment implant according to yet another embodiment of the present invention, in a configuration prior to folding and/or compression.

Figure 33:
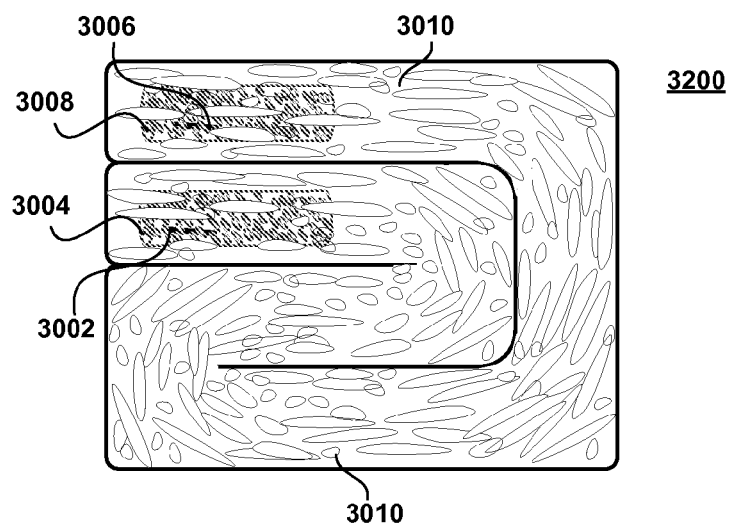

FIG. 33 shows the post-biopsy cavity treatment implant of FIG. 32 in one of many possible folded configurations, according to still another embodiment of the present invention.

Figure 34:
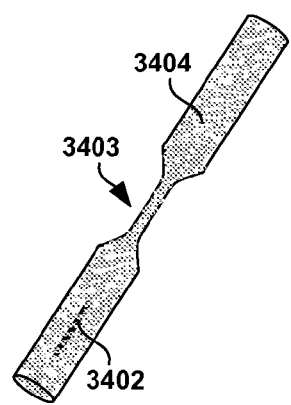

FIG. 34 shows a core portion suitable for use in conjunction with the present post-biopsy cavity treatment implant, according to another embodiment of the present invention.

Figure 35:
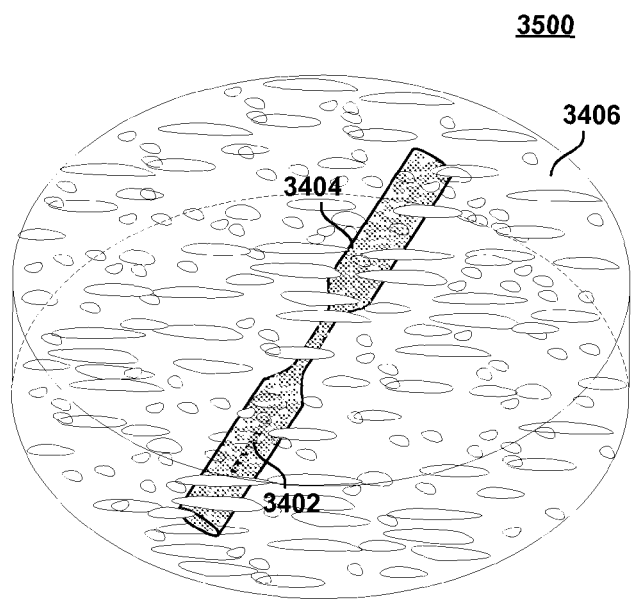

FIG. 35 shows a post-biopsy cavity treatment implant incorporating the core portion of FIG. 34, according to yet another embodiment of the present invention, in a configuration prior to folding and/or compression.

Figure 36:
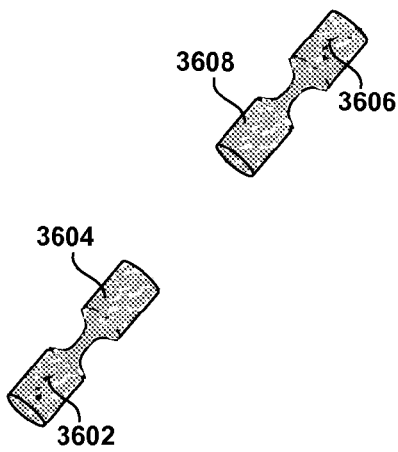

FIG. 36 shows further core portions suitable for use in conjunction with the present post-biopsy cavity treatment implant, according to another embodiment of the present invention.

Figure 37:
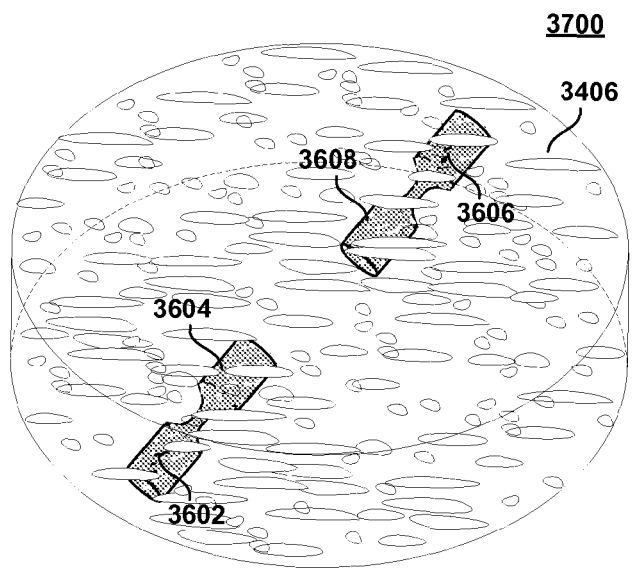

FIG. 37 shows a post-biopsy cavity treatment implant incorporating the core portions of FIG. 36, according to a further embodiment of the present invention, in a configuration prior to folding and/or compression.

Figure 38:
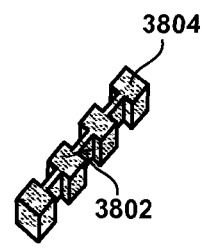

FIG. 38 shows another core portion suitable for use in conjunction with the present post-biopsy cavity treatment implant, according to another embodiment of the present invention.

Figures 39, 40:

FIG. 39 shows an exemplary radiopaque element suitable for use in conjunction with the present post-biopsy cavity treatment implant, according to a still further embodiment of the present invention.

FIG. 40 shows another radiopaque element suitable for use in conjunction with the present post-biopsy cavity treatment implant, according to yet another embodiment of the present invention.

Figure 41:
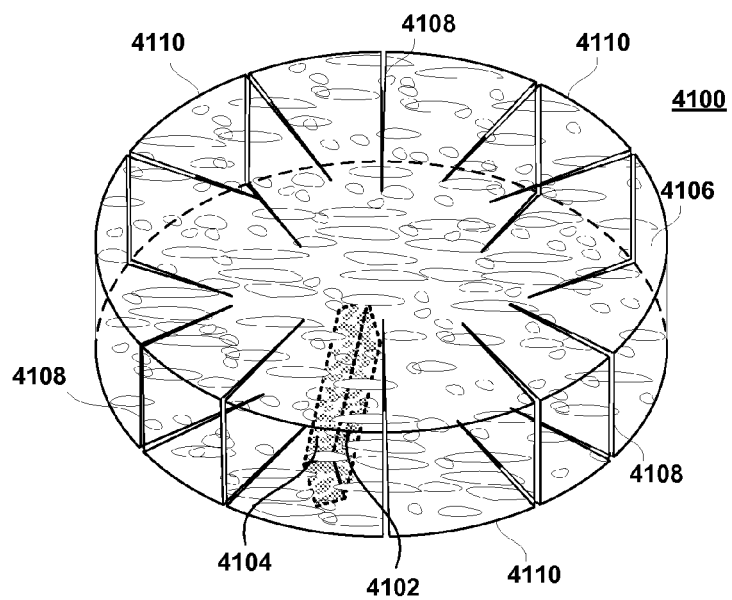

FIG. 41 shows a post-biopsy cavity treatment implant, according to a further embodiment of the present invention, in a configuration prior to folding and/or compression.

Figure 42:
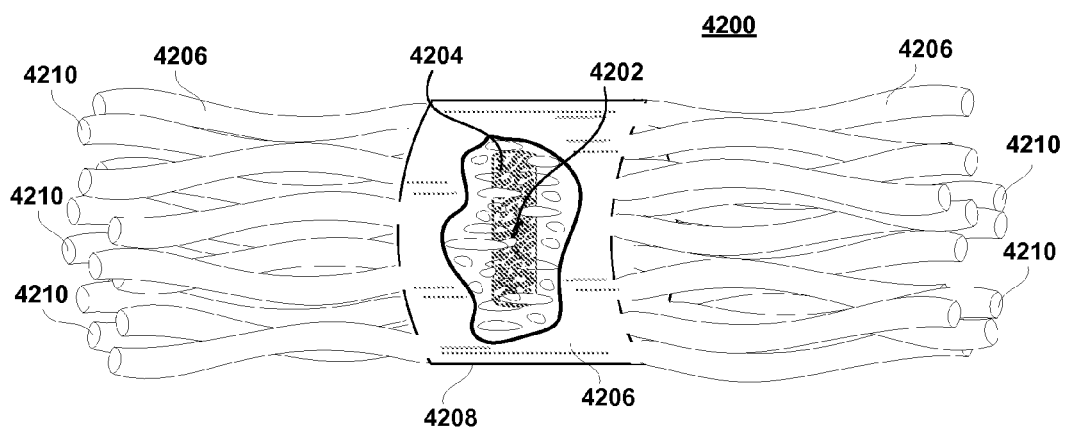

FIG. 42 shows a post-biopsy cavity treatment implant, according to another embodiment of the present invention, in a configuration prior to folding and/or compression.

FIG. 43 shows a soft tissue marker, according to an embodiment of the present invention.

FIG. 44 shows a device to deliver a soft tissue marker, according to an embodiment of the present invention.

Figure 45:
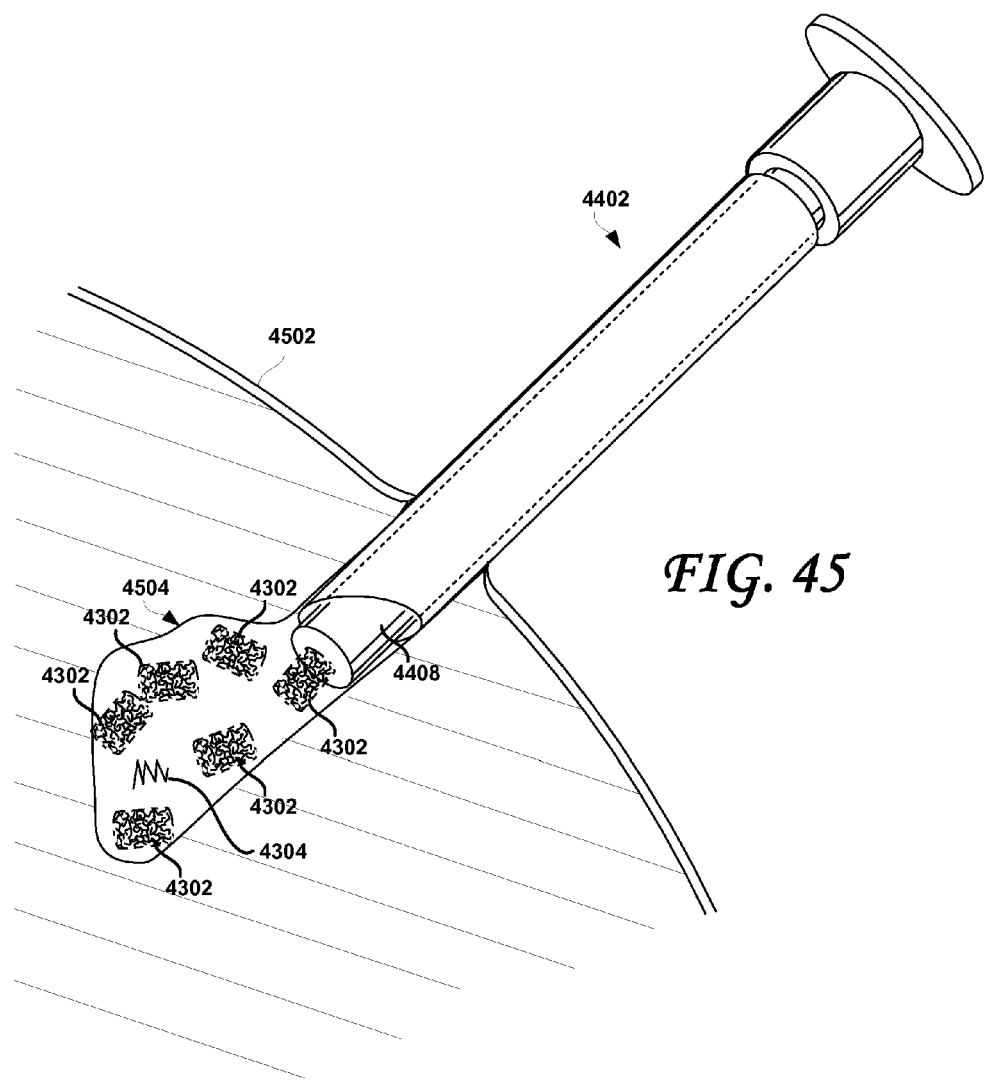

FIG. 45 shows aspects of a method of marking a cavity in a breast for subsequent visualization, according to an embodiment of the present invention.

FIG. 46 shows a soft tissue marker, according to another embodiment of the present invention.

FIG. 47 shows another soft tissue marker, according to another embodiment of the present invention.

FIG. 48 shows another soft tissue marker, according to a further embodiment of the present invention.

Figure 49:
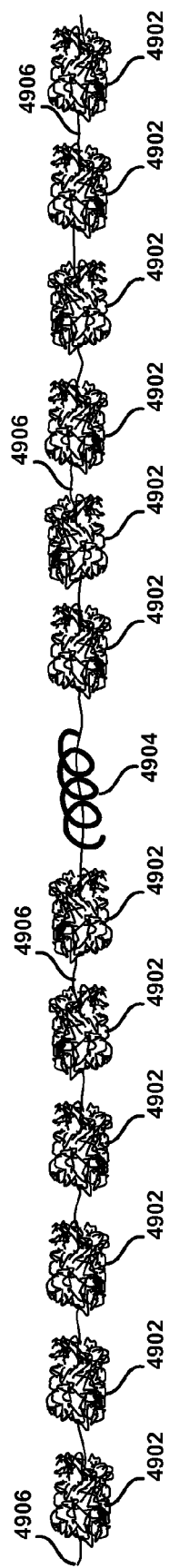

FIG. 49 shows another soft tissue marker, according to an embodiment of the present invention.

Figure 50:
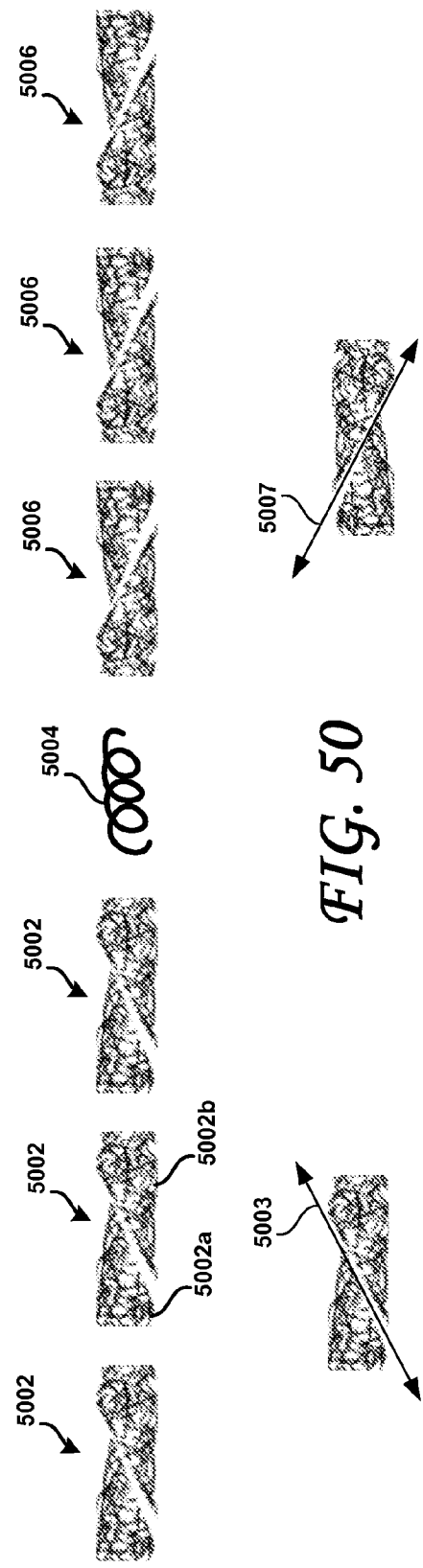

FIG. 50 shows yet another soft tissue marker, according to an embodiment of the present invention.

FIG. 51 shows a still further soft tissue marker, according to another embodiment of the present invention, shown in simplified cross-section.

FIG. 52 shows the distal portion of a soft tissue marker introducer or applicator, with the soft tissue marker of FIG. 51 being deployed at a biopsy site.

FIG. 53 shows a portion of the soft tissue marker of FIG. 51, in a deployed configuration.

FIG. 54 shows a still further soft tissue marker, according to yet another embodiment of the present invention, shown in simplified cross-section.

FIG. 55A shows the soft tissue marker of FIG. 54, shown loaded into an applicator for deployment within a soft tissue cavity.

FIG. 55B shows the soft tissue marker of FIG. 54, shown in an exemplary deployed configuration.

DESCRIPTION OF EMBODIMENTS OF THE INVENTION

FIGS. 1-7 show aspects of a percutaneous method for cutting, collecting and isolating a tissue specimen and the subsequent creation of a cavity within which embodiments of the present inventions may be implanted. The excisional device shown in FIGS. 1-7 is described in commonly assigned U.S. Pat. No. 6,022,362, and in copending and commonly assigned application Ser. No. 10/189,277, filed on Jul. 3, 2002, the disclosure of each being incorporated herein in its entirety. Although embodiments of the present invention are described relative to a cavity created by the excisional device shown in FIGS. 1-7, it is to be understood that the present inventions are not to be limited thereby. Indeed, embodiments of the present invention may be advantageously utilized to treat cavities of various shapes and sizes created by other devices, including devices that obtain tissue specimen through coring or ablation techniques, for example.

Figure 2:
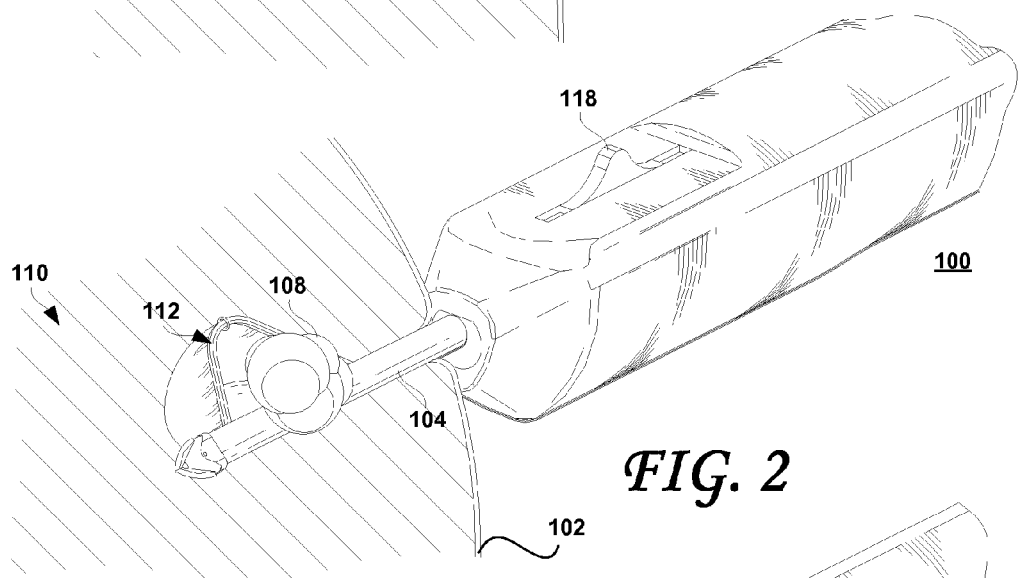
FIG. 2 shows further aspects of the exemplary large intact specimen percutaneous biopsy device of FIG. 1 in operation.
Figure 3:
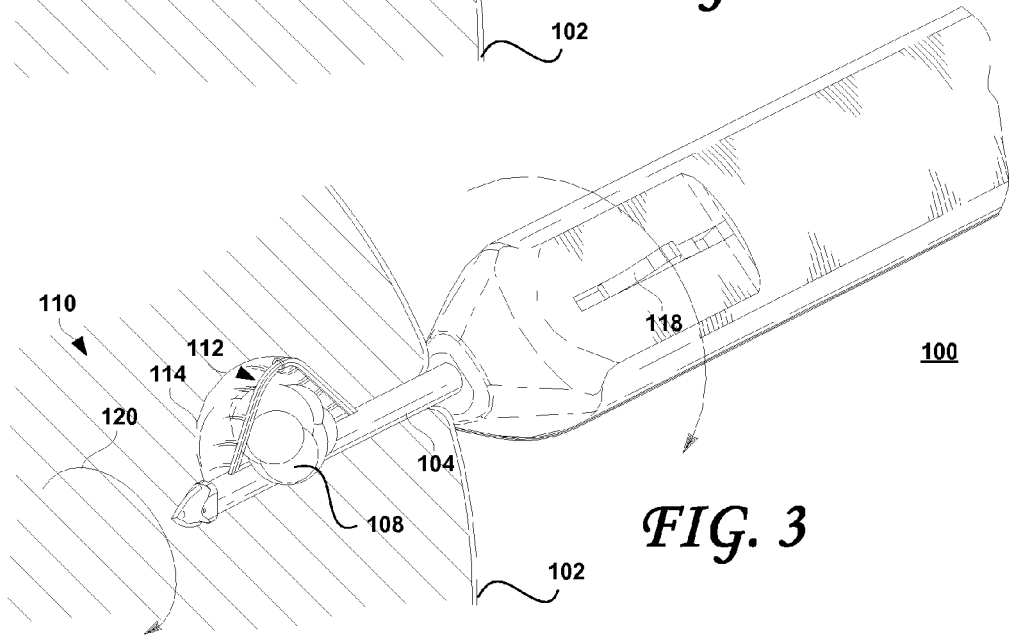
FIG. 3 shows further aspects of the exemplary large intact specimen percutaneous biopsy device of FIG. 1 in operation.
Figure 4:
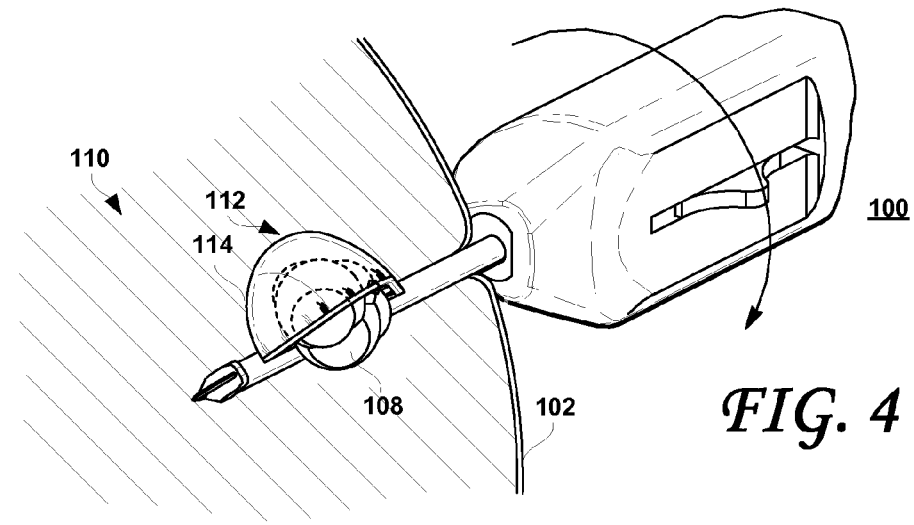
FIG. 4 shows still further aspects of the exemplary large intact specimen percutaneous biopsy device of FIG. 1 in operation.
Figure 5:
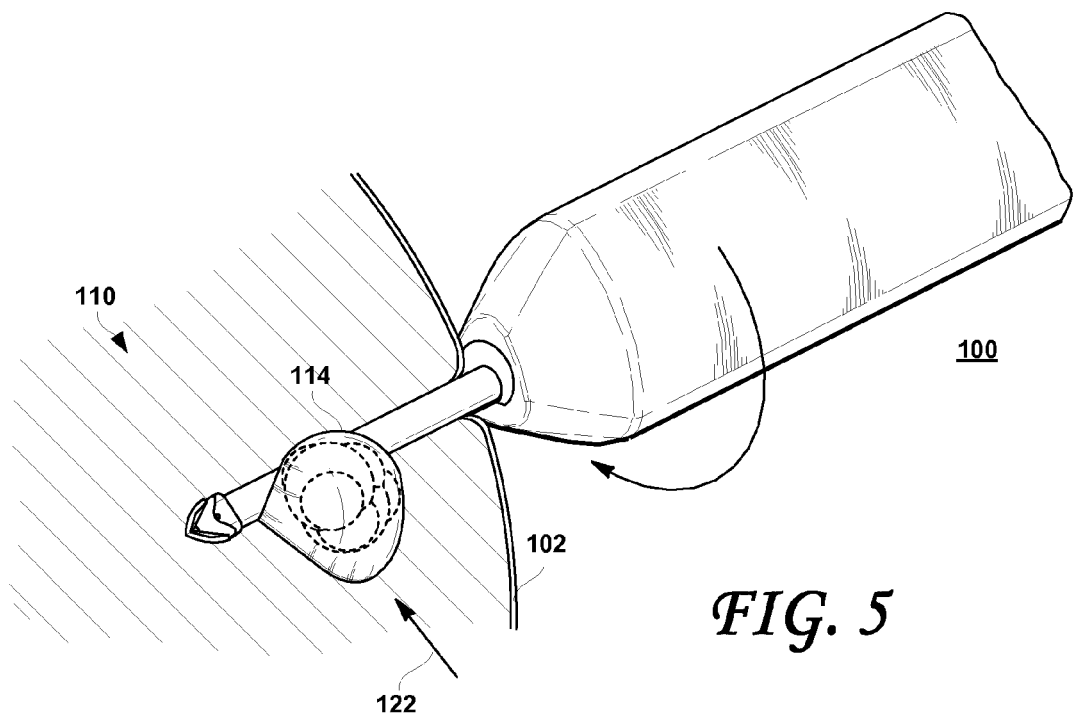
FIG. 5 shows further aspects of the exemplary large intact specimen percutaneous biopsy device of FIG. 1 in operation.

As shown in FIG. 1, the excisional device 100 is introduced into a mass of tissue 110 through the skin 102, with the integrated cut and collect assembly 112 thereof in a retracted position. The device 100 is then advanced such that the assembly 112 is adjacent to the target lesion 108. The assembly 112 may then be energized and expanded as shown in FIG. 2 by acting upon the actuator 118. As the assembly 112 is RF energized and expanded, it cuts the tissue through which it travels. As shown at FIG. 3, the excisional device 100 may then be rotated, while the assembly 112 remains energized, causing the leading edge thereof to cut through the tissue, preferably with clean margins. The expanded integrated cut and collect assembly 112 deploys the membrane 114 and the cut specimen 108 is collected in the open bag formed by the close-ended deployed flexible membrane 114. As shown in FIGS. 4 and 5, the rotation of the device 100 may then be continued as needed, preferably under ultrasonic guidance. To fully sever the specimen 108 from the surrounding tissue 110, the assembly 112, while still energized, is retracted to capture, encapsulate and isolate the specimen 108 within the flexible membrane 114. As shown in FIG. 6A, the specimen 108 may then be recovered by retracting the device 100 through the retraction path 127, stretching it as necessary. FIG. 7 shows a fully retracted device 100, containing a collected and isolated specimen 108.

As shown in FIGS. 6A-7, after the procedure described above or after any procedure in which a substantial volume of tissue specimen is taken, a void or cavity 126 is created where the tissue specimen 108 used to be. Cavities as shown at 126 may require different post procedural treatments, as compared to procedures such as needle biopsies due to the different nature, size and shape created by the biopsy device. As shown in FIGS. 6A and 6B, the exemplary cavity 126 is characterized by a relatively narrow access path 127 that emerges into a larger cavity chamber 128 formed by the extension and rotation of the cut and collect assembly 112 during the above-described procedure. After the device 100 is withdrawn from the patient as shown in FIG. 7, portions of the cavity 126 and/or access path 127 may settle and collapse somewhat, as the interior tissue walls defining the cavity 126 are no longer supported by the tissue previously occupying that space.

Treating the post-biopsy cavity 126 is desirable for a variety of reasons. One such reason is to accommodate the unique size and shape of the cavity 126 created by the device 100. It is desirable to influence and/or promote the healing process of the cavity, and to do so in a predictable manner. One aspect of influencing the healing process of the cavity 126 is promoting the growth of new connective tissue within the cavity 126 in a predictable manner. Indeed, it is desirable to influence and promote both tissue ingrowth within the cavity and to influence the formation of hematomas and seromas. Another reason for treating the post-biopsy cavity 126 is to modify it in such a manner as to render it recognizable immediately and preferably long after the procedure that created the cavity 126. The cavity 126, left untreated, may be visible under ultrasound. However, that may not be the case and it is believed to be desirable to at least partially fill the cavity 126 with a cavity treatment implant that will render the cavity 126 clearly visible under various imaging modalities, including modalities such as ultrasound, X-ray, MRI, elastography, microwave and the unaided eye, for example. Such visibility may be due to the structure of a cavity treatment implant or devices implanted within the cavity and/or a recognizable pattern of tissue ingrowth caused or influenced by the continuing or past presence of post-biopsy cavity treatment implants disclosed herein. Other desirable attributes of embodiments of the implantable post-biopsy cavity treatment implant of the present invention include hemostasis, and the ability to deliver one or more therapeutic agents to the patient at the post-biopsy cavity treatment implant site such as, for example, lido/epi, Non-Steroidal Anti-Inflammatory Drugs (NSAIDS), tissue growth factors, anti-neoplastic medications (to name a few) or combinations of the above and/or others. Filling the cavity 126 may have other benefits, including cosmetic. Indeed, filling the cavity and promoting a smooth, gradual, recognizable and orderly tissue ingrowth pattern may prevent dimpling, skin depressions and the like sometimes associated with the removal of a large intact specimen during the biopsy procedure. Embodiments of the present invention may also find utility in augmentation or reconstructive procedures for the breast or other soft tissue.

According to an embodiment of the present invention, the post-biopsy cavity treatment implant may have a size and a shape that at least partially fills the cavity. Advantageously, the present post-biopsy cavity treatment implant, after insertion, may have a characteristic shape that is readily perceptible and recognizable through various modalities, including, for example, ultrasound, X-ray or MRI. The shape of the present post-biopsy cavity treatment implant may also influence the manner in which tissue growths therein. Preferably, embodiments of the present post-biopsy cavity treatment implant should be shaped and dimensioned so as to uniquely accommodate the size and shape of the cavity 126 created by the device 100 of FIGS. 1-7. However, embodiments of the present invention may be readily sized and shaped to specifically accommodate cavities of any shape and size created by other devices and/or biopsy or therapeutic surgical procedures.

According to an embodiment thereof, the present invention may include an implantable post-biopsy cavity treatment implant having one or more of the structures, characteristic and properties described herein. As shown in FIG. 8, the implantable post-biopsy cavity treatment implant 802, in a pre-implanted state, may be loaded into an introducer, an illustrative example of which is shown at reference numeral 804. The introducer 804 may then be inserted into the tissue 110 through the access path 127 and at least partially into the cavity chamber 128 of the cavity 126. The post-biopsy cavity treatment implant 802 may then be delivered to the cavity 126 and thereafter be left in place and the introducer 804 withdrawn. The pre-implanted state of the post-biopsy cavity treatment implant 802 is preferably a state in which the post-biopsy cavity treatment implant occupies its minimum volume. According to an embodiment of the present invention, the pre-implanted state of the post-biopsy cavity treatment implant 802 is an at least partially lyophilized (e.g., at least partially dehydrated) state and the post-biopsy cavity treatment implant may be configured to swell when placed within a biological fluid environment such as the cavity 126. The post-biopsy cavity treatment implant 802 may define a proximal portion 806 that is closest to the access path 127 and a distal portion 808 that is relatively further away from the access path 127 than is the proximal portion 806.

Whereas FIG. 9 shows the present post-biopsy cavity treatment implant 802 immediately after implantation in tissue (i.e., still in a state in which it occupies its minimum volume), FIG. 10A shows the state of the present post-biopsy cavity treatment implant 802 a short period of time after implantation. As shown, the post-biopsy cavity treatment implant 802 is no longer in its pre-implanted state. Indeed, the post-biopsy cavity treatment implant 802, having been placed in a biological fluid environment (such as the patient's tissue), begins to swell. According to an embodiment of the present invention, the post-cavity treatment implant 802 may be configured to swell in a uniform manner. In another example, the surgeon may inject fluids after placing the device with the intent to "wet" the present post-cavity treatment implant. Substances such as saline, fibrin solution or other catalyst or activator may be used for that purpose. The activator or swelling fluid could be injected preferentially at the proximal portion 806 or selectively at points in the post-cavity treatment implant to cause it to secure itself in position inside the cavity 126. Alternatively, as part of the insertion device (such as, for example, the introducer 804), an integral vial may be crushed by the surgeon to release the activating fluid (for example, an aqueous solution, dye/pigment) in the area of the proximal portion 806 for example, thus causing rapid swelling of that region. Alternately, the introducer 804 may define an internal lumen 811 over its length and may include a fluid injection port 812 at the proximal end of the device. Fluids such as the aforementioned saline or fibrin may then be introduced into the cavity 126 through the fluid injection port 812 and the internal lumen 811 to cause the rapid swelling of the implant or for any other reason. Delivering such fluids can be especially useful if the field within the cavity is relatively dry as can occur in the ideal case. According to another embodiment of the present invention, the post-biopsy cavity treatment implant 802 may be configured to swell non-uniformly. Such non-uniform swelling rates may be advantageous in insuring that the post-biopsy cavity treatment implant 802 stays where it is placed during the implantation procedure. In the embodiment shown in FIG. 10A, the post-biopsy cavity treatment implant 802 is structured such that the rate at which the proximal portion 806 swells faster than the rate at which the distal portion 808 swells. When implanted in a cavity 126 such as shown in FIGS. 6A, 6B, 7, 9 and 10, the proximal portion 806 swells faster than the distal portion 808, thereby serving to maintain the post-biopsy cavity treatment implant 802 within the cavity chamber 128 of the cavity 126. This may be achieved by, for example, controlling the crosslinking densities or creating a gradient of crosslinking densities within the post-biopsy cavity treatment implant 802, where certain regions of the post-biopsy cavity treatment implant 802 are controlled to have a greater crosslinking density than other regions, resulting in a non-uniform swelling pattern over the extent of the device 802. For example, the distal portion 808 may be configured to be relatively more crosslinked than the proximal portion 806 thereof, resulting in the proximal portion 806 swelling more and/or faster than the distal portion 808. As the proximal portion 806 of the post-biopsy cavity treatment implant 802 swells, it preferably swells from a shape in which it is easily implantable through the access path 127 to a shape and size wherein at least the proximal portion 806 thereof no longer fits through the access path 127. As this swelling occurs rapidly after the post-biopsy cavity treatment implant 802 comes into contact with the fluids present within the cavity 126, the surgeon may retract the introducer 804 from the cavity 126, close the initial incision and be confident that the post-biopsy cavity treatment implant 802 has remain in its intended position, squarely within the cavity chamber 128 of the cavity 126, and has not migrated back into the access path 127.

The post-biopsy cavity treatment implant 802 may alternatively be structured such that its distal 808 portion swells faster than its proximal portion 806 such as shown in FIG. 10B, such that both the proximal and distal portions 8f the post-biopsy cavity treatment implant swell relatively faster than the portion thereof between the proximal and distal portions or such that the proximal and distal portions 852, 856 of the implant 850 swell relatively slower than a middle portion 854, as shown in FIG. 10C. Alternatively still, the post-biopsy cavity treatment implant 802 may not have well defined proximal and distal portions and the post-biopsy cavity treatment implant 802 may be structured such that one portion thereof swells at a different rate than another portion thereof, for the purpose outlined above or for different purposes altogether—such as cavity shaping, for example. As suggested in FIGS. 9 and 10A, 10B, the post-biopsy cavity treatment implant 802 may be formed from a tightly rolled up sheet of swellable material. Alternatively, the post-biopsy cavity treatment implant 802 may be formed of stacked layers of swellable material as shown in FIG. 10C. Alternatively still, the post-biopsy cavity treatment implant 802 may be formed as a single unitary and homogeneous mass of swellable material and molded or cut (stamped) into the desired shape. Other embodiments include post-biopsy cavity treatment implants formed of or including fibers, fibrils and/or bundles of fibers and/or fibrils.

According to embodiments of the present invention, the present post-biopsy cavity treatment implant may include or be formed of biocompatible and water swellable material, such as collagen, for example. The collagen molecule is rod-shaped triple helix and consists of a three polypeptide chains coiled about each other. Besides the central triple helical region of the collagen molecule, there are terminal peptides regions known as telopeptides. These telopeptides are non-helical and are subdivided into two groups; namely, amino terminals and carboxyl terminals. Intermolecular crosslinking between triple helical molecules of collagen occurs in the telopeptides regions. Crosslinking may also occur within the central triple helical region of the collagen molecule, and is known as intramolecular crosslinking. It is the control of the formation and density of such crosslinks that is responsible for some of the mechanical, physicochemical and biological properties of the embodiments of the present post-biopsy cavity treatment implant disclosed herein.

The embodiments of the present post-biopsy cavity treatment implant may be selectively biodegradable and/or bioabsorbable such that it degrades and/or is absorbed after its predetermined useful lifetime is over. An effective way of controlling rate of biodegradation of embodiments of the present post-biopsy cavity treatment implant is to control and selectively vary the number and nature (e.g., intermolecular and/or intramolecular) of crosslinks in the implant material. Control of the number and nature of such collagen crosslinks may be achieved by chemical and/or physical means. Chemical means include the use of such bifunctional reagents such as aldehyde or cyanamide, for example. Physical means include the application of energy through dehydrothermal processing, exposure to UV light and/or limited radiation, for example. Also, a combination of both the chemical and the physical means of controlling and manipulating crosslinks may be carried out. Aldehydes such as glutaraldehydes, for example, are effective reagents of collagenous biomaterials. The control and manipulation of crosslinks within the collagenous matrix of the present post-surgery cavity treatment implant may also be achieved, for example, through a combination of dehydrothermal crosslinking and exposure to cyanamide. For example, the present post-surgery cavity treatment implant may, through proper control of the crosslinking density within the collagen matrix thereof, be designed and implemented to remain long term in situ at the implant site within the cavity 126. Crosslinking density may be indirectly measured, for example, via measurement of the swelling ratio where identical dry and wetted samples are weighted and weight is compared.

According to further embodiments of the present invention, the post-biopsy cavity treatment implant may be formed of or include other biomaterials such as, for example, bioresorbable poly(ester)s such as polylactide (PLA), polyglycolide (PGA), poly(lactide-co-glycolides) (PLGA), polyglyconate, polyanhydrides and their co-polymers, PEG, cellulose, gelatins, lipids, polysaccharides, starches and/or polyorthoesters and the like. According to an embodiment of the present invention, the present post-biopsy cavity treatment implant may be formed of or include collagen having a predetermined structure. Such predetermined structure refers not only to the overall shape of the implant, but also to the structure of its internal collagen matrix. Indeed, embodiments of the present invention include a macroporous cross-linked polymer matrix having a predetermined pore architecture. A "pore", as the term is used herein, includes a localized volume of the present post-biopsy cavity treatment implant that is free of the material from which the post-biopsy cavity treatment implant is formed. Pores may define a closed and bounded volume free of the material from which the post-biopsy cavity treatment implant is formed. Alternatively, pores may not be bounded and many pores may communicate with one another throughout the internal matrix of the present post-biopsy cavity treatment implant. The pore architecture, therefore, may include closed and bounded voids as well as unbounded and interconnecting pores and channels. The internal structure of the post-biopsy cavity treatment implant according to embodiment of the present invention defines pores whose dimensions, shape, orientation and density (and ranges and distributions thereof), among other possible characteristics are tailored so as to maximize the visibility of the resultant post-biopsy cavity treatment implant 802 under various modalities, notably ultrasound and X-ray, for example. Unlike polymeric matrices that contain bubbles of gas through a process in which gas is forced through a dispersion in a hydrated state, embodiments of the present post-biopsy cavity treatment implant have an internal structure that defines internal voids without requiring such gas to be forced therethrough. There are numerous methods and technologies available for the formation collagenous matrices of different pore architectures and porosities. By tailoring the dimensions, shape, orientation and density of the pores of the present implant, a recognizable pattern of post-biopsy cavity treatment implant material may be formed that may be readily visualized under, for example, ultrasound, X-ray, elastography or microwave radiation. This recognizable pattern may then influence the pattern of tissue ingrowth within the cavity 126, forming a porous scaffold on and within which tissue may infiltrate and grow. In turn, this pattern of tissue ingrowth may be readily recognizable under ultrasound and/or other imaging modalities discussed above long after the post-biopsy cavity treatment implant has been absorbed by the body or has degraded.

According to an embodiment of the present invention, the post-biopsy cavity treatment implant may be formed of or include a collagen matrix having a predetermined pore architecture. For example, the post-biopsy cavity treatment implant may include one or more sponges of lyophilized collagen having a predetermined pore architecture. Suitable collagen material for the post-biopsy cavity treatment implant may be available from, for example, DEVRO, Integra Life Sciences, Collagen Matrix and Kensey Nash, among others. The present post-biopsy cavity treatment implant, after implantation in the cavity 126, swells on contact with various body fluids therein and substantially fills a predetermined portion or the entire biopsied cavity, and does so in predictable manner.

Such a post-biopsy cavity treatment implant may be configured to have a hemostatic functionality to stop bleeding within the cavity 126 through a biochemical interaction with blood (such as coagulation) and/or other bodily fluids. The post-biopsy cavity treatment implant may, according to further embodiments, also be used to medically treat the patient. That is, the porous matrix of the present post-biopsy cavity treatment implant may be imbibed or loaded with a therapeutic agent to deliver the agent through elution at the cavity 126. Such a therapeutic agent may include, for example, an antibiotic agent, an analgesic agent, a chemotherapy agent, an anti-angiogenesis agent or a steroidal agent, to name but a few of the possibilities.

The post-biopsy cavity treatment implant 802 shown in FIGS. 9 and 10 may be formed of one or more thin sheets of collagen material having a predetermined (and controlled) pore architecture that has been rolled up into a cylinder shape. As the post-biopsy cavity treatment implant 802 swells with water from the cavity 126, it may unroll partially or entirely, and at least partially fill the cavity 126, including at least a portion of the cavity chamber 128. Some of the access path 127 may also be filled as the post-biopsy cavity treatment implant 802 swells. The post-biopsy cavity treatment implant 802, according to embodiments of the present invention, has a predetermined pore architecture or a combination of predetermined pore architectures, as will be described hereunder with reference to the drawings. The description of the figures below assumes that the post-biopsy cavity treatment implant is formed of or contains collagen, it being understood that the embodiments of the present invention disclosed herein are not limited to collagen and that aspects of the present inventions may readily be applied to such non-collagen containing post-biopsy cavity treatment implants.

FIG. 11 shows a post-biopsy cavity treatment implant 1100 having predetermined pore architectures, according to an embodiment of the present invention. As shown therein, the post-biopsy cavity treatment implant 1100 may include a first portion 1102 and a second portion 1 104. The collagen matrix of the first portion 1102 of the device 1100 defines a plurality of pores 1106 having a first predetermined pore architecture and the collagen matrix of the second portion 1104 of the device 1100 defines a plurality of pores 1108 having a second predetermined pore architecture. The dimensions of the layers or portions may be selected at will, preferably accounting for the dimensions of the cavity into which the device is to be inserted. As shown, the first pore architecture features pores 1106 that are relatively small, have a narrow pore size distribution and are substantially randomly oriented. In contrast, the second pore architecture features pores 1108 that have a relatively larger size, have a wider pore size distribution, are predominantly oriented along the axis indicated by double-headed arrow 1110 and are less densely distributed than the pores 1106 of the first portion 1102 of the post-biopsy cavity treatment implant 1100. Between the first and second portions 1102 and 1104 lies the interface 1103. As shown, the post-biopsy cavity treatment implant 1100 may be formed of a first collagen matrix having a first predetermined pore architecture and a second collagen matrix having a second pore architecture. The two collagen matrices may each be formed from separate collagen dispersions, each of which may be caused to form pores having predetermined characteristics and may each be at least partially lyophilized and formed (e.g., molded, cut or stamped) into the desired shape (in the illustrative case of FIG. 11, a substantially cylindrical shape). The two collagen plugs formed thereby may then be stacked one on the other, re-wetted and again lyophilized through a lyophilization process in a specifically shaped mold (for example) to form the stacked laminate structure shown in FIG. 11. Other methods of making the post-biopsy cavity treatment implant 1100 may occur to those of skill in this art. Not only may the predetermined pore architectures of the first portion 1102 and of the second portion 1104 cause these portions to be visible under, for example, ultrasound, but the interface 1103 therebetween may also be visualizable and recognizable under, for example, ultrasound as the boundary between two regions having a pronounced density differential. As can be seen, the post-biopsy cavity treatment implant 1100 is not formed of a rolled up sheet of material, as is the post-biopsy cavity treatment implant 802 in FIGS. 9 and 10. Instead, the post-biopsy cavity treatment implant 1100 is formed of solid matrices of collagenous material. It is to be understood that the pore architecture of the first and second portions 1102, 1104 may be varied at will by, for example, changing the porosity and/or crosslinking of the collagen chains, the pore density, the distribution of pore size, the orientation of the pores and the shape of the pores, to mention a few of the possible pore parameters. By judiciously choosing the pore architectures of the first and second portions 1102, 1104, one end of the post-biopsy cavity treatment implant 1100 may be caused to swell at a faster rate than the other end thereof. This is the case illustrated in FIG. 10.

Moreover, the cross-sectional characteristics of the post-biopsy cavity treatment implant 1100 may be changed. For example, the first portion 1102 may form a cylindrical inner core of collagenous material having a first predetermined pore architecture and the second portion 1104 may form a cylindrical outer shell around the inner core and may define a second pore architecture. In this manner, the outer surface of the post-biopsy cavity treatment implant 1100 may swell at a different rate (e.g., faster) than the rate at which the inner core swells. Moreover, the pore architectures may be chosen to maximize not only water absorption, but also to promote tissue ingrowth, to facilitate imaging and/or may be tailored to contain and release a pharmaceutical agent at a controllable rate and/or under predetermined conditions. Alternatively, the inner core may be formed of or include a non-collagenous material (such as a polylactic or polyglycolic material, for example) and the outer shell may include a collagenous material, for example. The outer shell may include a solid matrix of collagenous material having a predetermined pore architecture and/or may include wound fibers of collagenous material having a predetermined pore architecture, for example.

FIG. 12 shows a post-biopsy cavity treatment implant 1200 having predetermined pore architectures, according to another embodiment of the present invention. As shown, the post-biopsy cavity treatment implant 1200 includes a first portion 1202 and a second portion 1204, each of which has a predetermined pore architecture. It is to be noted that the present post-biopsy cavity treatment implants may have more than the two portions shown in both FIGS. 11 and 12 (or may define only a single portion). As shown, the post-biopsy cavity treatment implant 1200 is shaped as a substantially rectangular sponge. The first portion 1202 is stacked on the second portion 1204. As with the embodiment shown in FIG. 11, the first and second portions may have pore architectures that facilitates tissue ingrowth, wound healing and are readily visualizable and/or recognizable under one or more imaging modalities. The different pore architectures of post-biopsy cavity treatment implants according to embodiments of the present invention may also be chosen so as to maximize the visibility of the interface (such as reference numeral 1203 in FIG. 12) therebetween under the desired imaging modality such as, for example, ultrasound.

Post-biopsy cavity treatment implants according to embodiments of the present invention need not be formed as a solid mass of collagen (FIGS. 11, 12) or as a rolled up sheet of collagen (FIGS. 9, 10). FIGS. 13A, 13B and 13C show various other configurations for the present implant. As shown therein, embodiments of the present invention may include or be formed of a bundle of fibers or fibrils 1302 of (for example) collagenous material having one or more predetermined pore architectures. The pores defined within the collagen matrix of all or some of the fibers are not shown in FIGS. 13A-13C, but are nevertheless present. The bundle 1300 of fibers shown in FIG. 13A may be used to form post-biopsy cavity treatment implants by, for example, forming them into a rope-like structure as shown in FIG. 13B. In the cross-sectional representation of FIG. 13B, the longitudinal axis of the individual constituent fibers is perpendicular to the plane of the page on which they are printed. Post-biopsy cavity treatment implants may also be formed from the bundle 1300 of FIG. 13A by cutting (at 1304, for example) the bundle 1300 into a plurality of sections at an angle that is (for example) perpendicular to the longitudinal axis of the fibers 1302, so as to form a post-biopsy cavity treatment implant whose constituent fibers run from one end of the post-biopsy cavity treatment implant to the other end thereof, as shown in the detail representation of FIG. 13C. According to an embodiment of the present invention, a post-biopsy cavity treatment implant may be formed of a volume of collagenous material having a predetermined pore architecture or a combination of several bounded volumes of collagenous materials, each with a predetermined pore architecture. For example, several sponges having the structure shown in FIG. 13C may be stacked onto each other to define a laminate structure having a layered, composite pore architecture.

FIG. 13D shows another embodiment of the present post-biopsy cavity treatment implant. As shown, the implant 1306 includes a first portion 1308 and a second portion 1310. According to an embodiment of the present invention, the first portion 1308 may include a solid matrix of collagenous material 1312 having a first predetermined pore architecture. The second portion 1310 may include a plurality of fibers or fibrils 1314. The plurality of fibers may also be formed of or include collagenous material, and this collagenous material may have the same pore architecture as the first portion 1308 or a different pore architecture. The plurality of fibers may be formed or include non-collagenous material, such as polylactic or polyglycolic acid, for example. In the case wherein the plurality of fibers 1314 are formed of a collagenous material, after implantation in a biological fluid environment such as a cavity within a patient, the second portion 1310 may swell at a faster rate than the first portion 1310, as the constituent fibers 1314 thereof may be exposed to the biological fluid environment of the cavity over their entire surface. This swelling rate differential between the first and second portions 1308, 1310 may serve to further secure the implant 1306 within the cavity. In the case wherein the cavity is relatively dry, the physician may choose to introduce a volume of an aqueous solution, such as saline, into the cavity to speed the swelling of the implant 1306. The implant 1306 may be formed from a collagen dispersion in a mold configured to form the first portion 1308 and the second portion 1310 and lyophilized. Alternatively, the fibers 1314 may be formed after lyophilization by cutting the implant 1306 so as to form the plurality of fibers 1314. Alternatively still, the first and second portions 1308, 1310 may be formed by superimposition of the first and second portions 1310, 1310, as discussed above. Other means of forming the first and second portions 1310, 1312 may occur to those of skill in this art.

FIG. 13E shows another embodiment of the present post-biopsy cavity treatment implant. As shown therein, the implant 1316 is similar to the embodiment of FIG. 13D, but for the addition of a third portion 1318 on another surface of the first portion 1308. The third portion 1318 may be formed as detailed above relative to second portion 1310. The pore architecture of the third portion 1318 may be the same as that of the first portion 1308 and the second portion 1310, or may be different therefrom. It should be noted that various modifications to the embodiments of FIGS. 13D and 13E may be envisaged. For example, the embodiment of the implant 1316 of FIGS. 13E may be modified to include additional fibers or fibrils projecting from other surfaces of the first portion 1308. Other modifications may occur to those of skill in this art, and all such modifications are deemed to fall within the scope of the present invention.

FIG. 14A through 14E show other illustrative embodiments of the post-biopsy cavity treatment implants according to the present invention. As shown in FIG. 14A, two or more bundles of fibers of collagenous material (for example—the fibers may be made of or include other materials) may be used in the formation of post-biopsy cavity treatment implants according to embodiments of the present invention. As shown, the pores within the fibers of the first bundle 1402 may collectively define a first pore architecture, whereas the pores within the fibers of a second bundle 1404 may collectively define a second pore architecture that is different from the first pore architecture. The two bundles 1402, 1404 may then be joined together, for example, by re-wetting the bundles, stacking them and lyophilizing the composite structure. The length and diameter of the fibers may be selected and varied at will. The fibers or bundles thereof may even be woven together. From this composite structure, post-biopsy cavity treatment implants may be formed. As shown in FIG. 14B, the bundles of fibers may be arranged in a cylindrical shape, for example. Such a cylindrical shape may include an inner core 1406 of fibers having a first pore architecture and an outer shell 1408 surrounding the inner core 1406. The outer shell may include fibers having a second pore architecture that is different from the pore architecture of the inner core 1406. FIG. 14C shows a detail of a post-biopsy cavity treatment implant having a first portion 1402 of fibers having a first pore architecture and a second portion 1404 having a second pore architecture, formed, for example, by cutting the composite structure of FIG. 14A at 1410. Alternatively still, the fibers may be arranged such that the constituent fibers thereof closer to the center of the post-biopsy cavity treatment implant conform to a first pore architecture whereas the outside constituent fibers thereof conform to a second pore architecture that is different from the first pore architecture. As shown in the exploded views of FIGS. 14D and 14E, the post-biopsy cavity treatment implant may be have a layered laminate structure in which sheets formed of fibers (or woven fibers) having a first pore architecture are stacked onto sheets formed of fibers having a second pore architecture. As shown in FIG. 14E, many variations on this theme are possible. As shown therein, the orientation of the fibers (and thus of the pores defined by the collagenous matrix thereof) may be varied. For instance, whereas the fibers of the first (top or outer, for example) portion of the post-biopsy cavity treatment implant may be oriented in a first direction, whereas the fibers of the second (bottom or inner, for example) portion of the post-biopsy cavity treatment implant may be oriented along a direction that is different from the first direction (perpendicular thereto, for example). Imaging such post-biopsy cavity treatment implants within a cavity (such as shown at 126 in FIGS. 9 and 10, for example) using sonography may yield an image in which any fluids contained in the cavity 126 may appear substantially black, because the sound waves travel directly through such anechoic media, and a gradation of visible structures defined by comparatively hypoechoic layers or portions of the post-biopsy cavity treatment implant whose echogenicity is lower than the surrounding area and defined by hyperechoic layers or portions of the post-biopsy cavity treatment implant whose echogenicity is higher than the surrounding area.

FIGS. 14F and 14G illustrate the stacked structure of a post-biopsy cavity treatment implant, according to further embodiments of the present invention. The embodiments of FIGS. 14F and 14G are similar to the embodiments shown in FIGS. 14D and 14E, but for the structure of the stacked sheets of collagenous material. In FIGS. 14F and 14G, the stacked sheets of collagenous material are not formed of fibers or fibrils, but instead are each formed of a solid mass of collagenous material. The sheets may have the same or different pore architectures. Moreover, the sheets of collagenous material may define pore architectures in which the predominant orientation of the pores is varied. For example, some of the sheets may have a pore architecture in which the pores are predominantly oriented along the y-axis (FIG. 14F) or along the x-axis (FIG. 14G), for example. Alternatively, the constituent sheets of collagenous materials may define pore architectures in which other pore characteristics (size, shape, density, for example) are varied according to a predetermined pattern to influence tissue growth, visualization, etc. The resulting laminate structure may be formed (e.g., molded or cut) in the desired shape of the implant. For example, the resulting laminate structure may then be rolled into a cylindrical shape, as suggested in FIGS. 8 and 9, for example.

FIG. 15A shows a post-biopsy cavity treatment implant according to another embodiment of the present invention. As shown, the post-biopsy cavity treatment implant 1500 includes an inner portion 1502 and an outer portion 1504. The inner portion 1502 may be radiopaque. For example, the inner portion 1502 may be or include a metallic element. The metallic element may have a simple bar shape as shown, or may have a more complex shape such as, for example, a ring. The inner portion 1502 may have other structures to, for example, adhere or hook onto the walls of the cavity 126. Wound around the inner portion 1502 is one or more fibers 1504 of swellable (collagenous, for example) material having one or more predetermined pore architectures and/or one or more controlled crosslinking densities. The inner portion may be completely encased within the wound bundles of fibers or fibrils 1504 or may be only partially encased, as shown in FIG. 15A. The inner element 1502, rather than being radiopaque, may have a predetermined echogenicity so as to be immediately recognizable under ultrasound. The inner element 1502, moreover, may include an inner reservoir configured to contain a volume of therapeutic agent. For example, the inner element 1502 may be bioabsorbable and may be configured to release the contained pharmaceutical agent at a controlled rate. A plurality of fibers 1504 (having the same or different pore architectures) may be wound about the inner element 1502, the windings thereof being oriented at a given inclination or mutually different inclinations. Moreover, the embodiments of FIGS. 11 through 14E may advantageously be provided with an inner element as shown at 1502 and/or as described immediately above.

FIG. 15B and the cross-sectional representation of FIG. 15C show another embodiment of the present post-biopsy cavity treatment implant. As shown therein, the implant 1506 may include a first inner portion 1508 forming an inner core and a second outer portion 1510 forming an outer shell around the first inner portion 1508. Both the first and second portions may be formed of or include a collagenous material. The first portion 1508 may have a first predetermined pore architecture and the second portion 1510 may have a second predetermined pore architecture that is different from pore architecture of the first portion 1508. For example, the first portion 1508 may have a greater pore density (number of pores per unit volume) than the second portion 1510. In the exemplary implant 1506 shown in FIGS. 15B and 15C, the pore architecture of the first portion 1508 is such that the collagenous material thereof defines pores that are both smaller and more densely packed than those defined by the collagenous material of the second portion 1510. Although FIGS. 15B and 15C show the implant 1506 as shaped as a right cylinder, the implant 1506 may be molded into most any shape, to accommodate most any cavity shape. In this manner, the implant may be configured such that its ultimate size and shape after implantation and swelling, substantially matches the size and shape of the cavity in which it is implanted. As shown in the cross-sectional representation of FIG. 15C, the first portion 1508 of the implant 1506 may define an inner reservoir 1512 (created as a void within the first portion 1508 or as a discrete biocompatible reservoir or pouch having a predetermined biodegradability rate). The inner reservoir 1512 may be pre-loaded with a dye/pigment and/or a pharmaceutical agent, as indicated at 1514 in FIG. 15C. The pharmaceutical agent may be configured to slowly release into the cavity 126 as soon as the implant is inserted therein and/or may be configured to require a physician or a RN to pinch or squeeze (or otherwise breach) the implant 1506 to rupture the reservoir 1512 to release the dye/pigment and/or pharmaceutical agent 1514 contained therein.

FIG. 15D shows another embodiment of the implant according to the present invention. The implant 1516 includes a first portion 1508 defining a first pore architecture, such as described above relative to FIGS. 15B and 15C. The implant 1516 may include a reservoir 1512, and the reservoir 1512 may contain a volume of dye/pigment and/or one or more therapeutic agents. Wound around the first portion 1508 is one or more fibers or fibrils of collagenous material defining a second pore architecture that may be different from the first pore architecture. The fibers or fibrils 1520 may completely encase the first portion 1508 or may do so only partially, as shown in FIG. 15D. FIGS. 15E and 15F show another embodiment of the present invention. In this embodiment, the implant 1518 also includes a first portion 1508 defining a first pore architecture, as described relative to FIGS. 15B-15D above. At least partially surrounding the first portion 1508 are a plurality of fibers or fibrils 1508 that define a second pore architecture that may be different from the first pore architecture. Several layers of such fibers or fibrils 1508 may be disposed around the first portion 1508, as suggested by the cross-sectional view of FIG. 15F.

Most any of the portions or layers of the embodiments disclosed herein may be configured to contain one or more dyes/pigments and/or pharmaceutical agents. The post-biopsy cavity treatment implants discussed herein may be rendered selectively radiopaque by the selective mechanical, chemical or physical incorporation of a radiopaque articles or particles into the collagenous matrix of embodiments of the present post-biopsy cavity treatment implant. For example, the post-biopsy cavity treatment implant may define pores having a predetermined and recognizable architecture and may incorporate some radiopaque compound or particles such as, for example barium sulfate or other commonly used radiopaque or radioactive materials.

Embodiments of the present invention may also include recognizable articles or substances within the collagenous matrix such as, for example, dyes and/or pigments (i.e., including both synthetic dyes and natural pigments). The dyes/pigments may be incorporated within the collagenous dispersion that forms the constituent layers or portions of the embodiments of the post-biopsy cavity treatment implants disclosed herein. Such dyes/pigments may form mapping compounds that may be gradually released into the body upon implantation of the present post-surgery cavity treatment implant and may form the basis of lymphatic mapping in the future. In this manner, lymphatic mapping may be carried out immediately after a biopsy procedure via elution of the mapping compound (e.g., dyes/pigments and/or radioactive agent) deposited into the collagenous matrix of the implant. In the case wherein a cancer is detected or suspected in the tissue specimen retrieved by the biopsy procedure, this elution of mapping compound from the post-biopsy cavity treatment implant may enable the physician to skip the conventional step of injecting dyes/pigments into the patient, which dye/pigment injection step is conventionally carried out prior to a (sentinel) lymph node status evaluation procedure. Embodiments of the post-biopsy cavity treatment implant according to present invention may include metal-less dyes/pigments as well radiopaque, radioactive or paramagnetic metal-containing dyes/pigments such as, for example, porphyrins and/or porphyrin derivatives (such as chlorophyll and/or chlorophyll derivatives, for example) that are bound to the collagenous matrix. The porphyrins and/or porphyrin derivatives may be tailored, for example, to enhance crosslinking and enhance wound healing and/or to control biodegradation, among other reasons. A metal with paramagnetic properties (such as Mn, for example) may be placed within the porphyrins or porphyrin derivatives so that another mode of recognition may be achieved. Impregnation of the present post-biopsy cavity treatment implant with porphyrins or porphyrin derivatives (for example, copper chlorophyllin) gives the post-biopsy cavity treatment implant a lymphatic mapping functionality due to the elution of the porphyrins or porphyrin derivatives into the surrounding tissue lymphatic drainage system.

According to other embodiments of the present invention, the present post-biopsy cavity treatment implants may define or include an internal reservoir configured to contain a volume of a mapping compound and/or a beneficial therapeutic agent. Following the biopsy procedure and the subsequent implantation of the present post-biopsy cavity treatment implant having a predetermined pore architecture into the biopsy cavity and following a histopathology report on the excised biopsy specimen, the physician or RN may pinch or squeeze the post-biopsy cavity treatment implant to express the mapping compound(s) and/or agent(s) into the surrounding tissue via lymphatic system to the sentinel node and other lymphatics. In the absence of such squeezing or pinching, the mapping compound and/or therapeutic agent may much more gradually find its way into the surrounding tissue through elution following a gradual biodegradation of the reservoir.

FIGS. 16-20 are photomicrographs of collagenous matrices having various pore architectures. As shown, the porosity of the collagenous material is not formed by bubbles forced through the collagen dispersion prior to lyophilization thereof. Indeed, it is the structure of the collagen material itself that creates and defines the voids or pores (anechoic regions that appear black in the photomicrographs) within the material. FIGS. 17 and 19 show relatively round pores having a wide size distribution, whereas FIGS. 16 and 18 show a relatively denser collagen matrix having a smaller pore size distribution. FIG. 20 shows an example of a collagenous matrix that is relatively less dense than, for example, the matrix shown in FIG. 18.

FIGS. 21-23 are combinations of photomicrographs to illustrate further embodiments of the post-biopsy cavity treatment implants according to the present invention. FIGS. 21 shows a post-biopsy cavity treatment implant 2100 that includes a first portion 2102 having a first pore architecture and, stacked thereon, a second portion 2104 having a second pore architecture. As shown, the pore architecture of the first portion 2102 may be characterized as being relatively denser than the pore architecture of the second portion 2104. Alternatively, the post-biopsy cavity treatment implant 2100 may be structured such that the first portion has a higher porosity (is less dense) than that of the second portion 2104. The thicknesses of the first and second portions 2102, 2104 may be varied at will. More than two layers of collagenous material may be provided.

FIG. 22 shows a post-biopsy cavity treatment implant 2200 having a graduated porosity profile. Such a post-biopsy cavity treatment implant 2200 may be formed by lining up a plurality of collagen matrices having of progressively lower densities. That is, matrix 2002 has the highest density (amount of collagen per unit volume), matrix 2204 has the next highest density, matrix 2206 has the next to lowest porosity and matrix 2208 has the lowest porosity of the entire post-biopsy cavity treatment implant 2200. Alternatively, the degree to which each matrix is crosslinked may be varied and controlled. For example, each matrix may be crosslinked to a different degree through the use of, for example, gluteraldehyde. For example, matrix 2202 may be configured to have about 0.0085% gluteraldehyde, matrix 2204 may be configured with about 0.0075% gluteraldehyde, matrix 2206 may be configured with about 0.0065% gluteraldehyde and matrix 2208 may be configured with about 0.0055% gluteraldehyde, for example. Other concentrations are possible, as are different reagents. After superimposing all four such matrices 2202, 2204, 2206 and 2208, a (in this case, piece-wise linear) cross-linking and/or porosity gradient may be achieved across the embodiment of the present post-biopsy cavity treatment implant shown at 2200.

FIG. 23 shows a composite post-biopsy cavity treatment implant 2300 having a more complex structure, according to another embodiment of the present invention. The post-biopsy cavity treatment implant 2300 includes three distinct collagen matrices, as shown at 2302, 2306 and 2308. As shown, each of the matrices 2302, 2306 and 2308 has a unique pore architecture. Indeed, the portion of the post-biopsy cavity treatment implant referenced at numeral 2302 has a dense appearance, in which the pores have a high aspect ration and are aligned substantially parallel to the length of the device 2300. The post-biopsy cavity treatment implant 2300 also includes a second portion 2304 that includes two unique collagenous matrices referenced at 2306 and 2308, each having different pore architectures. Whereas matrix 2306 features a wide distribution of pore shapes and sizes, matrix 2308 features comparatively larger, generally rounder pores than those of matrix 2306. Each of these matrices 2302, 2306 and 2308 may have a unique ultrasonic or X-ray signature and/or contain dyes/pigments or radiopaque materials or compounds. Moreover, not only may the various matrices be visible under selected modalities, the interfaces therebetween may also provide the physician with position and orientation information of the post-biopsy cavity treatment implant within the cavity. Indeed, there are distinct interfaces between dissimilar materials between matrices 2302 and 2306, between matrices 2302 and 2308 as well as a distinct interface between adjoining matrices 2306 and 2308, each of which may be readily visible under, for example, ultrasound. It is to be noted that the interfaces between the external surfaces of all three matrices 2302, 2306 and 2308 with the surrounding tissue may also provide the physician with additional visual clues are to the position and orientation of the post-biopsy cavity treatment implant 2300 within the cavity in which it is implanted. The interfaces described herein, as well as the different rates of swelling may be achieved through control of the porosity and/or as through the control of crosslinking. A single post-biopsy cavity treatment implant may include constituent portions controlled to have a predetermined pore architecture and/or predetermined portions having controlled crosslinking. Although the irregular closed features within the drawings are intended to suggest pores of various configurations and densities, they are alternatively intended to indicate crosslinking. Therefore, illustrated differences in these irregular closed features between adjacent portions of an implant may also be interpreted as being differences in crosslinking densities between adjacent portions in the implant.

Use of the post-biopsy cavity treatment implants disclosed herein is not limited to filling post biopsy cavities. Indeed, the present post-biopsy cavity treatment implants also find utility in the correction of defects caused by poorly healed cavities, whatever their origin or cause. The present post-biopsy cavity treatment implants may be placed in cavities in which it is desired that the collagen matrices be replaced, over time, with (human or animal) autogenous tissue. Hence, the embodiments of the present invention may be used for the repair of tissue that has been damaged due to tissue removal, thereby providing a favorable tissue scaffold in which autogenous tissue may infiltrate and grow. In addition, embodiments of the post-biopsy cavity treatment implants according to the present invention may serve to absorb exudates within the cavity, thereby further facilitating the healing process.

FIG. 24 shows a post-biopsy cavity treatment implant 2400, according to another embodiment of the present invention. The post-biopsy (or, more generally, post-excisional) implant 2400 includes a radiopaque element 2402. The radiopaque element may be formed as a clip, a staple, or may have other shapes, as discussed herein below with reference to FIGS. 34, 36 and 38-40. The radiopaque element 2402 may also exhibit other characteristics, besides its visibility under X-Ray. For example, the element 2402 may have paramagnetic characteristics, to enable the implant 2400 to be visible under electron paramagnetic resonance-spectroscopy.

Coupled to the radiopaque element 2402 is a core portion 2404. The core portion 2404 may include a first porous matrix that defines a controlled pore architecture. The pore architecture of the core portion 2404 may be controlled in a manner similar to that described above. According to an embodiment of the present invention, the core portion 2404 may include or be formed of, for example, a polylactide (PLA), a polyglycolide (PGA), a poly(lactide-co-glycolide) (PLGA), a polyglyconate, a polyanhydride, PEG, cellulose, a gelatin, a lipid, a polysaccharide, a starch and/or a polyorthoester.

Coupled to the core portion 2404 is a shell portion 2406 that includes a second porous matrix defining a second controlled pore architecture that is different from the pore architecture of the core portion 2404. According to an embodiment of the present invention, the shell portion 2406 includes collagen. Such a collagenous shell portion 2406 may be selectively configured to have a predetermined pore density, pore shapes, pore sizes and pore orientation, for example. Such controlled pore architecture may influence the degree and the manner in which the collagenous shell portion 2406 swells when the implant 2400 is placed, immersed or implanted in a biological fluid environment, such as a cavity within a patient's body. Such controlled pore architecture also influences tissue ingrowth, by providing a scaffolding support structure on and within which new tissue may develop. The rate at which the shell portion 2406 degrades within the body may also be influenced by controlling the crosslinking of the collagenous matrix of the shell portion 2406. By controlling the formation and the density of crosslinks, it is possible to control and/or influence some of the mechanical, physicochemical and biological properties of the collagenous shell portion 2406.

Visualization of the post-biopsy cavity treatment implant 2400 is facilitated not only by the presence of the radiopaque element 2402 within the core portion 2404, but also by means of the echogenic nature of the core portion 2404 and of the shell portion 2406. Such dissimilar pore architectures in the core portion 2404 and shell portion 2406 may also influence the relative elasticity of the two portions 2404 and 2406 further enabling the implant to be visible under elastography.

More than one radiopaque element 2402 may be present in the core portion 2404. Moreover, another element exhibiting radiopacity, having paramagnetic characteristics and/or visible under other modalities (such as ultrasound, for example), may be present in the core portion 2404 and/or the shell portion 2406. At least the shell portion 2406 may include a dye, a pigment, a contrast medium and/or a beneficial therapeutic agent (for example) disposed therein. Such dye, a pigment, a contrast medium and/or a beneficial therapeutic agent may be held sponge-like within the porous matrix of the shell portion 2406 and delivered through elution over time, but may also be contained within an internal reservoir (a voided space) defined within the core portion 2404 and/or the shell portion 2406. For example, the internal reservoir may be configured to deliver the dye, pigment, contrast medium and/ or therapeutic agent at a first rate when the reservoir is breached and at a second rate that is lower than the first rate when the reservoir is not breached.

FIG. 25 shows the post-biopsy cavity treatment implant 2400 of FIG. 24 loaded into an exemplary introducer 804, according to an embodiment of the present invention. The post-biopsy cavity treatment implant 2400, in a pre-implanted state, may be loaded into the introducer 804, which may then be inserted into the tissue 110 through the access path 127 and at least partially into the cavity chamber 128 of the cavity 126, in the manner illustrated in FIG. 8. The post-biopsy cavity treatment implant 2400 may then be delivered to the cavity 126 and thereafter be left in place and the introducer 804 withdrawn. The pre-implanted state of the post-biopsy cavity treatment implant 2400 is preferably in a state in which it occupies its minimum volume. According to an embodiment of the present invention, the pre-implanted state of the post-biopsy cavity treatment implant 2400 is a lyophilized (e.g., dehydrated) state and the post-biopsy cavity treatment implant may be configured to swell when placed within a biological fluid environment such as the cavity 126.

FIG. 26 shows a post-biopsy cavity treatment implant 2600 according to a still further embodiment of the present invention, in various stages of manufacture. Embodiments of the present post-biopsy cavity treatment device may assume most any shape that is suited to the shape and size of the cavity into which it is designed to be placed. One such shape is the generally right cylindrical shape (e.g., a disc) shown in FIG. 26. The implant 2600, at the top left hand of FIG. 26 is shown in an intermediate manufacturing shape; i.e., prior to assuming its final pre-implantation shape. The implant 2600 includes a radiopaque element 2602 that may be coupled with a core portion 2604. The core portion 2404, in FIG. 24, is shaped as a cylinder. However, the shape of the core portion may be freely selected. In FIGS. 26-27, the core portion 2604 has a generally rectangular cross-section. To couple the core portion 2604 with the shell portion 2606, the core portion 2604 may be placed on a pedestal within a mold. In the case wherein the shell portion 2606 includes collagen, a collagenous slurry may be poured into the mold and thereafter lyophilized. Other means and methods for manufacturing the implant 2600 may occur to those of skill in this art.

The implant 2600, according to one embodiment of the present invention, may be folded along a diameter thereof, in such a manner as to form the implant 2600 shown in the plan view shown in the lower left hand side of FIG. 26. Thereafter, the implant 2600 may again be folded along fold line 2611, in the manner suggested by arrow 2610 to create the implant 2600 shown in the lower right hand side of FIG. 26. Additional folding may then be carried out along fold lines 2612, 2614 and 2616 to create an implant 2600 having several layers and a generally wedge shape. The core portion 2604, depending upon how the folding has been carried out, may be sandwiched within several layers of the folded shell portion 2606. In this state, the implant 2600 may be further compressed and disposed in an introducer, an example of which is shown in FIG. 27 at 804 for eventual implantation within a post-biopsy cavity. It should be noted that the folding need not take place as illustrated in FIG. 26, but may be carried out in a different manner, to achieve a different ultimate shape for the implant 2600. In addition or in place of folding, the implant may also be rolled or crumpled (for example) into its intended pre-implantation shape.

FIG. 28 shows the post-biopsy cavity treatment implant 2600 of FIGS. 26 and 27 during implantation, according to an embodiment of the present invention. FIG. 29 shows the post-biopsy cavity treatment implant 2600 of FIG. 28 after implantation, illustrating the manner in which the implant 2600 may expand and/or unfold within the cavity 126 after implantation, according to an embodiment of the present invention. As shown, the introducer 804 may be inserted into the tissue through the access path 127 and at least partially into the cavity chamber 128 of the cavity 126. The post-biopsy cavity treatment implant 2600 may then be delivered to the cavity 126 and thereafter be left in place and the introducer 804 withdrawn. The pre-implanted state of the post-biopsy cavity treatment implant 2600 is preferably in a state in which the post-biopsy cavity treatment implant 2600 occupies its minimum volume. According to an embodiment of the present invention, the pre-implanted state of the post-biopsy cavity treatment implant 2600 is a lyophilized (e.g., dehydrated) state and the post-biopsy cavity treatment implant 2600 may be configured to swell when placed within a biological fluid environment such as the cavity 126. Whereas FIG. 28 shows the present post-biopsy cavity treatment implant 2600 immediately after implantation in tissue (i.e., still in a state in which it occupies its minimum volume), FIG. 29 shows the state of the present post-biopsy cavity treatment implant 2600 a period of time after implantation. As shown, the post-biopsy cavity treatment implant 2600 is no longer in its pre-implanted state. Indeed, the post-biopsy cavity treatment implant 2600 having been placed in a biological fluid environment (such as the patient's tissue), begins to swell. To accelerate the swelling, the surgeon may inject fluids after placing the device with the intent to "wet" the present post-cavity treatment implant 2600. Substances such as saline, fibrin solution or other catalyst or activator may be used for that purpose. For example, as part of the insertion device (such as, for example, the introducer 804), an integral vial may be crushed by the surgeon to release the activating fluid (for example, an aqueous solution, dye/pigment) within the cavity 126, thus causing rapid swelling of the implant 2600. Alternately, and as shown in FIG. 9, the introducer 804 may define an internal lumen 811 over its length and may include a fluid injection port 812 at the proximal end of the device. Fluids such as the aforementioned saline or fibrin may then be introduced into the cavity 126 through the fluid injection port 812 and the internal lumen 811 to cause the rapid swelling of the implant 2600 or for any other reason. Delivering such fluids can be especially useful if the field within the cavity 126 is relatively dry as can occur in the ideal case.

As the post-biopsy cavity treatment implant 2600 swells, it preferably swells from a shape in which it is easily implantable through the access path 127 to a shape and size wherein it no longer fits through the access path 127. As this swelling occurs rapidly after the post-biopsy cavity treatment implant 2600 comes into contact with the fluids present within the cavity 126, the surgeon may retract the introducer 804 from the cavity 126, close the initial incision and be confident that the post-biopsy cavity treatment implant 2600 has remain in its intended position, squarely within the cavity chamber 128 of the cavity 126, and has not migrated back into the access path 127.

As shown in FIG. 29, the release of the implant 2600 from compression at it is ejected from the introducer 804, combined with the hydration and subsequent swelling of the post-biopsy cavity treatment implant 2600 within the cavity 126 causes the implant 2600 to at least partially unfold (and/or unroll), thereby causing the volume that it occupies to increase. This unfolding and swelling may enable the implant 2600 to occupy a significant portion of the internal volume of the cavity 126. This, in turn, aids in promoting tissue ingrowth by providing scaffolding upon and within which new tissue may develop. Moreover, the now at least partially filled cavity 126 is readily visible under a variety of imaging modalities. As the ranges at which the core and shell portions may biodegrade may be controlled as detailed above, it is possible to manufacture the implant 2600 to have a predictable rate of biodegradation. After the core and shell portions of the implant have substantially degraded within the cavity, the radiopaque element will remain in the newly formed tissue within the cavity, providing a ready positional reference of the cavity 126, should that be subsequently necessary. More that one such implant 2600 may be placed within the cavity 126.

FIG. 30 shows a post-biopsy cavity treatment implant 3000 according to another embodiment of the present invention, in various stages of manufacture. The implant 3000 is similar to that shown in FIGS. 26-29, but for the presence of two core portions 3004, 3008 within the shell portion 3010. Each of the core portions 3004, 3008 surrounds a radiopaque element 3002, 3306, respectively. To form the implant 3000 in its ultimate pre-implantation shape (i.e., its shape prior to being placed in a biological fluid environment), the implant 3000 may first be folded along a diameter thereof, to achieve the shape thereof shown in the plan view in the lower left hand of FIG. 30. Thereafter, the implant 3000 may be sequentially folded along the direction indicated by arrows 3010 along the fold lines 3014, 3016, 3018 and 3020 to achieve a generally wedge shape.

It is to be noted that embodiments of the present post-biopsy cavity treatment devices are not limited to the shapes described and illustrated herein. Moreover, the present implants may be folded differently than shown, as they may be irregularly folded, rolled or otherwise caused to assume as small a volume as practicable. A greater number of core portions may be accommodated within the shell portion 3010. Other variations may occur to those of skill in this area, and all such variations are believed to fall within the scope of the present invention. FIG. 31 shows the post-biopsy cavity treatment implant 3000 of FIG. 30 loaded into an exemplary introducer 3022, according to another embodiment of the present invention.

FIG. 32 shows a post-biopsy cavity treatment implant 3000 according to yet another embodiment of the present invention, in a configuration prior to folding and/or compression. As shown, the post-biopsy cavity treatment implant 3000 may be shaped, for example, such that the shell portion 3010 is shaped as a rectangular sheet. The embodiment shown in FIG. 32 includes two radiopaque elements 3002 and 3006, although a lesser or greater number of such radiopaque elements may be present. Coupled to the radiopaque element 3002 is a core portion 3004 and coupled to the radiopaque element 3006 is another core portion 3008. In the illustrated embodiment, the core portion 3004 surrounds the radiopaque element 3002, the core portion 3008 surrounds the radiopaque element 3006 and the shell portion 3010 surrounds both core portions 3004 and 3008. Other arrangements of the constituent elements of the post-biopsy cavity treatment implant 3000 are possible.

According to one embodiment, the post-biopsy cavity treatment implant 3000 of FIG. 32 may be folded and/or rolled or otherwise arranged into any desired shape. FIG. 33 shows the post-biopsy cavity treatment implant 3200 of FIG. 32 in one such many possible folded configurations, according to still another embodiment of the present invention. After lyophilization, the implant 3200 may be folded two or more times (for example) and compressed into an introducer, such as shown in FIGS. 27 or 31. Any folding pattern may be used. Some of the goals of such folding, rolling and/or compression include reducing the dimensions of the implant 3200, fitting the shape of the implant 3200 to the shape and dimensions of the cavity into which the implant is to be placed, and to influence the manner in which the implant unfolds and/or unrolls within the cavity, upon being released from the introducer, decompressing and swelling with biological fluids within the environment of use within the patient. FIG. 33 is to be considered only as illustrative of one of many possible configurations for the implant 3200.

FIG. 34 shows a core portion 3400 suitable for use in conjunction with the present post-biopsy cavity treatment implant, according to another embodiment of the present invention. As shown, the core portion of the present post-biopsy cavity treatment implant need not be rectangular or cylindrical. In the embodiment of FIG. 34, although the core portion 3404 has a uniform cylindrical cross-section, it may exhibit a more complex geometry. For example, the center portion of the core portion 3403 may be locally thinner than the ends thereof This locally thinner portion facilitates any folding or rolling that may be carried out to bring the implant into its final (pre-implantation) shape and configuration. The core portion 3404 may be coupled to (or surround, as shown in FIG. 34) one or more radiopaque elements 3402. FIG. 35 shows a post-biopsy cavity treatment implant 3500 incorporating the core portion 3404 of FIG. 34, according to yet another embodiment of the present invention, in a configuration prior to folding and/or compression. The shell portion 3406 is coupled to the core portion 3403. As shown in FIG. 35, the shell portion 3406 may surround the core portion 3404. The implant 3500 may then be folded, rolled and/or compressed, as described above.

FIG. 36 shows further core portions 3604, 3608 suitable for use in conjunction with the present post-biopsy cavity treatment implant, according to another embodiment of the present invention. FIG. 37 shows a post-biopsy cavity treatment implant 3700 incorporating the core portions 3604, 3608 of FIG. 36, according to a further embodiment of the present invention, in a configuration prior to folding and/or compression. As shown in FIGS. 36 and 37, more than one core portion may be coupled to the shell portion 3406 and each (or only one) of such core portions 3604, 3608 may be coupled to (or surround) a radiopaque element, as shown at reference numerals 3602 and 3606. The core portion or portions of a post-biopsy cavity treatment implant according to an embodiment of the present invention may be fabricated in most any shape that is consistent with the cavity treatment goals. FIG. 38 shows a core portion 3804 having yet another possible shape. As with the core portions discussed herein, the core portion 3804 is coupled to or surrounds a radiopaque element 3802. The core portions shown in FIGS. 34-38 may be stamped from a sheet of core material. The core material, according to an embodiment of the present invention, may be formed of or include one or more of the following materials: a polylactide (PLA), a polyglycolide (PGA), a poly(lactide-co-glycolide) (PLGA), a polyglyconate, a polyanhydride, PEG, cellulose, a gelatin, a lipid, a polysaccharide, a starch and a polyorthoesters, for example.

FIGS. 39 and 40 shows exemplary radiopaque elements 3900 and 4000 suitable for use in conjunction with the present post-biopsy cavity treatment implant, according to still further embodiments of the present invention. The radiopaque element may be shaped as a staple or the letter "C" as shown in FIG. 38 or in another shape, such as shown in FIG. 39, in which the radiopaque element 400 has the general shape of the letter "R". Other shapes and configurations are possible.

FIG. 41 shows a post-biopsy cavity treatment implant 4100, according to a further embodiment of the present invention, in a configuration prior to folding and/or compression. A radiopaque element 4102 is coupled to (or surrounded by) a core portion 4104. In turn, the core portion 4104 is coupled to (or surrounded by) a shell portion 4106. This embodiment is similar to that shown in FIG. 26, but for the radial cuts 4108 in the shell portion 4106. The radial cuts 4108 may enable the implant 4100 to better accommodate and fill irregularly shaped cavities when the implant is placed in a biological fluid environment and the implant 4100 decompresses, unfolds or unrolls and swells. Such radial cuts define a plurality of independently movable free ends 4110 in the peripheral portion of the implant 4100.

FIG. 42 shows a post-biopsy cavity treatment implant 4200, according to another embodiment of the present invention, in a configuration prior to folding and/or compression. A radiopaque element 4202 is coupled to (or surrounded by) a core portion 4204, as shown in the cutout (the purpose of the cutout is only to show the internal structure of the implant 4200 and is not present in the actual implant). In turn, the core portion 4204 is coupled to (or surrounded by) a shell portion 4206. This embodiment is similar to that shown in FIG. 13E. The implant 4200 includes a radiopaque element 4202 coupled to or surrounded by a core portion 4204 that is, in turn, coupled to or surrounded by a shell portion 4206. The core portion 4204 and the radiopaque element may be configured and/or have any of the characteristics discussed above and shown in the corresponding figures. The shell portion 4206, as shown, defines a center portion 4208 and a peripheral portion and wherein the peripheral portion defines a plurality of independently movable free ends 4210.

For example, the post-biopsy cavity treatment implants disclosed herein may be configured to have a unique "signaturing" capability, in which a specific code appears under a given imaging modality. The specific code may be formed within or molded into the structure of the collagen matrix or matrices. For example, a combination of the elements with different crosslinking patterns (e.g., bundles of cylindrical fibers or layers of collagen sponges) may be used for both pattern recognition and predictable filling of the post biopsy procedure cavity. Alternatively, the code may be embodied as a discrete echogenic or radiopaque constituent element of the implant. The codes may confer information to the radiologist or treating physician when viewed under X-ray or ultrasound. Alternatively still, the post-biopsy cavity treatment implants having predetermined pore architectures and/or controlled crosslinking densities according to the disclosed embodiments may include a biocompatibly-sealed integrated circuit (such as a biocompatibly-sealed RFID chip or a biocompatibly-sealed Memory Spot from Hewlett-Packard, for example) that may be interrogated electronically while remaining in situ to convey information to the physician.

FIG. 43 shows a soft tissue marker, according to an embodiment of the present invention. As shown in FIG. 43, a soft tissue marker, according to an embodiment of the present invention, may include one or more first markers 4302 and one or more second markers 4304. The first marker may advantageously be configured to be visualized under ultrasound (i.e., be echogenic) and the second marker may advantageously be configured to be radiopaque. The first and second markers 4302, 4304 may uncoupled from one another, which makes them free to move relative to one another when delivered into a cavity in a breast or other structure (see FIG. 44). The second, radiopaque marker 4304 may be a discrete element, separate from the first marker 4302. That is, the second marker 4304 may be external to and separate from the first marker 4302. As shown in FIG. 43, the soft tissue marker may include a plurality of discrete elements (or markers) 4302, and one or more radiopaque elements 3404. In the embodiment shown in FIG. 43, the soft tissue marker includes six discrete elements 4302 and a single radiopaque element 4304, although other implementations are possible, as those of skill in this art will readily recognize. The discrete elements may, for example, be about 0.5 to 10 mm in length. According to embodiments of the present invention, the discrete elements may, for example, range from about 3 to 8 mm in length. For example, the discrete elements may measure about 5 mm or about 6.5 mm in length. Although the radiopaque element 4304 is shown in the middle of the discrete elements or markers 4302, that need not be the case, as the radiopaque element may be disposed, prior to the placement of the soft tissue marker in the patient, anywhere relative to the discrete echogenic elements 4302. In any event, the (one or more) discrete element 4302 and the (one or more) radiopaque element 4304 may be arranged, prior to placement thereof into the patient, as a train of markers 4302, 4304, one behind the other. Other configurations are possible, although placing the markers 4302, 4304 in a single file facilitates the emplacement thereof within the patient using a small diameter introducer.

The discrete elements (markers) 4302, according to embodiments of the present invention, may be substantially non-swellable when placed in an aqueous environment such as a cavity within a patient. The discrete and substantially non-swellable elements 4302, moreover, may be formed of or include a porous material and/or a non-porous material. That is, one or more of the discrete and substantially non-swellable elements 4302 may be formed of or include a porous material, while another or others of the discrete and substantially non-swellable elements 4302 may be formed of or include a substantially non-porous material. The porous material, as suggested by the magnifying glass 4306 in FIG. 43, may include internal surfaces that collectively define interconnected internal voids. For example, most of the internal surfaces of the elements 4302 may be common to more than one of the internal voids. That is to say, the porous material(s) of the elements 4302, rather than including internal surfaces that define discrete bubbles entrapped in the material, include surfaces that define interconnected voids that are not separated from one another by solid material, as is the case with materials that include entrapped discrete bubbles.

The pores of the porous material of one or more of the substantially non-swellable elements 4302 may, as noted above, have controlled characteristics. For example, the pore architecture of the porous material may be controlled as to, for example, pore density (e.g., the average number of pores within a given volume), pore orientation (e.g., the prevailing direction of the largest dimension of the pores) and/or pore dimension (e.g., the average magnitude of the largest dimension of the pores), as shown and discussed relative to FIGS. 11-42 herein. In addition, the pore architecture of one of the elements 4302 may be different from the pore architecture of another one or ones of the elements 4302. The pores of the material of the substantially non-swellable elements 4302 may be advantageously engineered to promote echogenicity—that is, to render the element(s) 4302 readily visible under ultrasound.

The material(s) included in the substantially non-swellable elements 4302 may be chosen for their controlled biodegradability. In contrast, the material(s) of or included in the radiopaque marker 4304 may be non-biodegradable. For example, the element(s) 4302 may be formed of or include a polymer having a porous structure which enhances visibility of the element 4302 under ultrasound and the radiopaque marker(s) 4304 may include or be formed of a metallic structure or material that enhances visibility of the second marker under X-ray. For example, the radiopaque marker 4304 may be formed of or include stainless steel or a Nickel-Titanium (NiTi) alloy (such as shown at http://www.nitinol.com/, for example) and/or other biocompatible radiopaque material. The element or elements 4302 may be formed of or include, for example, a polylactide (PLA), a polyglycolide (PGA), a poly(lactide-co-glycolide) (PLA-PGA), a polyglyconate, a polyanhydride, a lipid, a polysaccharide, and/or a polyorthoester, for example. Different ones of the elements 4302 may be formed of or include different materials. Moreover, the porosity characteristics of the substantially non-swellable elements

4302 may vary between different ones of the substantially non-swellable elements 4302 or even within a single one of the elements 4302.

FIG. 44 shows a device to deliver a soft tissue marker, according to an embodiment of the present invention. As shown, the soft tissue marker of FIG. 43 may be loaded into an introducer 4402. That is, a train of substantially non-swellable elements 4302 and one or more radiopaque elements 4304 may be loaded, single file, into an internal lumen 4404 of the introducer 4402. As shown, the introducer 4402 may include a delivery opening 4406 and the train of substantially non-swellable elements 4302 may be movable through the delivery opening 4406. As may be seen in FIGS. 43 and 44, the substantially non-swellable elements 4302 and the radiopaque element 4304, in this embodiment, are not attached or otherwise tethered or coupled to one another or to any other structure. The introducer 4402 may also include a piston 4408 or other structure which may be depressed by the surgeon (and/or or by a machine). In use, the introducer 4404 may be inserted into a breast (or other part of the patient) so that the delivery opening 4306 is positioned within the patient (such as a cavity formed in the breast, for example). Depressing on the piston 4408, in turn, causes the distal end thereof (which is inserted into the internal lumen 4404) to come into contact with and to push the proximal most one of the elements 4302, 4304. As the piston is further depressed in the direction of the arrow 4410, the elements 4302, 4404 act upon each other and are collectively pushed out of the delivery opening 4306 and into the intended delivery site of the soft tissue marker. This is the state that is illustrated in FIG. 45. As shown therein, the markers (the elements 4302, 4304) then move into the cavity 4504 in the breast 4502. The substantially non-swellable element(s) 4302 and the radiopaque element(s) 4304, are then free to move relative to one another within the cavity 4504 so that they may assume a number of different positions relative to one another in the cavity 4504. Each of the markers 4302, 4304 and the combination of the markers 4302, 4304 are configured to appear clearly artificial or man-made when visualized by the surgeon. That is, the marker or markers 4302 are configured to appear clearly artificial when viewed under ultrasound and the marker of markers 4304 are configured to appear clearly artificial or man-made when viewed under X-ray. In turn, the soft tissue marker delivered to the cavity 4504 is configured to be readily identifiable as an artificial structure within the breast when viewed under ultrasound and/or X-ray. That is, the soft tissue marker (in whatever positions the markers 4302, 4304 assume relative to one another in the cavity 4504) should be clearly discernable from among the other soft tissue, scar tissue, fluids and fibrous tissue at the implant site, through such imaging modalities as ultrasound and X-ray.

FIGS. 46, 47 and 48 shows different implementations of the soft tissue marker, according to further embodiments of the present invention. As shown therein, the elements 4302, 4304 need not have the shapes shown in FIGS. 43 and 44. Indeed, the soft tissue marker may include non-swellable elements configured to be visualized under ultrasound that may have most any shape. For example, while the markers 4302 shown in FIGS. 43, 44 and 45 are of a generally cylindrical shape, that need not be the case. For example, as shown in FIG. 45, the soft tissue marker may include echogenic elements whose shape may be characterized as roughly rectangular, such as shown at 4602. Most any other shapes are possible, subject to manufacturability and cost constraints. As also shown in FIG. 46, one or more of the echogenic elements may be of a first shape, while others of the echogenic elements of the soft tissue marker may have another or other shapes. In the exemplary embodiment of FIG. 46, some of the echogenic elements are generally cylindrical in shape (4302), while others are generally rectangular in shape. As also shown in FIGS. 46, 47 and 48, the shape of the radiopaque element may also be varied at will. Indeed, the radiopaque element may be shaped as a spring 4604 or any other shape, such as shown at 4704. The shape of the radiopaque element may be selected so as to be readily recognizable as an artificial item within the implant site under ultrasound, X-ray or other visualization modality. The shape of the radiopaque element may also be selected so as to promote its adhesion to the walls of the cavity 4504.

As shown in FIGS. 47 and 48, the soft tissue marker may include any number of echogenic markers and any number radiopaque markers. The radiopaque markers may be disposed anywhere relative to the echogenic markers, including in the leading or trailing positions. The echogenic markers may include markers having different porosity characteristics, including, for example, different pore densities. Indeed, some of the echogenic markers may have different pore density/orientation/shape/dimensions and/or other characteristics than others in the soft tissue marker. As shown in FIGS. 47 and 48, the soft tissue marker may include echogenic markers 4702 having a first pore density, markers such as shown at 4802 that have a second pore density that is higher (more porous) than the first pore density, and markers as shown at 4804 that have a third pore density that is even higher (even more porous) than either of the first and second pore densities.

FIG. 49 shows a soft tissue marker according to another embodiment of the present invention. The discrete elements 4902 may have echogenic properties and element 4904 may be radiopaque. Unlike the embodiments of FIGS. 43-48, at least some of the echogenic elements 4902 may be coupled to one another with a biodegradable string or suture element 4906. That is, the echogenic elements 4902 on one side of the radiopaque element 4904 may be coupled to one another with a first biodegradable string 4906 and the echogenic elements 4902 may be coupled to one another with a second biodegradable string 4906. The radiopaque element 4904 may be a discrete element, unattached to any of the echogenic elements 4902. Alternatively, as shown in FIG. 49, a single biodegradable string or suture 4906 may be threaded through each of the echogenic and radiopaque elements 4902, 4904, much like pearls on a string. This embodiment tends to maintain the echogenic and radiopaque elements aligned with one another, even as the train of elements 4902, 4904 twists and bends inside the biopsy cavity. This results in a clearly recognizable artificial structure inside the cavity, as the suture 4906 imposes some degree of single file order to the train of echogenic and radiopaque elements of the soft tissue marker. The biodegradable string 4906 may be formed of or may include a vycril (PLA/PGA) suture, although other suitable biodegradable materials may be used, such as collagen (cut-gut suture), for example. The embodiments described herein relative to FIGS. 43-48 may also be provided with a biodegradable string 4906, to couple two or more of the echogenic and radiopaque elements together.

FIG. 50 shows another embodiment of a soft tissue marker, according to the present inventions. As shown therein, each of the echogenic elements 5002 may feature a leading or trailing face that defines an inclined plane with respect to the long axis of the echogenic element. Such an inclined leading or trailing face may be manufactured by cutting an echogenic element 4902 along a plane that is inclined with respect to the long axis of the element. For example, the echogenic elements may be cut along a plane 5003 and/or 5007 as shown in FIG. 50, to create first and second echogenic elements 5002a, 5002b.

Each of the halves may measure about between about 1 and 10 mm for example. According to one embodiment, each of the halves may measure about 5 mm, for example, although other embodiments may feature differently sized echogenic elements. The inclines faces of the echogenic elements 5002 may ease the delivery of the train of echogenic and radiopaque elements 5002, 5004 within the cavity and may result in a more easily visualized pattern of deposition. A biodegradable string such as shown at 4906 may couple one or more of the echogenic and radiopaque elements 5002, 5004.

FIG. 51 shows another soft tissue marker, according to yet another embodiment of the present invention. As shown therein, the marker (shown in FIGS. 51-53 in simplified cross-section) may include a first section 5102 and a second section 5106. Each of the first and second sections 5102, 5106 may include a single length of echogenic element into which a plurality of cutouts or crenellations 5103 have been cut, formed or defined. The crenellations 5103 may be formed when the sheet of echogenic material was manufactured, by a molding, stamping or other forming process. The crenellations 5103 form alternating relatively thicker portions 5108 and relatively thinner portions 5110, as shown in FIGS. 51-53. The relatively thinner portions 5108 are more easily bendable than the locally thicker portions and thus act as hinges, enabling each of the first and second sections 5102 and 5106 to easily deploy and to bend and bunch within the cavity after deployment. Indeed, FIG. 52 shows the distal-most portion of an applicator or introducer 5202 that may be used to deliver the marker of FIG. 51 into a cavity (such as a breast biopsy site, for example) within a patient. As shown, the introducer 5202 may define a distal opening 5026 through which the marker may be deployed. The introducer 5020 may include an inclined surface 5204 near the distal tip thereof. The marker shown in FIG. 51 may be pushed into the cavity by an internal piston (such as shown and described relative to FIGS. 44 and 45). As the free distal end of the marker rides up the inclined surface 5204, the locally thinner portions 5108 bend and clear the distal tip of the introducer 5202. Once pushed into the cavity, the marker may bend, twist and/or bunch up against the walls of the cavity and/or any internal structures therein, without loosing its structural integrity. Therefore, the marker will remain readily visualizable inside the cavity. It is to be understood that different aspects the embodiments of FIGS. 43-53 may be combined to advantageous effect. For example, the embodiment of FIG. 51 may be combined with that of FIG. 49 to include a biodegradable string 4906 or to include the multiple radiopaque elements of FIG. 8. Alternatively still, the first and second sections 5102, 5106 may feature different cross-sectional shapes (e.g., rectangular or cylindrical) pore density profiles, pore alignment profiles or any of the different structures, features, materials or properties discussed herein above, as may the embodiments of FIGS. 49 and 50.

FIG. 54 shows a tissue marker (in simplified cross-section), according to another embodiment of the present invention. The marker of FIG. 54 is similar to that of FIG. 51, but for the distal ends of the first and second sections 5402, 5404 that define a leading inclined surface 5403, 5405. The leading inclined surfaces 5403, 5405 may affect the manner in which the first and second sections enter and/or travel within the cavity and the manner in which the first and second sections bend and bunch up within the cavity. Moreover, as shown in FIG. 54, the crenellations of the first section 5402 may face in a first direction (e.g., up in FIG. 54) and the crenellations of the second section 5404 may face a second direction that is different than the first direction (down in FIG. 54). The orientation of the crenellations also affects the orientation of the inclined leading surfaces 5403, 5405. Therefore, the first and second sections 5402, 5404 may bend in different directions within the cavity, after deployment. FIG. 55A shows the marker of FIG. 54 loaded into an introducer, such as shown and described relative to FIGS. 44 and 45. FIG. 55B shows the marker of FIG. 54 in a deployed state, after having been pushed out of the applicator or introducer and into the cavity. As may be seen, the orientation of the crenellations and the orientation of the leading inclined surfaces 5403, 5405 may cause the first and second sections to bend, twist and/or bunch up differently from one another, thereby forming a distinct shape that may be looked for and recognized when the cavity is visualized.

While the foregoing detailed description has described preferred embodiments of the present invention, it is to be understood that the above description is illustrative only and not limiting of the disclosed invention. Those of skill in this art may recognize other alternative embodiments and all such alternative embodiments are deemed to fall within the scope of the present invention.

What is claimed is:

1. A device to deliver a soft tissue marker, comprising:
an introducer that defines an internal lumen;
a plurality of discrete substantially non-swellable elements disposed within the internal lumen, each being formed of at least one of a porous material and a non-porous material, and
a radiopaque element disposed within the internal lumen adjacent to at least one of the plurality of discrete substantially non-swellable elements, the radiopaque element being external to and uncoupled from each of the plurality of discrete substantially non-swellable elements.

2. The device of claim 1, wherein the porous material defines surfaces that form interconnected internal voids.

3. The device of claim 1, wherein the porous material defines internal surfaces that form internal voids and wherein a majority of the internal surfaces are common to more than one of the internal voids.

4. The device of claim 1, wherein the porous material defines surfaces that form primarily interconnected internal voids, as opposed to forming primarily entrapped discrete bubbles.

5. The device of claim 1, wherein the porous material has a controlled pore architecture with respect to at least one of pore density, pore shape, pore orientation and pore dimensions.

6. The device of claim 1, wherein at least one of the plurality of discrete substantially non-swellable elements has a degree of porosity that is different from a degree of porosity of another one of the plurality of discrete substantially non-swellable elements.

7. The device of claim 1, wherein both the porous material and the non-porous material are configured to promote echogenicity.

8. The device of claim 1, wherein the porous material of one of the plurality of discrete substantially non-swellable elements has a first controlled pore architecture and wherein the porous material of an other one of the plurality of discrete substantially non-swellable elements has a second controlled pore architecture that is different from the first controlled pore architecture.

9. The device of claim 8, wherein the first controlled pore architecture differs from the second controlled pore architecture with respect to at least one of: pore density, pore shape, pore orientation and pore dimensions.

10. The device of claim 1, wherein the porous material of the plurality of discrete substantially non-swellable elements is biodegradable.

11. The device of claim 1, wherein the porous material of at least one of the plurality of discrete substantially non-swellable elements includes at least one of a polylactide (PLA), a polyglycolide (PGA), a poly(lactide-co-glycolide) (PLA-PGA), a polyglyconate, a polyanhydride, a lipid, a polysaccharide, and a polyorthoester.

12. The device of claim 1, wherein at least one of the plurality of discrete substantially non-swellable elements has a first shape and wherein an other one of the plurality of discrete substantially non-swellable elements has a second shape that is different from the first shape.

13. The device of claim 1, wherein at least one of the plurality of discrete substantially non-swellable elements has a substantially cylindrical shape.

14. The device of claim 1, wherein at least one of the plurality of discrete substantially non-swellable elements has a substantially rectangular shape.

15. The device of claim 1, wherein the radiopaque element is configured to appear clearly artificial when viewed under X-ray.

16. The device of claim 1, wherein the radiopaque element is configured to appear clearly artificial when viewed under ultrasound.

17. The device of claim 1, wherein the radiopaque element is formed of a non-ferrous metal.

18. The device of claim 1, wherein the radiopaque element includes a portion having a paramagnetic property.

19. The device of claim 1, further including more than one radiopaque element disposed within the internal lumen of the introducer.

20. The device of claim 1, wherein the plurality of discrete substantially non-swellable elements are configured to appear clearly artificial when viewed under ultrasound.

21. The device of claim 1, wherein a combination of the plurality of discrete substantially non-swellable elements and the radiopaque element are configured to appear clearly artificial when viewed under ultrasound.

22. A soft tissue marker for delivery to a biopsy site within a patient, comprising:
    a plurality of discrete substantially non-swellable elements, each being formed of at least one of a porous material and a non-porous material, and
    a radiopaque element disposed adjacent to at least one of the plurality of discrete substantially non-swellable elements, the radiopaque element being external to and uncoupled from each of the plurality of discrete substantially non-swellable elements.

23. The soft tissue marker of claim 22, wherein the porous material defines surfaces that form interconnected internal voids.

24. The soft tissue marker of claim 22, wherein the porous material defines internal surfaces that form internal voids and wherein a majority of the internal surfaces are common to more than one of the internal voids.

25. The soft tissue marker of claim 22, wherein the porous material defines surfaces that form primarily interconnected internal voids, as opposed to forming primarily entrapped discrete bubbles.

26. The soft tissue marker of claim 22, wherein the porous material has a controlled pore architecture with respect to at least one of pore density, pore shape, pore orientation and pore dimensions.

27. The soft tissue marker of claim 22, wherein at least one of the plurality of discrete substantially non-swellable elements has a degree of porosity that is different from a degree of porosity of another one of the plurality of discrete substantially non-swellable elements.

28. The soft tissue marker of claim 22, wherein both the porous material and the non-porous material are configured to promote echogenicity.

29. The soft tissue marker of claim 22, wherein the porous material of one of the plurality of discrete substantially non-swellable elements has a first controlled pore architecture and wherein the porous material of an other one of the plurality of discrete substantially non-swellable elements has a second controlled pore architecture that is different from the first controlled pore architecture.

30. The soft tissue marker of claim 29, wherein the first controlled pore architecture differs from the second controlled pore architecture with respect to at least one of: pore density, pore shape, pore orientation and pore dimensions.

31. The soft tissue marker of claim 22, wherein the porous material of the plurality of discrete substantially non-swellable elements is biodegradable.

32. The soft tissue marker of claim 22, wherein the porous material of at least one of the plurality of discrete substantially non-swellable elements includes at least one of a polylactide (PLA), a polyglycolide (PGA), a poly(lactide-co-glycolide) (PLA-PGA), a polyglyconate, a polyanhydride, a lipid, a polysaccharide, and a polyorthoester.

33. The soft tissue marker of claim 22, wherein at least one of the plurality of discrete substantially non-swellable elements has a first shape and wherein an other one of the plurality of discrete substantially non-swellable elements has a second shape that is different from the first shape.

34. The soft tissue marker of claim 22, wherein at least one of the plurality of discrete substantially non-swellable elements has a substantially cylindrical shape.

35. The soft tissue marker of claim 22, wherein at least one of the plurality of discrete substantially non-swellable elements has a substantially rectangular shape.

36. The soft tissue marker of claim 22, wherein the radiopaque element is configured to appear clearly artificial when viewed under X-ray.

37. The soft tissue marker of claim 22, wherein the radiopaque element is configured to appear clearly artificial when viewed under ultrasound.

38. The soft tissue marker of claim 22, wherein the radiopaque element is formed of a non-ferrous metal.

39. The soft tissue marker of claim 22, wherein the radiopaque element includes a portion having a paramagnetic property.

40. The soft tissue marker of claim 22, further including more than one radiopaque element disposed within the internal lumen of the introducer.

41. The soft tissue marker of claim 22, wherein the plurality of discrete substantially non-swellable elements are configured to appear clearly artificial when viewed under ultrasound.

42. The soft tissue marker of claim 22, wherein a combination of the plurality of discrete substantially non-swellable elements and the radiopaque element are configured to appear clearly artificial when viewed under ultrasound.

43. A method for marking a biopsy site within a patient, comprising the steps of:
    providing a device having a proximal end, an open distal end, an internal lumen and a piston that is movable within the internal lumen; a plurality of discrete substantially non-swellable elements disposed within the internal lumen, each of which being formed of at least one of a porous material and a non-porous material, and a radiopaque element disposed within the internal lumen adjacent to at least one of the plurality of discrete substantially non-swellable elements, the radiopaque element being external to and uncoupled from each of the plurality of discrete substantially non-swellable porous elements;

introducing the distal end of the device into the biopsy site, and advancing the piston in a distal direction so that the plurality of discrete substantially non-swellable elements and the radiopaque element are pushed out the open distal end of the device and into the biopsy site.

44. The method of claim 43, wherein the providing step is carried out with the porous material defining surfaces that form interconnected internal voids.

45. The method of claim 43, wherein the providing step is carried out with the porous material defining internal surfaces that form internal voids and wherein a majority of the internal surfaces are common to more than one of the internal voids.

46. The method of claim 43, wherein the providing step is carried out with the porous material defining surfaces that form primarily interconnected internal voids, as opposed to forming primarily entrapped discrete bubbles.

47. The method of claim 43, wherein the providing step is carried out with the porous material having a controlled pore architecture with respect to at least one of pore density, pore shape, pore orientation and pore dimensions.

48. The method of claim 43, wherein the providing step is carried out with at least one of the plurality of discrete substantially non-swellable elements having a degree of porosity that is different from a degree of porosity of another one of the plurality of discrete substantially non-swellable elements.

49. The method of claim 43, wherein the providing step is carried out with both the porous material and the non-porous material being configured to promote echogenicity.

50. The method of claim 43, wherein the providing step is carried out with the porous material of one of the plurality of discrete substantially non-swellable elements having a first controlled pore architecture and wherein the porous material of an other one of the plurality of discrete substantially non-swellable elements has a second controlled pore architecture that is different from the first controlled pore architecture.

51. The method of claim 50, wherein the providing step is carried out with the first controlled pore architecture differing from the second controlled pore architecture with respect to at least one of: pore density, pore shape, pore orientation and pore dimensions.

52. The method of claim 43, wherein the providing step is carried out with the porous material of the plurality of discrete substantially non-swellable elements being biodegradable.

53. The method of claim 43, wherein the providing step is carried out with the porous material of at least one of the plurality of discrete substantially non-swellable elements including at least one of a polylactide (PLA), a polyglycolide (PGA), a poly(lactide-co-glycolide) (PLA-PGA), a polyglyconate, a polyanhydride, a lipid, a polysaccharide, and a polyorthoester.

54. The method of claim 43, wherein the providing step is carried out with at least one of the plurality of discrete substantially non-swellable elements having a first shape and wherein an other one of the plurality of discrete substantially non-swellable elements has a second shape that is different from the first shape.

55. The method of claim 43, wherein the providing step is carried out with at least one of the plurality of discrete substantially non-swellable elements having a substantially cylindrical shape.

56. The method of claim 43, wherein the providing step is carried out with at least one of the plurality of discrete substantially non-swellable elements having a substantially rectangular shape.

57. The method of claim 43, wherein the providing step is carried out with the radiopaque element being configured to appear clearly artificial when viewed under X-ray.

58. The method of claim 43, wherein the providing step is carried out with the radiopaque element being configured to appear clearly artificial when viewed under ultrasound.

59. The method of claim 43, wherein the providing step is carried out with the radiopaque element being formed of a non-ferrous metal.

60. The method of claim 43, wherein the providing step is carried out with the radiopaque element including a portion having a paramagnetic property.

61. The method of claim 43, wherein the providing step is carried out with the device further including more than one radiopaque element disposed within the internal lumen of the introducer.

62. The method of claim 43, wherein the providing step is carried out with the plurality of discrete substantially non-swellable elements being configured to appear clearly artificial when viewed under ultrasound.

63. The method of claim 43, wherein the providing step is carried out with a combination of the plurality of discrete substantially non-swellable elements and the radiopaque element being configured to appear clearly artificial when viewed under ultrasound.

64. A method of marking a cavity in a breast for subsequent visualization, comprising the steps of:

providing a device having a delivery opening, a first marker and a second marker, the first and second markers being movable through the delivery opening, the first marker being configured to be visualized by ultrasound and the second marker configured to be radiopaque, the first and second markers being free to move relative to one another;

introducing the device into a breast so that the delivery opening is positioned in a cavity formed in the breast; and moving the first marker and the second marker through the delivery opening and into the cavity in the breast, the first and second markers being free to move relative to one another when delivered into the cavity so that the first and second markers may take a number of different positions relative to one another when positioned within the cavity.

65. The method of claim 64, wherein the providing step is carried out with the first marker being a polymer having a porous structure which enhances visibility of the first marker under ultrasound, the second marker being a metallic structure which enhances visibility of the second marker under x-ray.

66. The method of claim 64, wherein the providing step is carried out with the first marker being substantially non-swellable.

67. The method of claim 64, wherein the providing step is carried out with the first marker being uncoupled from the second marker.

68. The method of claim 64, wherein the providing step is carried out with the first marker including surfaces that form interconnected internal voids.

69. The method of claim 64, wherein the providing step is carried out with the first marker defining internal surfaces that form internal voids and wherein a majority of the internal surfaces are common to more than one of the internal voids.

70. The method of claim 64, wherein the providing step is carried out with the first marker defining surfaces that form primarily interconnected internal voids, as opposed to forming primarily entrapped discrete bubbles.

71. The method of claim 64, wherein the providing step is carried out with the first marker being porous and having a controlled pore architecture with respect to at least one of pore density, pore shape, pore orientation and pore dimensions.

72. The method of claim 64, wherein the providing step is carried out with the device including a third marker configured to be visualized by ultrasound, wherein the first and third markers are porous, and wherein the first marker has a degree of porosity that is different from a degree of porosity of the third marker.

73. The method of claim 64, wherein the providing step is carried out with the device including a third marker configured to be visualized by ultrasound, wherein the first marker has a first controlled pore architecture and the third marker has a second controlled pore architecture, and wherein the first controlled pore architecture is different from the second controlled pore architecture.

74. The method of claim 73, wherein the providing step is carried out with the first controlled pore architecture differing from the second controlled pore architecture with respect to at least one of: pore density, pore shape, pore orientation and pore dimensions.

75. The method of claim 64, wherein the providing step is carried out with the first marker being biodegradable.

76. The method of claim 64, wherein the providing step is carried out with the first marker including at least one of a polylactide (PLA), a polyglycolide (PGA), a poly(lactide-co-glycolide) (PLA-PGA), a polyglyconate, a polyanhydride, a lipid, a polysaccharide, and a polyorthoester.

77. The method of claim 64, wherein the providing step is carried out with the first marker having a first shape and with the second marker having a second shape that is different from the first shape.

78. The method of claim 64, wherein the providing step is carried out with the device including a third marker configured to be visualized by ultrasound, the third marker being free to move relative to the first and second markers.

79. The method of claim 64, wherein the providing step is carried out with the third marker having a different shape than the first marker.

80. The method of claim 64, wherein the providing step is carried out with the first marker having a substantially cylindrical shape.

81. The method of claim 64, wherein the providing step is carried out with the first marker having a substantially rectangular shape.

82. The method of claim 64, wherein the providing step is carried out with the second marker being configured to appear clearly artificial when viewed under X-ray.

83. The method of claim 64, wherein the providing step is carried out with the second marker also being to appear clearly artificial when viewed under ultrasound.

84. The method of claim 64, wherein the providing step is carried out with the second marker including a non-ferrous metal.

85. The method of claim 64, wherein the providing step is carried out with the second marker including a portion having a paramagnetic property.

86. The method of claim 64, wherein the providing step is carried out with the device further a third marker that is configured to be radiopaque.

87. The method of claim 86, wherein the third marker is free to move relative to the first and second markers.

88. The method of claim 64, wherein the providing step is carried out with the first and second markers being configured to appear clearly artificial when viewed under ultrasound.

89. The method of claim 64, wherein the providing step is carried out with a combination of the first and second markers being configured to appear clearly artificial when viewed under ultrasound.

90. A soft tissue marker for delivery to a cavity within a patient, comprising:
a plurality of discrete echogenic and biodegradable elements;
a radiopaque element disposed adjacent to at least one and external to each of the plurality of discrete echogenic and biodegradable elements, and
a biodegradable string coupling at least some of the plurality of discrete echogenic and biodegradable elements.

91. The soft tissue marker of claim 90, wherein the biodegradable string is also coupled to the radiopaque element.

92. The soft tissue marker of claim 90, wherein the biodegradable string is a biodegradable suture.

93. The soft tissue marker of claim 90, wherein the biodegradable string includes vycril.

94. The soft tissue marker of claim 90, wherein the biodegradable string includes collagen.

95. The soft tissue marker of claim 90, wherein each of the plurality of discrete echogenic and biodegradable elements includes a porous material that defines surfaces that form interconnected internal voids.

96. The soft tissue marker of claim 90, wherein each of the plurality of discrete echogenic and biodegradable elements is substantially non-swellable.

97. A soft tissue marker for delivery to a cavity within a patient, comprising:
a plurality of discrete echogenic and biodegradable elements, each of the plurality of discrete echogenic and biodegradable elements defining a longitudinal axis and including at least one of a leading and a trailing surface that is inclined away from a normal to the longitudinal axis, and
a radiopaque element disposed adjacent to at least one and external to each of the plurality of discrete echogenic and biodegradable elements.

98. The soft tissue marker of claim 97, wherein each of the plurality of discrete echogenic and biodegradable elements includes a porous material that defines surfaces that form interconnected internal voids.

99. The soft tissue marker of claim 97, wherein each of the plurality of discrete echogenic and biodegradable elements is substantially non-swellable.

100. A soft tissue marker for delivery into a cavity within a patient, comprising:
a first echogenic and biodegradable element that defines a first plurality of crenellations that define a corresponding first plurality of locally thinner and thicker portions;
a second echogenic and biodegradable element that defines a second plurality of crenellations that define a corresponding second plurality of locally thinner and thicker portions, and
a radiopaque element disposed adjacent to at least one of the first and second echogenic and biodegradable elements and external to each of the first and second echogenic and biodegradable elements.

101. The soft tissue marker of claim 100, wherein each of the first and second echogenic and biodegradable elements includes a porous material that defines surfaces that form interconnected internal voids.

102. The soft tissue marker of claim 100, wherein each of the first and second echogenic and biodegradable elements is substantially non-swellable.

103. The soft tissue marker of claim 100, wherein the locally thinner portions are configured, when the marker is delivered into the cavity, to bend more than the locally thicker portions, thereby imparting a distinctive shape to the first and second echogenic and biodegradable elements within the cavity.

* * * * *